United States Patent
Chang et al.

(10) Patent No.: US 11,560,567 B2
(45) Date of Patent: Jan. 24, 2023

(54) GENETIC ELEMENTS DRIVING CIRCULAR RNA TRANSLATION AND METHODS OF USE

(71) Applicant: The Board of Trustees of the Leland Stanford Junior University, Stanford, CA (US)

(72) Inventors: Howard Y. Chang, Stanford, CA (US); Chun-Kan Chen, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/696,606

(22) Filed: Mar. 16, 2022

(65) Prior Publication Data

US 2022/0251578 A1     Aug. 11, 2022

Related U.S. Application Data

(63) Continuation of application No. PCT/US2021/039127, filed on Jun. 25, 2021.

(60) Provisional application No. 63/186,507, filed on May 10, 2021, provisional application No. 63/043,964, filed on Jun. 25, 2020.

(51) Int. Cl.
| | |
|---|---|
| *C07H 21/02* | (2006.01) |
| *C07H 21/04* | (2006.01) |
| *C12N 15/67* | (2006.01) |
| *C12N 15/113* | (2010.01) |
| *C12N 15/85* | (2006.01) |

(52) U.S. Cl.
CPC ............ *C12N 15/67* (2013.01); *C12N 15/113* (2013.01); *C12N 15/85* (2013.01); *C12N 2840/203* (2013.01)

(58) Field of Classification Search
CPC .................................................. C12N 15/113
See application file for complete search history.

(56) References Cited

U.S. PATENT DOCUMENTS

| | | | |
|---|---|---|---|
| 5,766,903 | A | 6/1998 | Sarnow et al. |
| 2016/0082092 | A1 | 3/2016 | Hoerr et al. |
| 2016/0083747 | A1 | 3/2016 | Kruse |
| 2018/0044739 | A1 | 2/2018 | Weinbaum et al. |
| 2019/0345503 | A1 | 11/2019 | Chang et al. |

FOREIGN PATENT DOCUMENTS

| | | |
|---|---|---|
| WO | WO2010084371 A1 | 7/2010 |
| WO | WO2014082644 A1 | 6/2014 |
| WO | WO2016011222 A2 | 1/2016 |
| WO | WO2017081082 A2 | 5/2017 |
| WO | WO2017222911 A1 | 12/2017 |
| WO | WO2020023655 A1 | 1/2020 |
| WO | WO2020219563 A1 | 10/2020 |

OTHER PUBLICATIONS

Ahmad et al., "Breaching Self-Tolerance to Alu Duplex RNA Underlies MDA5-Mediated Inflammation." Cell. Feb. 8, 2018;172(4):797-810.e13.
Baranick et al., "Splicing mediates the activity of four putative cellular internal ribosome entry sites." Proc Natl Acad Sci USA. Mar. 25, 2008;105(12):4733-8.
Batista et al., "m(6)A RNA modification controls cell fate transition in mammalian embryonic stem cells." Cell Stem Cell. Dec. 4, 2014;15(6):707-19.
Bert et al., "Assessing IRES activity in the HIF-1 alpha and other cellular 5' UTRs." RNA. Jun. 2006;12(6):1074-83.
Brito et al., "A cationic nanoemulsion for the delivery of next-generation RNA vaccines." Mol Ther. Dec. 2014;22(12):2118-29.
Chandry et al., "Activation of a cryptic 5' splice site in the upstream exon of the phage T4 td transcript: exon context, missplicing, and mRNA deletion in a fidelity mutant." Genes Dev. Nov. 1987;1(9):1028-37.
Chen et al., "N6-Methyladenosine Modification Controls Circular RNA Immunity". Mol Cell. Oct. 3, 2019;76(1):96-109.e9.
Chen et al., "Pervasive functional translation of noncanonical human open reading frames." Science. Mar. 6, 2020;367(6482):1140-1146.
Chen et al., "Sensing Self and Foreign Circular RNAs by Intron Identity." Mol Cell. Jul. 20, 2017;67(2):228-238.e5.
Chu et al., "Systematic discovery of Xist RNA binding proteins." Cell. Apr. 9, 2015;161(2):404-16.
Crooke et al., "RNA-Targeted Therapeutics." Cell Metab. Apr. 3, 2018;27(4):714-739.
Devarkar et al., "Structural basis for m7G recognition and 2'-O-methyl discrimination in capped RNAs by the innate immune receptor RIG-I." Proc Natl Acad Sci USA. Jan. 19, 2016;113(3):596-601.
Dobrikova et al., "Activity of a type 1 picornavirus internal ribosomal entry site is determined by sequences within the 3' nontranslated region." Proc Natl Acad Sci USA. Dec. 9, 2003;100(25):15125-30.
Dolinnaya et al., "Oligonucleotide circularization by template-directed chemical ligation." Nucleic Acids Res. Nov. 25, 1993;21(23):5403-7.
Dolinnaya et al., "The use of BrCN for assembling modified DNA duplexes and DNA-RNA hybrids; comparison with water-soluble carbodiimide." Nucleic Acids Res. Jun. 11, 1991;19(11):3067-72.
Dominissini et al., "Topology of the human and mouse m6A RNA methylomes revealed by m6A-seq." Nature. Apr. 9, 2012;485(7397):201-6.

(Continued)

*Primary Examiner* — Amy H Bowman
(74) *Attorney, Agent, or Firm* — Casimir Jones, S.C.; Tanya A. Arenson

(57) ABSTRACT

Provided herein are recombinant circular RNA (circRNA) molecules comprising an internal ribosome entry site (IRES) operably linked to a protein-coding nucleic acid sequence. The IRES includes at least one RNA secondary structure element; and a sequence region that is complementary to an 18S ribosomal RNA (rRNA). Methods of producing a protein in a cell using the recombinant circRNA molecules are also provided.

20 Claims, 53 Drawing Sheets

Specification includes a Sequence Listing.

(56) References Cited

OTHER PUBLICATIONS

Durbin et al., "RNAs Containing Modified Nucleotides Fail to Trigger RIG-I Conformational Changes for Innate Immune Signalingm." Bio. 2016. 7: e00833-00816. 11 pages.

Edupuganti et al., "N 6-methyladenosine (m 6 A) recruits and repels proteins to regulate mRNA homeostasis." Nat Struct Mol Biol. Oct. 2017;24(10):870-878.

European Search Report for related EP17815958.8, dated Dec. 5, 2019, 12 pages.

Fedorova et al. "Cyanogen bromide-induced chemical ligation: Mechanism and optimization of the reaction conditions." Nucleosides, Nucleotides & Nucleic Acids 15.6 (1996): 1137-1147.

Ford et al., "Synthesis of circular RNA in bacteria and yeast using RNA cyclase ribozymes derived from a group I intron of phage T4." Proc Natl Acad Sci USA. Apr. 12, 1994;91(8):3117-21.

Garlapati et al., "Identification of a novel internal ribosome entry site in giardiavirus that extends to both sides of the initiation codon." J Biol Chem. Jan. 30, 2004;279(5):3389-97.

Glazar et al., "circBase: a database for circular RNAs." RNA. Nov. 2014;20(11):1666-70.

Gurtu et al., "IRES bicistronic expression vectors for efficient creation of stable mammalian cell lines." Biochem Biophys Res Commun. Dec. 4, 1996;229(1):295-8.

Hansen et al., "Natural RNA circles function as efficient microRNA sponges." Nature. Mar. 21, 2013;495(7441):384-8.

Haussecker et al., "Capped small RNAs and MOV10 in human hepatitis delta virus replication." Nat Struct Mol Biol. Jul. 2008;15(7):714-21.

Holdt et al., "Circular RNAs as Therapeutic Agents and Targets." Front Physiol. Oct. 9, 2018;9:1262.

Hornung et al., "5'-Triphosphate RNA is the ligand for RIG-I." Science. Nov. 10, 2006;314(5801):994-7.

International Search Report and Written Opinion for PCT/US20/47995. dated Jan. 26, 2021. 9 pages.

International Search Report and Written Opinion for PCT/US2021/039127. dated Dec. 13, 2021. 17 pages.

International Search Report of related PCT/US2017/037702, dated Oct. 27, 2017, 12 pages.

Jang et al., "Initiation of protein synthesis by internal entry of ribosomes into the 5' nontranslated region of encephalomyocarditis virus RNA in vivo." J Virol. Apr. 1989;63(4):1651-60.

Jeck et al., "Circular RNAs are abundant, conserved, and associated with ALU repeats." RNA. Feb. 2013;19(2):141-57.

Jeck et al., "Detecting and characterizing circular RNAs." Nat Biotechnol. May 2014;32(5):453-61.

Jiang et al., "A Quantitative Proteome Map of the Human Body." Cell. Oct. 1, 2020;183(1):269-283.e19.

Jiang et al., "Ubiquitin-induced oligomerization of the RNA sensors RIG-I and MDA5 activates antiviral innate immune response." Immunity. Jun. 29, 2012;36(6):959-73.

Kato et al., "Cell type-specific involvement of RIG-I in antiviral response." Immunity. Jul. 2005;23(1):19-28.

Kato et al., "Length-dependent recognition of double-stranded ribonucleic acids by retinoic acid-inducible gene-I and melanoma differentiation-associated gene 5." J Exp Med. Jul. 7, 2008;205(7):1601-10.

Kaufman et al., "Improved vectors for stable expression of foreign genes in mammalian cells by use of the untranslated leader sequence from EMC virus." Nucleic Acids Res. Aug. 25, 1991;19(16):4485-90.

Ke et al., "A majority of m6A residues are in the last exons, allowing the potential for 3' UTR regulation." Genes Dev. Oct. 1, 2015;29(19):2037-53.

Kobayashi et al., "Improved dicistronic mRNA expression vectors for efficient selection of transfectants highly expressing foreign genes." Biotechniques. Sep. 1996;21(3):398-402.

Kos et al., "The hepatitis delta (delta) virus possesses a circular RNA." Nature. Oct. 9-15, 1986;323(6088):558-60.

Kramer et al., "Combinatorial control of Drosophila circular RNA expression by intronic repeats, hnRNPs, and SR proteins." Genes Dev. Oct. 15, 2015;29(20):2168-82.

Kramps et al., "Messenger RNA-based vaccines: progress, challenges, applications." Wiley Interdiscip Rev RNA. Nov.-Dec. 2013;4(6):737-49.

Krutzfeldt et al., "Silencing of microRNAs in vivo with 'antagomirs'." Nature. Dec. 1, 2005;438(7068):685-9.

Li et al., "Coordinated circRNA Biogenesis and Function with NF90/NF110 in Viral Infection." Mol Cell. Jul. 20, 2017;67(2):214-227.e7.

Liang et al., "Short intronic repeat sequences facilitate circular RNA production." Genes Dev. Oct. 15, 2014;28(20):2233-47.

Liu et al., "Structure and Degradation of Circular RNAs Regulate PKR Activation in Innate Immunity." Cell. May 2, 2019;177(4):865-880.e21.

Martin et al., "Translation of the human angiotensin II type 1 receptor mRNA is mediated by a highly efficient internal ribosome entry site." Mol Cell Endocrinol. Dec. 30, 2003;212(1-2):51-61.

Martineau et al., "Internal ribosome entry site structural motifs conserved among mammalian fibroblast growth factor 1 alternatively spliced mRNAs." Mol Cell Biol. Sep. 2004;24(17):7622-35.

Memczak et al., "Circular RNAs are a large class of animal RNAs with regulatory potency." Nature. Mar. 21, 2013;495(7441):333-8.

Meyer et al., "Comprehensive analysis of mRNA methylation reveals enrichment in 3' UTRs and near stop codons." Cell. Jun. 22, 2012;149(7):1635-46.

Mokrejš et al., "IRESite—a tool for the examination of viral and cellular internal ribosome entry sites." Nucleic Acids Res. Jan. 2010;38(Database issue):D131-6.

Molinie et al., "m(6)A-LAIC-seq reveals the census and complexity of the m(6)A epitranscriptome." Nat Methods. Aug. 2016;13(8):692-8.

Mosser et al., "Use of a dicistronic expression cassette encoding the green fluorescent protein for the screening and selection of cells expressing inducible gene products." Biotechniques. Jan. 1997;22(1):150-161.

Olexiouk et al., "An update on sORFs.org: a repository of small ORFs identified by ribosome profiling." Nucleic Acids Res. Jan. 4, 2018;46(D1):D497-D502.

Pedersen et al., "Human insulin-like growth factor II leader 2 mediates internal initiation of translation." Biochem J. Apr. 1, 2002;363(Pt 1):37-44.

Peisley et al., "RIG-I forms signaling-competent filaments in an ATP-dependent, ubiquitin-independent manner." Mol Cell. Sep. 12, 2013;51(5):573-83.

Peisley et al., "Structural basis for ubiquitin-mediated antiviral signal activation by RIG-I." Nature. May 1, 2014;509(7498):110-4.

Perriman et al., "Circular mRNA can direct translation of extremely long repeating-sequence proteins in vivo." RNA. Sep. 1998;4(9):1047-54.

Petkovic et al., "RNA circularization strategies in vivo and in vitro." Nucleic Acids Res. Feb. 27, 2015;43(4):2454-65.

Pisarev et al., "Ribosomal position and contacts of mRNA in eukaryotic translation initiation complexes." EMBO J. Jun. 4, 2008;27(11):1609-21.

Puttaraju et al., "Generation of nuclease resistant circular RNA decoys for HIV-Tat and HIV-Rev by autocatalytic splicing." Nucleic Acids Symp Ser. 1995;(33):49-51.

Qi et al., "Melting temperature highlights functionally important RNA structure and sequence elements in yeast mRNA coding regions." Nucleic Acids Res. Jun. 2, 2017;45(10):6109-6118.

Ramesh et al., "High-titer bicistronic retroviral vectors employing foot-and-mouth disease virus internal ribosome entry site." Nucleic Acids Res. Jul. 15, 1996;24(14):2697-700.

Rees et al., "Bicistronic vector for the creation of stable mammalian cell lines that predisposes all antibiotic-resistant cells to express recombinant protein." Biotechniques. Jan. 1996;20(1):102-4, 106, 108-10.

Roundtree et al., "Dynamic RNA Modifications in Gene Expression Regulation." Cell. Jun. 15, 2017;169(7):1187-1200.

Rybak-Wolf et al., "Circular RNAs in the Mammalian Brain Are Highly Abundant, Conserved, and Dynamically Expressed." Mol Cell. Jun. 4, 2015;58(5):870-85.

(56) References Cited

OTHER PUBLICATIONS

Salzman et al., "Circular RNAs are the predominant transcript isoform from hundreds of human genes in diverse cell types." PLoS One. 2012;7(2):e30733. 12 pages.
Sanger et al., "Viroids are single-stranded covalently closed circular RNA molecules existing as highly base-paired rod-like structures." Proc Natl Acad Sci USA. Nov. 1976;73(11):3852-6.
Savva et al. "Reprogramming, Circular Reasoning and Self versus Non-self: One-Stop Shopping with RNA Editing." Front Genet. Jun. 7, 2016;7:100., 8 pages.
Schlake et al. "Developing mRNA-vaccine technologies." RNA Biol. Nov. 2012;9(11):1319-30.
Schlee et al., "Recognition of 5' triphosphate by RIG-I helicase requires short blunt double-stranded RNA as contained in panhandle of negative-strand virus." Immunity. Jul. 17, 2009;31(1):25-34.
Sokolova et al., "Chemical reactions within DNA duplexes. Cyanogen bromide as an effective oligodeoxyribonucleotide coupling agent." FEBS Lett. May 9, 1988;232(1):153-5.
Spitale et al., "Structural imprints in vivo decode RNA regulatory mechanisms." Nature. Mar. 26, 2015;519(7544):486-90.
Stein et al., "Translation of vascular endothelial growth factor mRNA by internal ribosome entry: implications for translation under hypoxia." Mol Cell Biol. Jun. 1998;18(6):3112-9.
Tomari et al., "RISC assembly defects in the Drosophila RNAi mutant armitage." Cell. Mar. 19, 2004;116(6):831-41.
Vandivier et al., "The Conservation and Function of RNA Secondary Structure in Plants." Annu Rev Plant Biol. Apr. 29, 2016;67:463-88.
Wang et al., "N6-methyladenosine-dependent regulation of messenger RNA stability." Nature. Jan. 2, 2014;505(7481):117-20.
Warren et al., "Highly efficient reprogramming to pluripotency and directed differentiation of human cells with synthetic modified mRNA." Cell Stem Cell. Nov. 5, 2010;7(5):618-30.
Weingarten-Gabbay et al., "Comparative genetics. Systematic discovery of cap-independent translation sequences in human and viral genomes." Science. Jan. 15, 2016;351(6270):aad4939. 15 pages.
Wesselhoeft et al., "Engineering circular RNA for potent and stable translation in eukaryotic cells." Nat Commun. Jul. 6, 2018;9(1):2629. 10 pages.
Wesselhoeft et al., "RNA Circularization Diminishes Immunogenicity and Can Extend Translation Duration In Vivo." Mol Cell. May 2, 2019;74(3):508-520.e4.
Wu et al., "How RIG-I like receptors activate MAVS." Curr Opin Virol. Jun. 2015;12:91-8.
Xia et al., "CSCD: a database for cancer-specific circular RNAs." Nucleic Acids Res. Jan. 4, 2018;46(D1):D925-D929.
Yang et al., "Extensive translation of circular RNAs driven by N6-methyladenosine." Cell Res. May 2017;27(5):626-641.
Yao et al., "ZKSCAN1 gene and its related circular RNA (circZKSCAN1) both inhibit hepatocellular carcinoma cell growth, migration, and invasion but through different signaling pathways." Mol Oncol. Apr. 2017;11(4):422-437.
Ying et al., "Cancer therapy using a self-replicating RNA vaccine." Nat Med. Jul. 1999;5(7):823-7.
Zarnegar et al., "irCLIP platform for efficient characterization of protein-RNA interactions." Nat Methods. Jun. 2016;13(6):489-92.
Zeng et al., "Reconstitution of the RIG-I pathway reveals a signaling role of unanchored polyubiquitin chains in innate immunity." Cell. Apr. 16, 2010;141(2):315-30.
Zhou et al., "Genome-Wide Maps of m6A circRNAs Identify Widespread and Cell-Type-Specific Methylation Patterns that Are Distinct from mRNAs." Cell Rep. Aug. 29, 2017;20(9):2262-2276.

FIGURE 2B
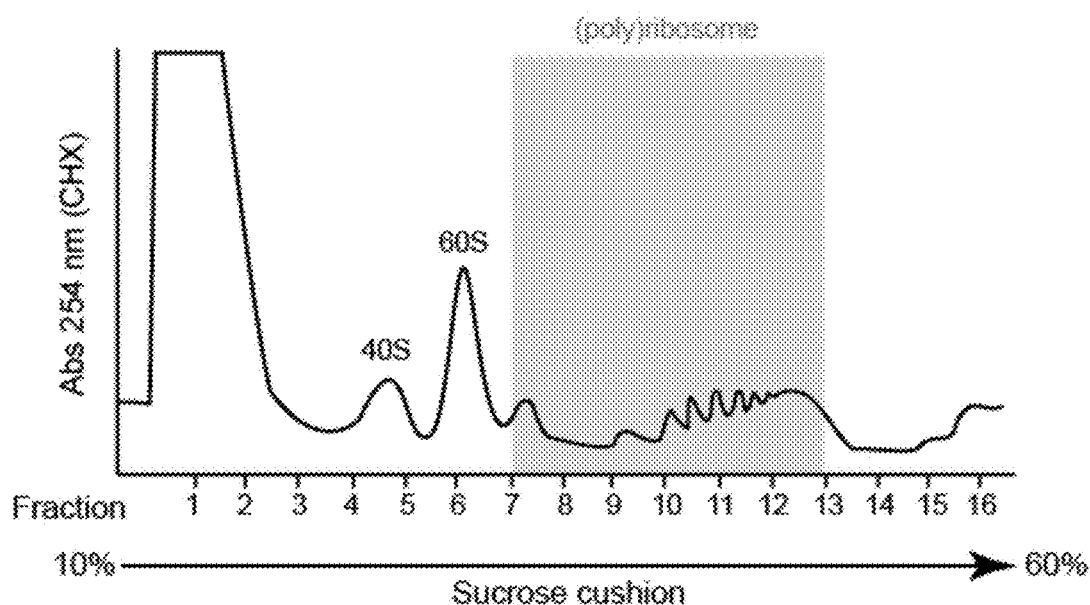
FIGURE 2C
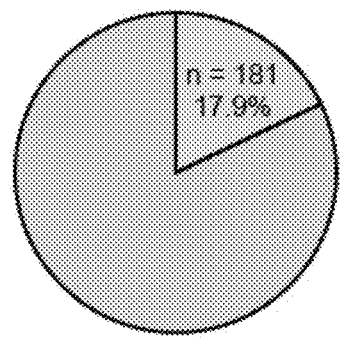
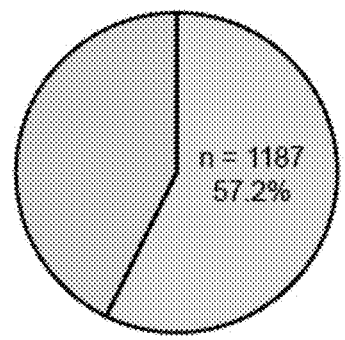
captured eGFP(-) oligos with
eGFP below the 20th percentile
(n=1,010)
captured eGFP(+) oligos with
eGFP above the 80th percentile
(n=2,074)

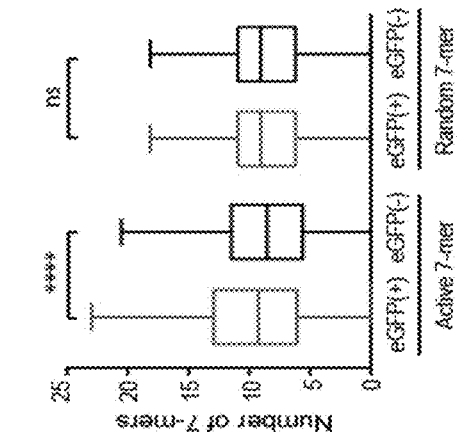
FIGURE 3A
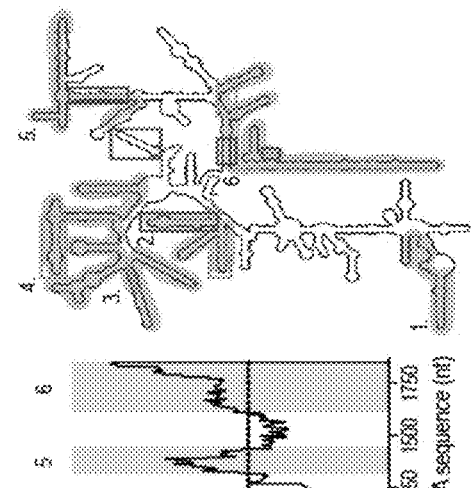
FIGURE 3B
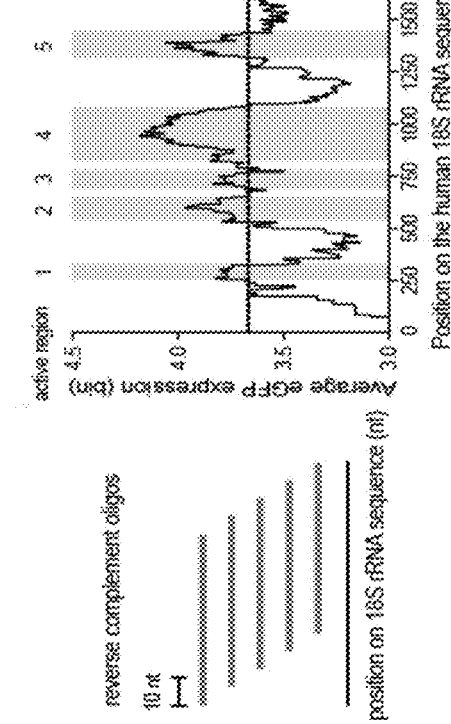
FIGURE 3E
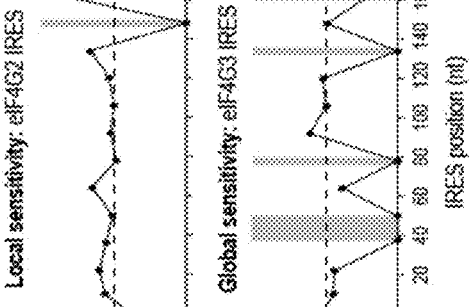
FIGURE 3C
FIGURE 3D
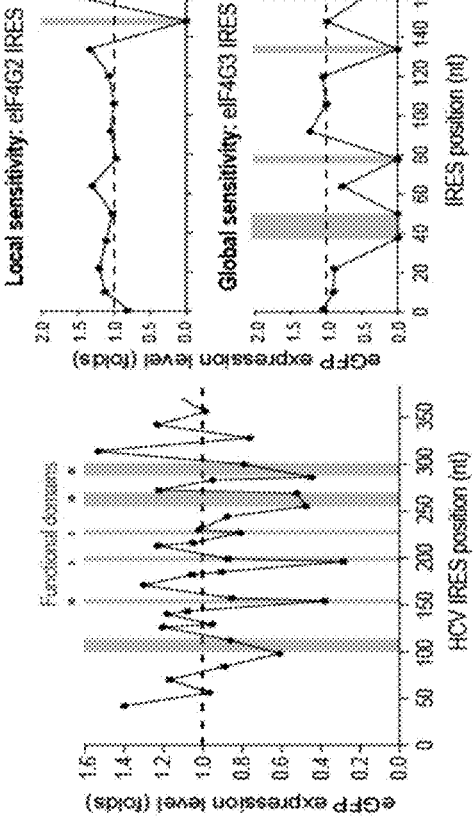
FIGURE 3F
FIGURE 3G
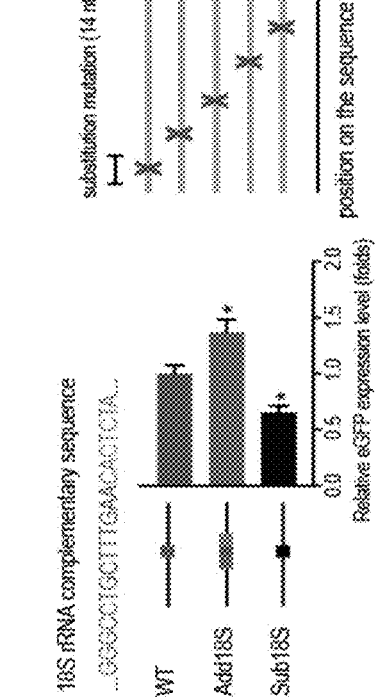
FIGURE 3H

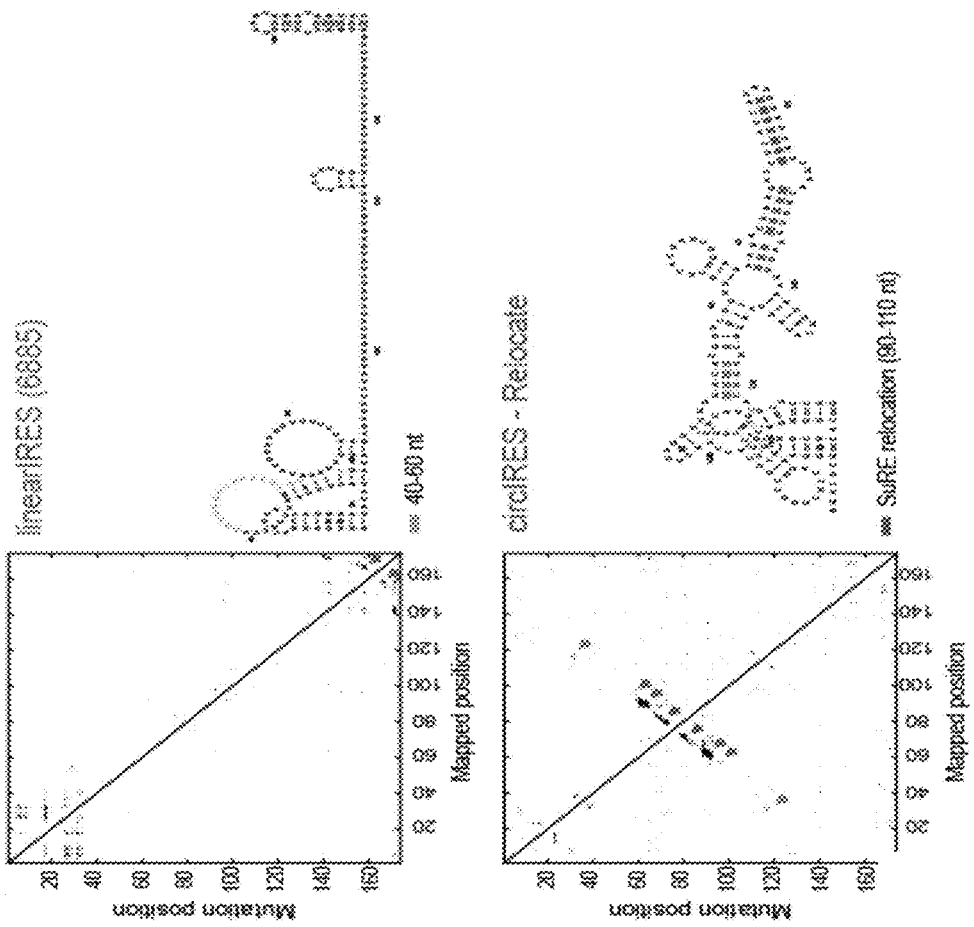
FIGURE 4B
FIGURE 4A
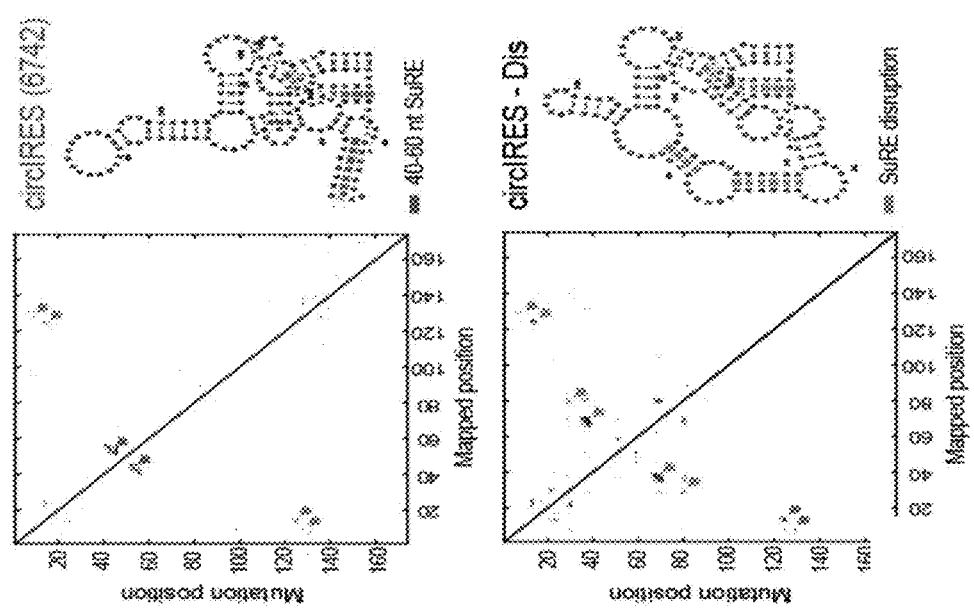
FIGURE 4D
FIGURE 4C

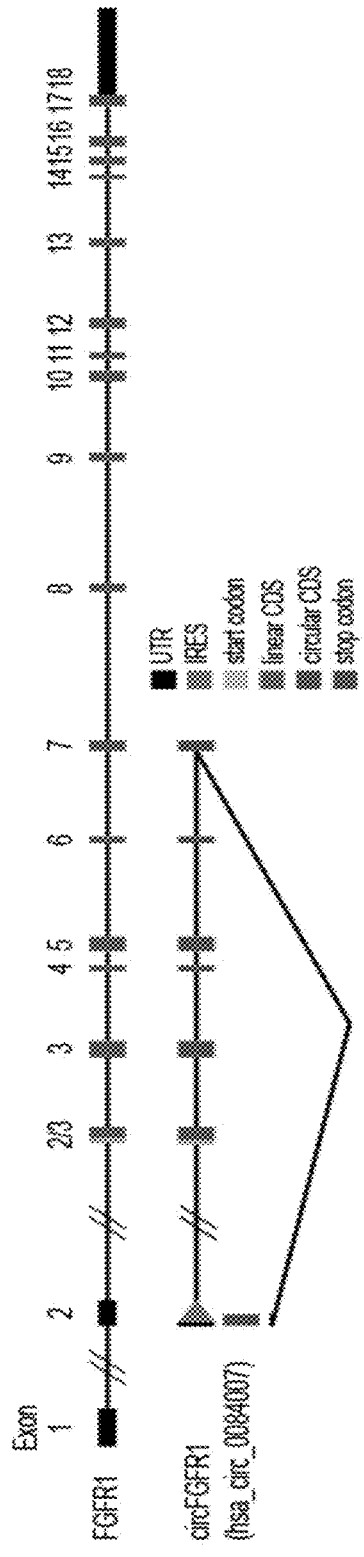
FIGURE 7A
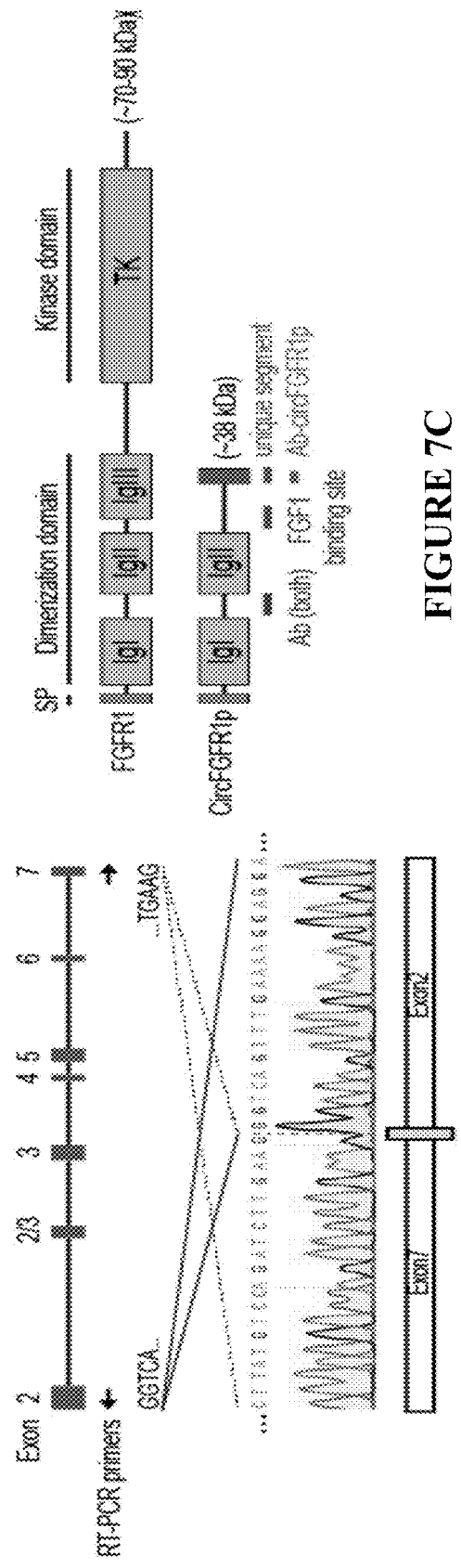
FIGURE 7B
FIGURE 7C

FIGURE 7G
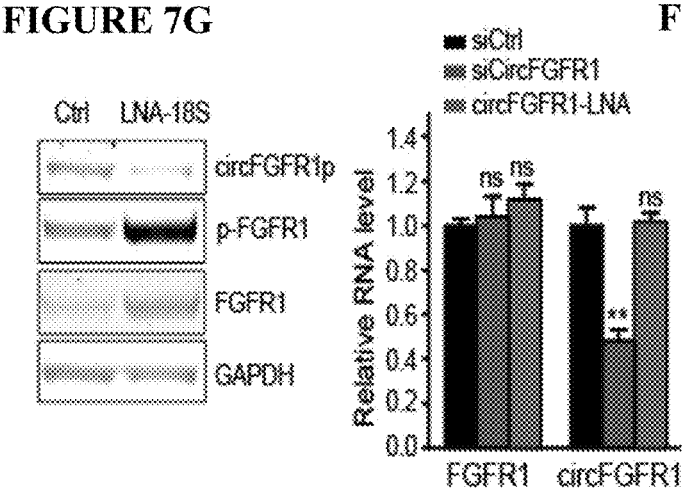
FIGURE 7H
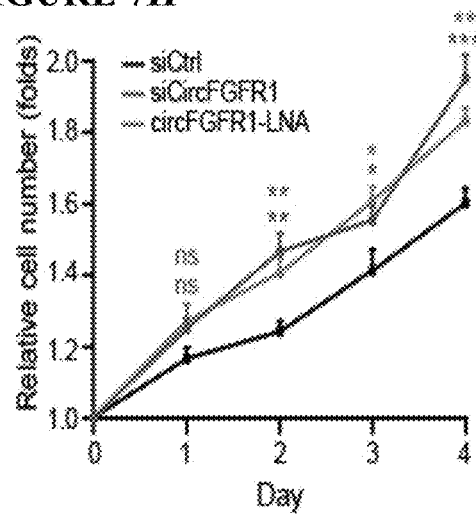
FIGURE 7I
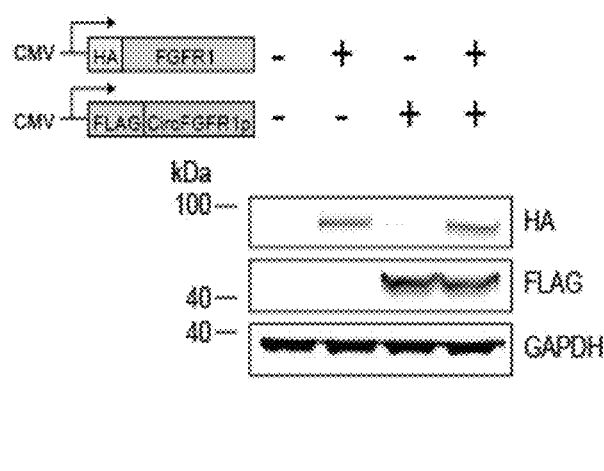
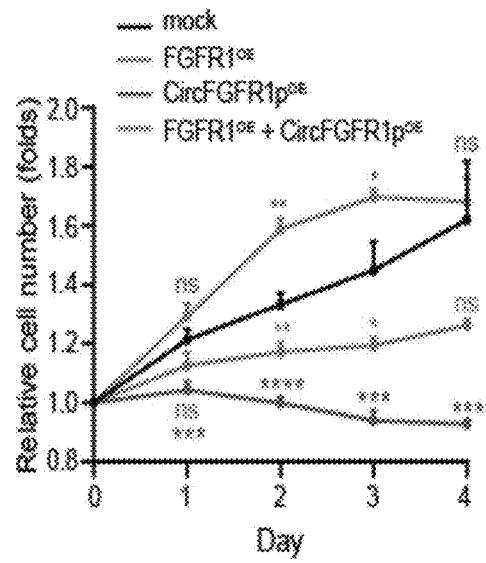

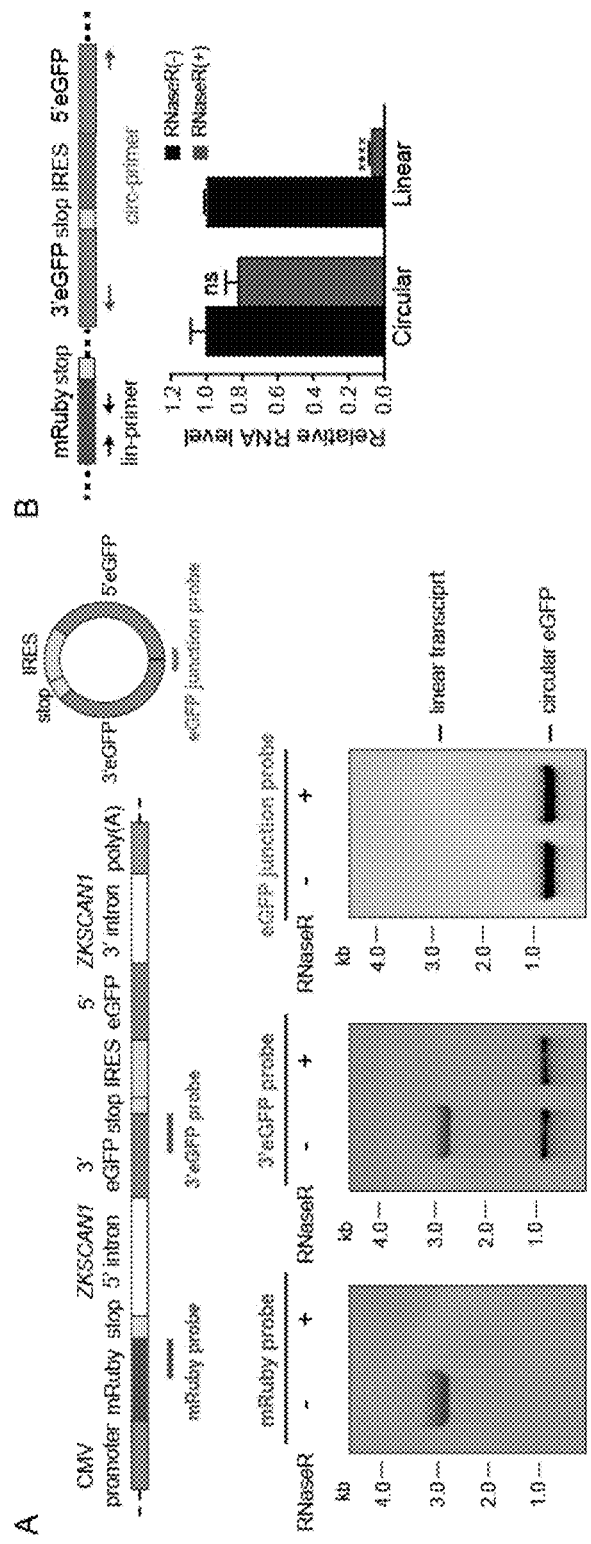

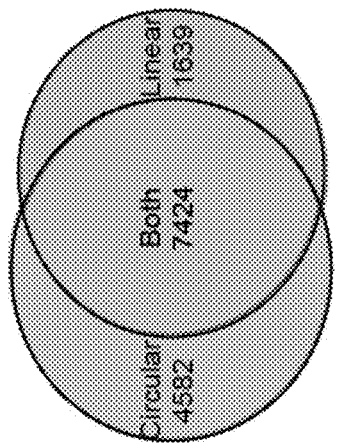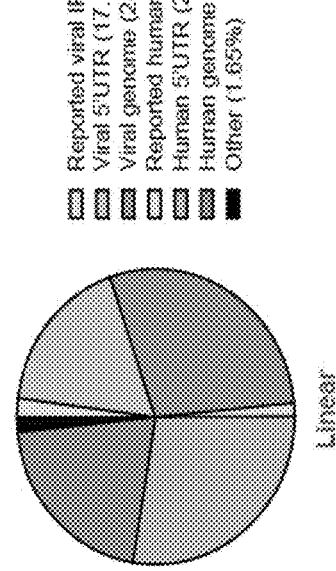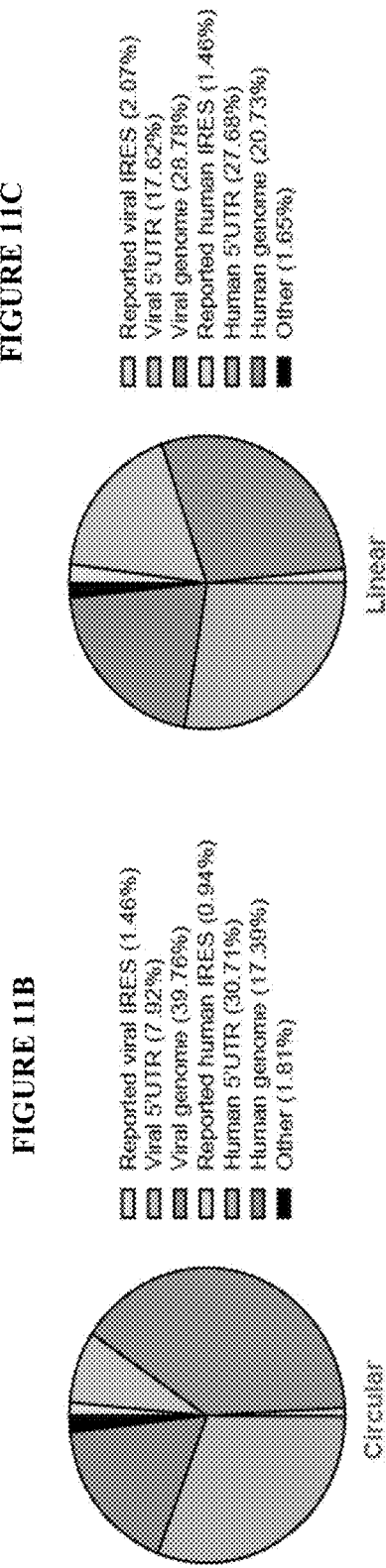

FIGURE 16E
FIGURE 16F
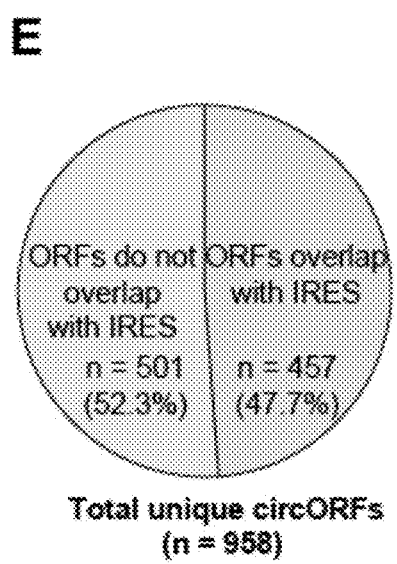
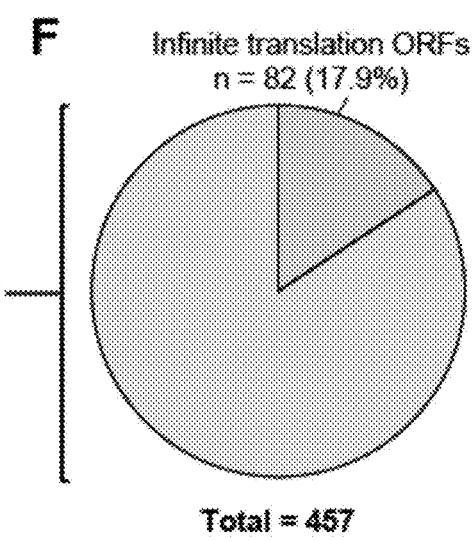

GENETIC ELEMENTS DRIVING CIRCULAR RNA TRANSLATION AND METHODS OF USE

CROSS-REFERENCE TO RELATED APPLICATIONS

This application is a continuation of International Application No. PCT/US2021/039127, filed Jun. 25, 2021, which claims priority to U.S. Provisional Application No. 63/186,507, filed May 10, 2021, and U.S. Provisional Application No. 63/043,964, filed Jun. 25, 2020, the contents of which are herein incorporated by reference in their entireties.

STATEMENT REGARDING FEDERALLY-SPONSORED RESEARCH

This invention was made with Government support under contract CA209919 awarded by the National Institutes of Health. The Government has certain rights in the invention.

SEQUENCE LISTING

The contents of the text file submitted electronically herewith are incorporated herein by reference in its entirety: A computer readable format copy of the Sequence Listing (filename: 38293-303_SeqList_ST25.txt, date created: Jun. 24, 2021, file size: about 12.8 megabytes).

FIELD

The present invention relates to recombinant circular RNA (circRNA) molecules comprising internal ribosome entry sites (IRESs) that contain an RNA secondary structure element and a nucleic acid sequence region complementary to 18S rRNA, as well as methods of use thereof.

BACKGROUND

Over the past decade, results from deep sequencing and computational analysis have suggested that circular RNAs (circRNAs) are a large class of RNAs in mammalian cells that play important roles in various biological processes. Disruption of circRNA expression has been found to be associated with human diseases, such as Alzheimer's disease, diabetes, and cancers. Furthermore, the exceptional stability and cell-specific expression patterns of circRNAs have led to the use of circRNAs as biomarkers for diseases such as cancers, and as indicators of the efficacy of certain treatments. While most of the studies demonstrate that circRNAs function as non-coding RNAs, such as sponges for miRNAs, regulators of mRNA splicing machinery, sequestration of RNA-binding proteins (RBPs), regulators of RBP interaction, and activators of immune responses, emerging evidence suggests that some circRNAs encode peptides and/or proteins and thereby function through these encoded polypeptides. Proteins known to be translated from circRNAs regulate cell proliferation, differentiation, migration, and myogenesis. Dysregulation of circRNA-encoded proteins has been associated with tumorigenesis in certain cancers. Accordingly, circRNA-encoded proteins may be an important link between the class of biologically relevant circRNA and cancer, and perhaps other diseases. Understanding the mechanism of circRNA translation, therefore, may aid in the development of therapeutic methods and/or modalities which exploit circRNA biology and their encoded proteins.

Because circRNA is generated by spliceosome-mediated head-to-tail joining of pre-mRNAs, it does not contain the 5'cap that is commonly known to be required for cap-dependent translation. Thus, circRNA translation utilizes alternate mechanisms to initiate cap-independent translation, such as the use of an internal ribosome entry site (IRES) sequence that is recognized by ribosomes. Introduction of an IRES on synthetically generated circRNAs is sufficient to initiate translation of encoded circRNA proteins, thereby suggesting that endogenous circRNAs harboring IRES sequence may have translation potential as they are exported to the cytoplasm.

Given the rapidly advancing yet nascent state of the art, there remains a need for the identification and characterization of the genetic elements, beyond the presence of an IRES, that can facilitate, initiate, direct or regulate circRNA translation. In particular, there is a need to identify novel IRES sequences that can operably facilitate expression of proteins encoded by circRNAs.

BRIEF SUMMARY OF THE INVENTION

The disclosure provides polynucleotides (e.g., DNA sequences) that encode one or more circular RNA (circRNA) molecules; wherein the circular RNA molecule comprises a payload sequence region (e.g., protein coding or non-coding sequence region) and an internal ribosome entry site (IRES) sequence region operably linked to the payload sequence region. In some embodiments, the IRES comprises: at least one sequence region having an RNA secondary structure element; and a sequence region that is complementary to an 18S ribosomal RNA (rRNA). In some embodiments, the IRES has a minimum free energy (MFE) of less than −18.9 kJ/mol and a melting temperature of at least 35.0° C. Some embodiments of the disclosure include those wherein the RNA secondary structure sequence region or element is formed from the nucleotides at about position 40 to about position 60 of the IRES, wherein the first nucleotide at the 5' end of the IRES is considered to be position 1.

The disclosure also provides polynucleotides (e.g., a DNA sequence) encoding a circular RNA molecule; wherein the circular RNA molecule comprises a protein-coding nucleic acid sequence and an internal ribosome entry site (IRES), wherein the IRES is encoded by any one of the nucleic acid sequences of SEQ ID NO: 1-228 or SEQ ID NO: 229-17201, or a nucleic acid sequence having at least 90% or at least 95% identity or homology thereto over at least 50% of the length of the nucleic acid sequence.

The disclosure also provides recombinant circular RNA molecules comprising a protein-coding nucleic acid sequence region and an internal ribosome entry site (IRES) sequence region operably linked to the protein-coding nucleic acid sequence region, wherein the IRES comprises: at least one sequence region having secondary structure element; and a sequence region that is complementary to an 18S ribosomal RNA (rRNA); wherein the IRES has a minimum free energy (MFE) of less than −18.9 kJ/mol and a melting temperature of at least 35.0° C. In some embodiments, the protein-coding nucleic acid sequence region is operably linked to the IRES in a non-native configuration.

The disclosure also provides recombinant circular RNA molecules comprising a protein-coding nucleic acid sequence region and an internal ribosome entry site (IRES) sequence region operably linked to the protein-coding nucleic acid sequence; wherein the IRES is encoded by any one of the nucleic acid sequences listed in of SEQ ID NO:

1-228 or SEQ ID NO: 229-17201, or a nucleic acid sequence having at least 90% or at least 95% homology or identity thereto. In some embodiments, the protein-coding nucleic acid sequence region is operably linked to the IRES in a non-native configuration.

Also provided are methods of producing a protein in a cell using the aforementioned recombinant circular RNA molecules, or polynucleotides (e.g., DNA molecules) encoding the same.

Also provided are as vectors comprising the aforementioned recombinant circular RNA molecules, or DNA molecules encoding the same.

Also provided are host cells comprising the aforementioned recombinant circular RNA molecules, or DNA molecules encoding the same.

Also provided are compositions comprising (i) a DNA sequence encoding a circular RNA, and (ii) a non-coding circular RNA or a DNA sequence encoding the same.

Also provided are methods for delivering a non-coding circular RNA to a cell, the methods comprising contacting the cell with a composition comprising a DNA sequence encoding a circular RNA, and (ii) a non-coding circular RNA or a DNA sequence encoding the same, thereby delivering the non-coding circular RNA to the cell.

The disclosure further provides an oligonucleotide comprising a nucleic acid sequence region that hybridizes to an internal ribosome entry site (IRES) sequence region present on a circular RNA molecule and upon hybridization inhibits translation of the coding sequence region of the circular RNA molecule. Also provided is a method of inhibiting translation of a protein-coding nucleic acid sequence region (e.g., payload) of a circular RNA molecule using the aforementioned oligonucleotide.

These and other embodiments will be explained in further detail below, and in the appended drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A provides a schematic overview of the high-throughput split-eGFP circRNA reporter screening assay for identifying circRNA IRES. A synthetic oligo library containing 55,000 oligos was cloned into a split-eGFP circRNA reporter. Since the full-length eGFP will only be reconstituted when back-spliced into the circRNA, the eGFP fluorescence signal can only come from the cap-independent translation activity driven by the inserted oligos on the circRNA. The eGFP(+) cells were sorted into seven expression bins by their eGFP fluorescence intensity with FACS. The number of reads for each synthetic oligo within each bin was determined by next-generation DNA sequencing. The final eGFP expression for each synthetic oligo was quantified by the mean weighted bin number according to the distribution of the number of reads across seven expression bins from two independent biological replicates. Shown in FIG. 1B is the eGFP expression distribution of 40,855 captured synthetic oligos. eGFP(+) oligos were defined as the oligos with eGFP expression higher than the background eGFP threshold (the eGFP expression of no-oligo-inserted eGFP circRNA reporter). The pie chart represents the composition of different oligo categories among eGFP(+) oligos. Shown in FIG. 1C is quantification of the percentage of captured eGFP(+) oligos among the oligos originated from the sequences of the reported IRES, viral 5' UTR, or human 5' UTR in the screening assay. Shown in FIG. 1D is identification of circular and linear RNA specific IRESs. Normalized eGFP expression (log 10) is shown for each captured oligo in the screening assay performed on the circular RNA (described herein) or the linear RNA (Weingarten-Gabbay et al., 2016)) screening system utilizing the same synthetic oligo library. Circular IRESs (green circles) or linear IRESs (blue circles) were identified by comparing the IRES activity of the oligos that were detected only in either circular or linear RNA screening system, respectively. Red dashed lines represent the normalized eGFP expression threshold.

FIG. 2A-2E show that circRNAs containing an eGFP(+) oligo have higher cap-independent translation activity. FIG. 2A shows a schematic overview of the circRNA polysome profiling method for capturing translated circRNAs. FIG. 2B shows (poly)ribosome fractionations of cells transfected with split-eGFP circRNA reporter containing the synthetic oligo library followed by cycloheximide (CHX) treatment. Fractions 7 to 12 (shaded in blue) were determined as (poly)ribosome fractions according to the Abs254 pattern. Shown in FIG. 2C is quantification of the percentage of (poly)ribosome-enriched oligos among the captured eGFP (−) oligos with eGFP expression below the 20th percentile or the eGFP(+) oligos with eGFP expression above the 80th percentile, respectively. FIG. 2D provides sequencing reads from Ribo-seq and QTI-seq plotted on the genes showing eGFP(+) oligos harboring aTIS (top), nTIS (middle), and dTIS (bottom) with overlapped annotated circRNAs (brown segments). FIG. 2E shows quantification of the percentage of eGFP(−) or eGFP(+) oligos harboring no TIS (TIS(−)) (left) or more than one TIS (TIS(+)) (right), and the percentage of aTIS, nTIS, or dTIS oligos among eGFP(+)/TIS (+) oligos.

FIG. 3A-3J shows that the 18S rRNA complementary sequence on the IRES facilitates circRNA cap-independent translation activity. Provided in FIG. 3A is a schematic of the sliding-window design of synthetic oligos for mapping the active regions on the human 18S rRNA. FIG. 3B shows quantification of the mean eGFP expression of the synthetic oligos overlapped with the corresponding position across the human 18S rRNA. The dashed line indicates the background eGFP expression. The identified active regions on the 18S rRNA are shaded in green. FIG. 3C provides an illustration of the secondary structure of human 18S rRNA showing the identified active regions and reported RNA contact regions on the 18S rRNA. The identified active regions 1 to 6 are shaded in green. Boxes outlined the regions on the 18S rRNA that have been reported to contact with mRNA (red) or IRES RNA (orange). FIG. 3D shows quantification of the number of the 18S rRNA active 7-mers or the random 7-mers harbored by eGFP(+) or eGFP(−) oligos plotted on a Tukey box-plot (outliers not shown). Ns: not significant; ****: p-value <0.001 by an unpaired two-sample t-test. Shown in FIG. 3E is quantification of the IRES activity for the oligo with higher or lower 18S rRNA complementarity determined by FACS (MFIeGFP/mRuby). *: p-value <0.05 relative to the wild-type (WT) oligo by an unpaired two-sample t-test (n=4-6 independent replicates). Error bar: SEM. FIG. 3F provides a schematic of the design of synthetic oligos for systematic scanning mutagenesis. FIG. 3G shows the eGFP expression of each oligo containing the random substitution mutation at the corresponding position on the HCV IRES. The black dot represents the start position of each mutation on the IRES. The identified essential elements are shaded in blue. The red lines represented the functional domains on the HCV IRES that have been reported. The eGFP expression for each oligo was normalized to the mean eGFP expression of all the oligos on the HCV IRES. In FIG. 3H, examples are provided of circRNA IRES with local and global sensitivity identified by scanning mutagenesis. The identified essential elements on the IRES are shaded in blue. In FIG. 3I, the mean eGFP expression of all the circRNA IRES oligos with global sensitivity is shown at each mutation position across the IRES. The regions harboring regulatory elements were shaded in different colors (blue: 5-15 nt and 135-165 nt; red: 40-60 nt). Shown in FIG. 3J is quantification of the local MFE in a 15 nucleotide (nt) sliding window on the IRES. The regions harboring regulatory elements were shaded in different colors (blue: 5-15 nt and 135-165 nt; red: 40-60 nt).

FIG. 4A-4K shows that a distinct SuRE at 40-60 nucleotide (nt) position on the IRES can facilitate circular IRES activity. FIG. 4A-4H show the secondary structure of the mutated IRESs (SEQ ID NOs: 33925-33932) determined by M2-seq. The arrowheads indicate the high-confidence secondary structure identified by M2-net; the corresponding positions are labeled with the same color on the RNA structure panel. Red arrowheads indicate the SuRE at the 40-60 nt position on the circular IRES. CircIRES-dis: circular IRES with the SuRE disrupted by sequence substitution. CircIRES-relocate: Circular IRES with the SuRE relocated to 90-110 nt region. CircIRES-single and circIRES-comp: circular IRES with single complementary mutations and compensatory double complementary mutations, respectively. circIRES-BoxB: circular IRES with the SuRE substituted by BoxB stem-loop. linearIRES-add: linear IRES with 40-60 nt region substituted by the SuRE at the 40-60 nt position on the circular IRES. Shown in FIG. 4I is quantification of the IRES activity for each mutated IRES determined by FACS (MFIeGFP/mRuby). The activity of each permuted IRES was normalized to the linear IRES. Ns: not significant; : p-value <0.01, **: p-value <0.001 relative to the linear IRES by an unpaired two-sample t-test (n=4-6 independent replicates). Error bar: SEM. Shown in FIG. 4J is quantification of the percentage of the eGFP(+) oligos (left) and endogenous translated circRNAs (right) harboring 18S rRNA complementarity or the SuRE element. FIG. 4K provides an illustration of two key regulatory elements, complementary 18S rRNA sequence and the SuRE at 40-60 nt position on the IRES, facilitating circRNA cap-independent translation.

FIG. 5A shows a schematic of disrupting the key regulatory elements on the IRES of the oligo-split-eGFP-circRNA reporter by co-transfecting the anti-sense LNAs targeting specific regions on the IRES. LNA-18S: the LNA targeting the 18S rRNA complementary sequence on the IRES; LNA-SuRE: the LNA targeting the SuRE at the 40-60 nt position on the IRES; LNA-Rnd: the LNA targeting the random position downstream of LNA-18S or LNA-SuRE on the IRES. Shown in FIG. 5B is quantification of the normalized eGFP fluorescence signal intensity of the cells co-transfected with the corresponding LNA and the oligo-split-eGFP-circRNA reporter carrying the corresponding IRES. The number represents the index number of the oligo. Ns: not significant; *: p-value <0.05; : p-value <0.01, *: p-value <0.005 relative to the mock transfection by an unpaired two-sample t-test (n=3-5 independent replicates). Error bar: SEM. Provided in FIG. 5C is a schematic of QTI-qRT-PCR quantification of the level of translation-initiating endogenous circRNAs. FIG. 5D shows quantification of the translation-initiating RNA level of the human endogenous circRNAs containing the corresponding IRES upon disrupting the IRES by the corresponding LNA transfection. The circRNA level was normalized to the GAPDH mRNA. Ns: not significant; *: p-value <0.05; : p-value <0.01, *: p-value <0.005 relative to the mock transfection by an unpaired two-sample t-test (n=4-6 independent replicates). Error bar: SEM. Shown in FIG. 5E are images of western blots showing the level of protein produced from the endogenous circRNAs upon IRES disruption by the transfection of the corresponding LNA.

FIG. 6A shows quantification of the percentage of IRES-mapped human endogenous circRNAs harboring one or more eGFP(+) oligo sequences (IRES(+) circRNA), or no eGFP(+) oligo sequences (IRES(−) circRNA). FIG. 6B shows quantification of the distribution of the parent genes among IRES(+) circRNAs. Each part of the pie chart represents a different gene. FIG. 6C shows quantification of the percentage of potential cancer-associated IRES(+) circRNAs from the CSCD. Provided in FIG. 6D is a histogram showing the distribution of the number of IRES harbored by each individual IRES(+) circRNA (capped at n=20). FIG. 6E is a histogram showing the distribution of the number of mapped circRNA for each individual eGFP(+) oligo (capped at n=20). FIG. 6F shows the top 12 represented biological processes from GO term analysis that are enriched in the parent genes of IRES(+) circRNAs. Provided in FIG. 6G is a schematic of generating the putative endogenous circORF list. FIG. 6H shows the top 15 represented conserved motifs from Pfam analysis that are enriched in the predicted circRNA-encoded polypeptides. FIG. 6I shows a schematic of peptidomic validation of the putative circORFs. Provided in FIG. 6J is a heat map showing the number of unique tryptic polypeptides detected in the peptidomic dataset of each MS captured circORF. Shown in FIG. 6K are the MS1 and MS2 spectra of a representative tryptic BSJ polypeptide (SEQ ID NO: 33933) captured from circORF_575. FIG. 6L shows the representative MS2 spectra and the top 3 rank PRM-MS transition ions spectra of the spike-in heavy isotope labeled polypeptide (top right (SEQ ID NO: 33934)) and the sample tryptic polypeptide (bottom right (SEQ ID NO: 33934)) from circORF_19. [V]: heavy isotope labeled valine (13C5, 15N; +6 Da).

FIG. 7A-7L show that circRNA-encoded circFGFR1p suppresses cell proliferation under stress conditions. FIG. 7A provides is a schematic of the CDS of FGFR1 and circFGFR1 transcript. Shown in FIG. 7B is a schematic of the design of junctional RT-PCR primers (black arrows) and the Sanger sequencing results detecting the back-splicing junction (yellow box) of circFGFR1 (SEQ ID NO: 33935). FIG. 7C provides is a schematic of the conserved motifs on FGFR1 and circFGFR1p. Ab (both): the antibody which can detect both FGFR1 and circFGFR1p. Ab-circFGFR1p: custom circFGFR1p antibody. The blue lines indicate the location of the antigen peptide for each antibody. FIG. 7D shows a schematic of the polypeptides captured by IP-LC-MS.MS (underline) that matched the circFGFR1p unique region (red) and the region overlapped with FGFR1 (black) using a custom antibody against the unique region of the circFGFR1p (in bold) (circFGFR1p (SEQ ID NO: 33902); circFGFR1p fragment (SEQ ID NO: 33936)). The extracted region (~30-45 kDa) on the coomassie blue stained SDS-PAGE gel is outlined in red box. Shown in FIG. 7E are the representative MS2 spectra and the top 3 rank PRM-MS transition ions spectra of the spike-in heavy isotope labeled polypeptide (top (SEQ ID NO: 33937)) and the BJ tryptic polypeptide (bottom (SEQ ID NO: 33937)) of circFGFR1p. [L]: heavy isotope labeled leucine (13C6, 15N; +7 Da). FIG. 7F provides are images of FGFR1(red), circFGFR1p (green) and DAPI (blue) in HEK-293T cells co-transfected with plasmids expressing HA-FGFR1 and FLAG-circFGFR1p without permeabilization. Scale bars: 10 micrometers. Shown in FIG. 7G are western blots showing circFGFR1p and FGFR1 protein level (Ab-both), and the quantification of FGFR1 and circFGFR1 RNA level by qRT-PCR of cells transfected with siRNA or LNA. siCtrl: non-targeting siR-NAs; siCircFGFR1: circFGFR1 specific siRNAs; circFGFR1-LNA: anti-sense LNA oligo targeting the 18S rRNA complementary sequence on the circFGFR1 IRES. P-FGFR1: phosphorylated FGFR1. Ns: not significant; ** p-value <0.01 relative to the siCtrl by an unpaired two-sample t-test (n=3 independent replicates). Error bar: SEM. (FIG. 7H) Shown is quantification of cell proliferation in cells with the knockdown of circFGFR1 RNA (si-CircFGFR1) or circFGFR1p (circFGFR1-LNA) from day 1 to 4 with FGF1 addition. * p-value <0.05;  p-value <0.01; * p-value <0.005 relative to the siCtrl by an unpaired two-sample t-test (n=3-5 independent replicates). Error bar: SEM. Provided in FIG. 7I are images of a western blot showing the cells with FGFR1, circFGFR1p, or FGFR1+ circFGFR1p overexpression (left panel) and their corresponding cell proliferation from day 1 to 4 with FGF1 addition (right panel). Ns: not significant; * p-value <0.05,  p-value <0.01, ** p-value <0.001 relative to the mock transfection by an unpaired two-sample t-test (n=4-6 independent replicates). Error bar: SEM.

FIG. 7J provides images of western blots showing FGFR1 protein and circFGFR1p level with or without the heat-shock. FIG. 7K shows quantification of the Western blot of circFGFR1p protein level relative to FGFR1 (all isoforms) under normal (WT) and the heat-shock (HS) condition. Error bar: SEM from three independent blots. * p-value <0.05 relative to the WT by an unpaired two-sample t-test (n=3 independent blots). Shown in FIG. 7L is quantification of the Western blot showing the change of the protein level of FGFR1 and circFGFR1p under the heat-shock condition. Protein level is normalized to the GAPDH protein loading control of each condition. Error bar: SEM from three independent blots. Ns: not significant; * p-value <0.05 relative to 1 by a one-sample t-test (n=3 independent blots).

FIG. 8A-8C show that the oligo-split-eGFP-circRNA reporter construct does not generate eGFP signal from trans-splicing. FIG. 8A shows images of northern blots of IRES-split-eGFP circRNA reporter transfected and mRuby (+)/eGFP(+) sorted cells using probes against the mRuby, 3'eGFP, and the eGFP back-splicing junction region on the reporter transcript with or without RNase R treatment. Shown in FIG. 8B is quantification of the RNA level of the eGFP circRNA or the mRuby linear transcript in the IRES-split-eGFP circRNA reporter transfected and mRuby(+)/ eGFP(+) sorted cell total RNA with RNase R treatment relative to the RNaseR (−) samples. The level of RNA was normalized to the GAPDH mRNA level in each sample. Error bar: SEM. Ns: not significant; ****: p-value <0.001 relative to the RNase R(−) sample by an unpaired two-sample t-test (n=3 independent replicates). Error bar: SEM. FIG. 8C illustrates flow cytometry analysis of eGFP(+) cells upon transfected with corresponding reporter constructs. eGFP(+) cells were gated according to the cells with mock transfection.

FIG. 9A provides a reproducibility measurement of the eGFP expression for each captured oligo of two independent biological replicates from the screening assay. Only the oligos recovered in both replicates were included in the analysis. The R represents the Pearson's correlation coefficient. Provided in FIG. 9B is a schematic of the primers design to quantify the expression level of linear and circular transcripts of the reporter construct. The divergent circular primers spanning the back-splicing junction of circRNA should detect circular transcripts only. FIG. 9C shows quantification of circularization efficiency by qRT-PCR of seven randomly picked clones transfected oligo-split-eGFP reporter plasmid. The circularization efficiency was calculated by normalizing the expression level of the circular transcripts to the expression level of the linear transcripts. The number indicates the index of the oligo. No-IRES: no-IRES-inserted reporter plasmid. Ns: not significant relative to the empty circRNA by an unpaired two-sample t-test (n=3 independent replicates). Error bar: SEM. FIG. 9D illustrates the distribution of the fraction of reads across all 7 bins of cells transfected with IRES-split-eGFP circRNA reporter carrying no-IRES (background eGFP expression), or the oligo showing high (oligo #25674), moderate (oligo #26338) or no (oligo #26961) cap-independent translation activity. The black line represents the polynomial trend line of the distribution. FIG. 9E provides images of western blots showing the expression level of eGFP, Cre, and CD4 from the split-eGFP circRNA reporter containing no-IRES or the corresponding IRES. The number indicates the index of the oligo. Provided in FIG. 9F are images of a western blot showing eGFP expression level of the cap-dependent translated linear RNA (CMV promoter driven) and the cap-independent translated circRNA (IRES driven; oligo #8788).

FIG. 11A-11D show the IRES composition among the captured linear and circular IRES. FIG. 11A provides a Venn diagram representing the number of circular and linear specific IRES by comparing the results from the study (circular RNA system) with the results from the study described in Weingarten-Gabbay et al., Science 351, aad4939 (2016) (linear RNA system). Shown in FIG. 11B-11C is the composition of the captured viral and human IRES in the circular IRES (FIG. 11B), the linear IRES (FIG. 11C), and the IRES showing cap-independent translation activity in both the linear and circular RNA system (Both) (FIG. 11D).

FIG. 12A shows 40S and (poly)ribosome fractions of cells transfected with split-eGFP reporter containing the synthetic oligo library and treated with puromycin (PMY; left panel) or cycloheximide (CHX; right panel) followed by sucrose gradient fractionation. FIG. 12B shows quantification of the ratio of the eGFP circRNA level relative to the mRuby linear transcript level of the IRES-split-eGFP circRNA reporter transfected and mRuby(+)/eGFP(+) sorted cell total RNA with RNase R treatment in a time-course manner (20 U RNase R per 20 μg of RNA). Error bar: SEM. Shown in FIG. 12C is quantification of the fraction of the number of total reads of the captured oligos in 40S and (poly)ribosome fraction with PMY or CHX treatment. FIG. 12D provides the number of captured eGFP(−) and eGFP(+) oligos before and after the RNase R treatment. FIG. 12E shows the normalized number of reads of total captured oligos with RNase R treatment and captured oligos in the poly(ribosome) fraction.

FIG. 13C shows the percentage of the number of active 7-mers on each position on the oligo among all eGFP(+) oligos. FIG. 13D shows the cumulative frequency distribution of number of the RRACH motif on the eGFP(+) and eGFP(−) oligos. Ns: not significant by Kolmogorov-Smirnov cumulative distribution test.

FIG. 14B shows cumulative frequency distribution of number of canonical translation start codon (ATG) on the circular and linear IRESs. Ns: not significant by Kolmogorov-Smirnov cumulative distribution test. Shown in FIG. 14C is cumulative frequency distribution of number of m6A motif (RRACH, SEQ ID NO: 3394) on the circular and linear IRESs. Ns: not significant by Kolmogorov-Smirnov cumulative distribution test. Shown in FIG. 14D is quantification of number of Kozak sequence (ACCATGG, SEQ ID NO: 33945) on the circular and linear IRESs. Ns: not significant by an unpaired two sample t-test. Error bar: SEM. FIG. 14E shows quantification of the IRES activity of the oligo in the circular RNA reporter (left) and linear RNA reporter (right), respectively. The IRES activity was determined with FACS by normalizing the eGFP medium fluorescence intensity driven by the oligo (MFIeGFP) to the linear RNA expression level of the reporter construct determined by the mRuby medium fluorescence intensity (MFImRuby). The value was further normalized to the oligo-6472. Ns: not significant, *: p-value <0.05, ***: p-value <0.005, * ***: p-value <0.001 relative to oligo-6742 by an unpaired two-sample t-test (n=4-6 independent replicates). Error bar: SEM. FIG. 14F-14G show the secondary structure of example circular IRESs (SEQ ID NOs: 33938-33940) and linear IRESs (SEQ ID NOs: 33941-33943) (three IRESs for each) determined by M2-seq. The arrowheads indicate the high confident secondary structure identified by M2-net; the corresponding positions are labeled with the same color on the RNA structure panel. Red arrowheads indicate the SuRE at the 40-60 nt position on the circular IRESs.

FIG. 15A shows quantification of the eGFP circRNA level relative to the mRuby linear transcript level of the cells co-transfected with the corresponding LNA and the oligo-split-eGFP-circRNA reporter carrying the corresponding IRES. Ns: not significant; *: p-value <0.05 relative to the mock transfection by an unpaired two-sample t-test (n=4-6 independent replicates). Error bar: SEM. Shown in FIG. 15B is quantification of the human endogenous circRNA level harboring the corresponding IRES upon disrupting the IRES by the corresponding LNA transfection. The circRNA level was normalized to the GAPDH mRNA. Ns: not significant relative to the mock transfection by an unpaired two-sample t-test (n=4-6 independent replicates). Error bar: SEM.

FIG. 16A-16L show identification of putative endogenous circRNA-encoded polypeptides. FIG. 16A shows quantification of the percentage of all endogenous human circRNAs harboring no oligo sequences, no eGFP(+) oligo sequences, or one or more eGFP(+) oligo sequences. Provided in FIG. 16B is a histogram showing the distribution of the number of IRESs harbored by each individual IRES(+) circRNA (capped at n=20) among the circRNAs generated from the 159 transcripts for which oligos were designed tiling across the entire transcripts. Provided in FIG. 16C is a histogram showing the distribution of the number of mapped circRNAs for each individual eGFP(+) oligo (capped at n=20) among the circRNAs generated from the 159 transcripts for which oligos were designed tiling across the entire transcripts. Shown in FIG. 16D is the distribution of the distance from the back-splicing junction to the mapped IRES on each circRNA (capped at nt=2000). The distance is calculated from the back-splicing junction to the first mapped nucleotide of the IRES. GC matched oligo: the RNA sequence on the circRNA with the same length and GC-content as the mapped IRES. The distance of GC matched oligo was determined on each IRES-mapped circRNA by taking the average distance from the back-splicing junction to all the GC matched oligos on the circRNA. FIG. 16E illustrates quantification of the percentage of circRNA-encoded polypeptide with the ORF overlapping the IRES region on the circRNA. Shown in FIG. 16F is quantification of the percentage of circRNA-encoded polypeptide with infinite recursive ORF on circRNA among IRES-overlapping ORFs. FIG. 16G shows an image of a Western blot showing infinite recursive eGFP translation of cells transfected with the split-eGFP circRNA reporter containing an in-frame IRES (oligo-2007). FIG. 16H provides a histogram showing the size distribution of predicted circRNA-encoded polypeptides. Shown in FIG. 16I is quantification of the percentage of circORFs with matched sORFs using the mapped IRES ORF analysis method or traditional ORF analysis method. Shown in FIG. 16J is quantification of the percentage of the circRNAs identified by peptidomics that contain at least one RFP fragment uniquely overlapping with the back-splicing junction. Shown in FIG. 16K is the percentage of the coverage of MS-20 identified polypeptides on each protein with different expression level in human iPSCs. The MS profiling data was obtained and mapped as described in Chen et al. (2020). FIG. 16L shows is the MS-identified polypeptide coverage on a lowly expressed EGFR protein in human iPSCs. The red boxes represent the mapped position of the MS-identified polypeptides on the protein.

FIG. 17A shows the H3K4me3 level obtained from ENCODE on the genomic region of FGFR1 and circFGFR1 showing no enrichment of the promoter signature near circFGFR1 IRES. FIG. 17B provides are images of FGFR1(red), circFGFR1p (green) and DAPI (blue) in HEK-293T cells co-transfected with plasmids expressing FGFR1 and FLAG-circFGFR1p with permeabilization. Scale bars: 10 micrometers. Shown in FIG. 17C is quantification of the expression level of circFGFR1 in tumor samples and normal adjacent samples plotted as Tukey box-plot (outliers not shown). The data was extracted from the TCGA analysis without filtering (Nair et al., Oncotarget 7, 80967, (2016)). ERBC: estrogen receptor positive breast cancer; TNBC: triple-negative breast cancer. Shown in FIG. 17D is quantification of the expression level of circFGFR1 in non-transformed cell lines and cancer cell lines plotted as Tukey box-plot. The data was extracted from the CSCD database (Xia et al., 2018). FIG. 17E shows quantification of circFGFR1 IRES activity with or without heat-shock. Ns: not significant relative to the normal condition (WT) by an unpaired two-sample t-test (n=3 independent replicates). Error bar: SEM. Shown in FIG. 17F is quantification of the relative circularization efficiency of circFGFR1 RNA under normal or the heat-shock (HS) condition with qRT-PCR by normalizing the circFGFR1 RNA level to the linear FGFR1 RNA level using linear and circular RNA specific primers respectively. Ns: not significant relative to the normal condition by an unpaired two-sample t-test (n=3 independent replicates). Shown in FIG. 17G is quantification of the circFGFR1 RNA level by qRT-PCR with or without heat-shock (normalized to GAPDH mRNA level). Ns: not significant relative to the normal condition by an unpaired two-sample t-test (n=3 independent replicates). Provided in FIG. 17H is a schematic showing that, under normal conditions, upon FGF addition, FGFR1 undergoes dimerization and autophosphorylation, activating the downstream cell signaling pathway and facilitating cell proliferation. FIG. 17I provides is a schematic showing that, under stress conditions, the translation of FGFR1 RNA is downregulated, resulting in low FGFR1 protein level, where the cap-independent translation activity of circFGFR1 IRES remains steady. Upon FGF addition, circFGFR1p dimerizes with FGFR1. However, since circFGFR1p lacks the autophosphorylation domain, the circFGFR1p-FGFR1 dimer cannot activate the downstream cell signaling pathway, resulting in the suppression of cell proliferation.

FIG. 18A shows MFEs for all viral IRES positive oligos in DNA format and all human IRES positive oligos in DNA format. Provided in FIG. 18B is a histogram showing eGFP expression levels driven by representative viral IRESs from DNA-based IRES screen.

DETAILED DESCRIPTION OF THE INVENTION

Figure 1A:
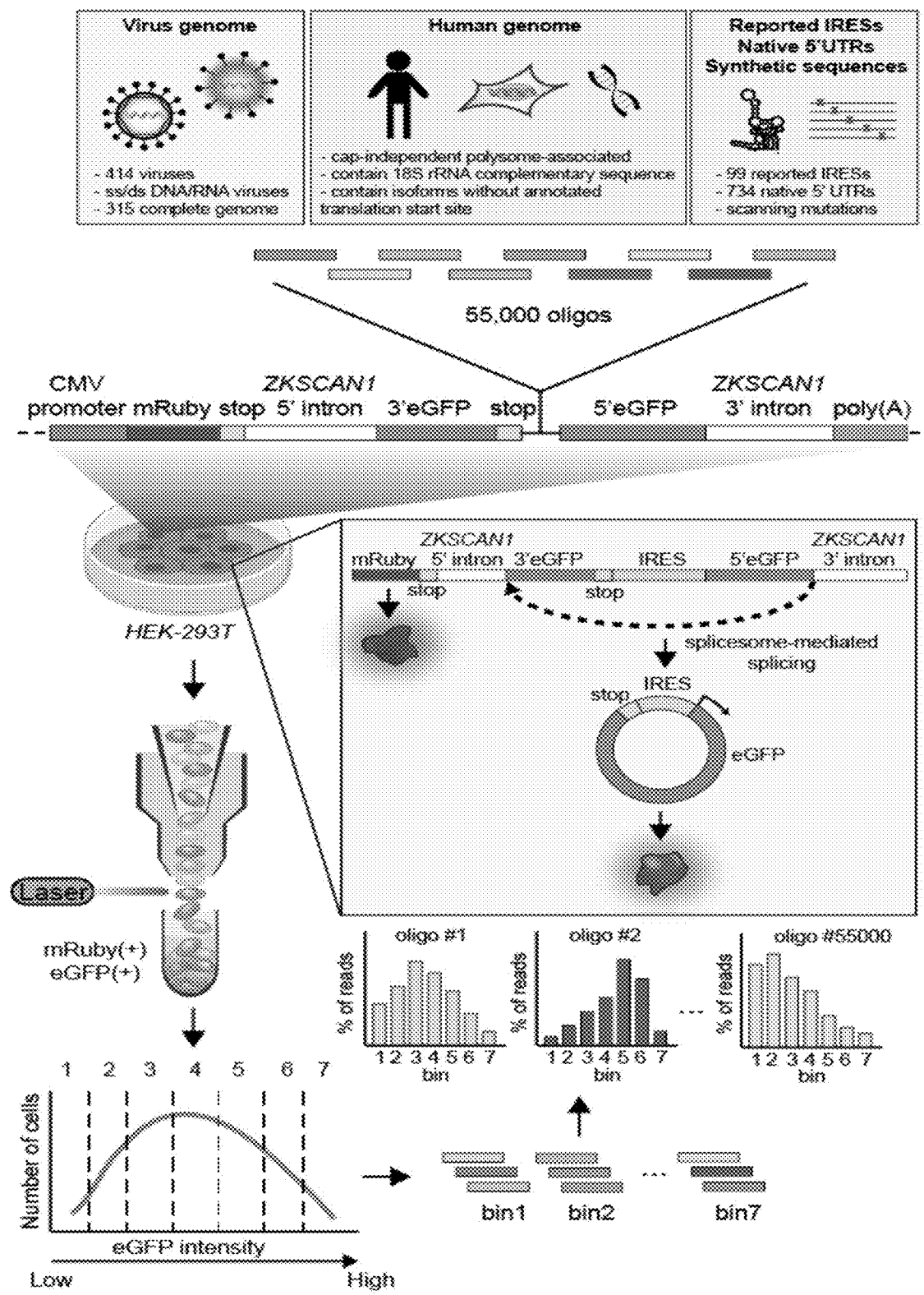
FIG. 1A-1D show high-throughput identification of RNA sequences that can facilitate cap-independent translation activity on circRNA.

The present disclosure is predicated, at least in part, on the development of a high-throughput reporter assay that can systematically screen and quantify the IRES activity of RNA sequences that can facilitate circRNA translation. This assay can identify elements in the primary and secondary structure of a circRNA IRES that are important for facilitating circRNA translation. This assay also enables the identification of potential endogenous protein-coding circRNAs, further expanding the currently-understood proteome. For example, the disclosure demonstrates the identification of a circRNA-encoded protein, circFGFR1p, that functions as a negative regulator of FGFR1 through a dominant negative mechanism to suppress cell growth under stress conditions. The embodiments described herein provide a resource to recognize and manipulate circRNA translation and reveal a new scope of the endogenous circRNA proteome, which provides insights into circRNA-associated diseases and the development of new therapeutic methods targeting circRNA-encoded proteins.

The disclosure is further based on the discovery that circFGFR1p is an endogenous circRNA-encoded protein that is a negative regulator of FGFR1 signaling and suppresses cell growth under stress conditions. While cells decrease global translation under stress conditions, many IRES can drive higher cap-independent translation activity under stress conditions, including the IRES of circZNF-609. Embodiments described herein highlight an important regulatory mechanism for how cells utilize different translation machinery to respond to stress conditions, and illustrate how circRNAs may be used to maintain protein translation under such conditions. While cells predominantly utilize cap-dependent linear mRNA translation to produce proteins, they can shift the RNA source of translation toward circRNA by upregulating the cap-independent translation activity of circRNA IRES under stress conditions. The depletion of circFGFR1 in human cancers may occur to down-regulate circFGFR1p and increase the proliferative signaling through FGF signaling. circRNA-encoded proteins may be useful for expressing individual subunits or "modules" of multi-domain proteins, allowing cells the ability to independently control translation thereof. The disclosure provides a new model of how circRNA translation is regulated by a mechanism which differs from linear mRNA translation and how cells utilize circRNA-encoded proteins to respond to a dynamic environment. The disclosure also provides recombinant circular RNAs comprising a protein-coding nucleic acid sequence and an IRES operably linked to the protein-coding nucleic acid sequence, which can be used to express one or more proteins of interest in a cell.

Definitions

To facilitate an understanding of the present technology, a number of terms and phrases are defined below. Additional definitions are set forth throughout the detailed description.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "nucleic acid sequence," "polynucleotide," and "oligonucleotide" are used interchangeably herein and refer to a polymer or oligomer of pyrimidine and/or purine bases, such as cytosine, thymine, and uracil, and adenine and guanine, respectively (See Albert L. Lehninger, *Principles of Biochemistry*, at 793-800 (Worth Pub. 1982)). The terms encompass any deoxyribonucleotide, ribonucleotide, or peptide nucleic acid component, and any chemical variants thereof, such as methylated, hydroxymethylated, or glycosylated forms of these bases. The polymers or oligomers may be heterogenous or homogenous in composition, may be isolated from naturally occurring sources, or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. A nucleic acid or nucleic acid sequence may comprise other kinds of nucleic acid structures such as, for instance, a DNA/RNA helix, peptide nucleic acid (PNA), morpholino nucleic acid (see, e.g., Braasch and Corey, *Biochemistry*, 41(14): 4503-4510 (2002) and U.S. Pat. No. 5,034,506), locked nucleic acid (LNA; see Wahlestedt et al., *Proc. Natl. Acad. Sci. U.S.A.*, 97: 5633-5638 (2000)), cyclohexenyl nucleic acids (see Wang, *J. Am. Chem. Soc.*, 122: 8595-8602 (2000)), and/or a ribozyme. The terms "nucleic acid" and "nucleic acid sequence" may also encompass a chain comprising non-natural nucleotides, modified nucleotides, and/or non-nucleotide building blocks that can exhibit the same function as natural nucleotides (e.g., "nucleotide analogs"). The term "DNA sequence" is used herein to refer to a nucleic acid comprising a series of DNA bases.

The terms "polypeptide," and "protein" are used interchangeably herein, and refer to a polymeric form of amino acids comprising at least two or more contiguous amino acids chemically or biochemically modified or derivatized amino acids, and polypeptides having modified peptide backbones. The term "peptide" as used herein refers to a class of short polypeptides. The term peptide may refer to a polymer of amino acids (natural or non-naturally occurring) having a length of up to about 100 amino acids. For example, peptides may have a length of about 1 to about 10, about 10 to about 25, about 25 to about 50, about 50 to about 75, about 75 to about 100 amino acids. In some embodiments, the peptides are 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length.

Nomenclature for nucleotides, nucleic acids, nucleosides, and amino acids used herein is consistent with International Union of Pure and Applied Chemistry (IUPAC) standards (see, e.g., bioinformatics.org/sms/iupac.html).

When referring to a nucleic acid sequence or protein sequence, the term "identity" is used to denote similarity between two sequences. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12, 387-395 (1984), or by inspection. Another algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional useful algorithm is gapped BLAST as reported by Altschul et al, (1997) Nucleic Acids Res. 25, 3389-3402. Unless otherwise indicated, percent identity is determined herein using the algorithm available at the internet address: blast.ncbi.nlm.nih-.gov/Blast.cgi.

The terms "internal ribosome entry site," "internal ribosome entry sequence," "IRES" and "IRES sequence region" are used interchangeably herein and refer to cis elements of viral or human cellular RNAs (e.g., messenger RNA (mRNA) and/or circRNAs) that bypass the steps of canonical eukaryotic cap-dependent translation initiation. The canonical cap-dependent mechanism used by the vast majority of eukaryotic mRNAs requires an $m^7G$ cap at the 5' end of the mRNA, initiator Met-tRNAmet, more than a dozen initiation factor proteins, directional scanning, and GTP hydrolysis to place a translationally competent ribosome at the start codon. IRESs typically are comprised of a long and highly structured 5'-UTR which mediates the translation initiation complex binding and catalyzes the formation of a functional ribosome.

The terms "coding sequence," "coding sequence region," "coding region," and "CDS" when referring to nucleic acid sequences may be used interchangeably herein to refer to the portion of a DNA or RNA sequence, for example, that is or may be translated to protein. The terms "reading frame," "open reading frame," and "ORF," may be used interchangeably herein to refer to a nucleotide sequence that begins with an initiation codon (e.g., ATG) and, in some embodiments, ends with a termination codon (e.g., TAA, TAG, or TGA). Open reading frames may contain introns and exons, and as such, all CDSs are ORFs, but not all ORF are CDSs.

The terms "complementary" and "complementarity" refers to the relationship between two nucleic acid sequences or nucleic acid monomers having the capacity to form hydrogen bond(s) with one another by either traditional Watson-Crick base-paring or other non-traditional types of pairing. The degree of complementarity between two nucleic acid sequences can be indicated by the percentage of nucleotides in a nucleic acid sequence which can form hydrogen bonds (e.g., Watson-Crick base pairing) with a second nucleic acid sequence (e.g., about 50%, about 60%, about 70%, about 80%, about 90%, and 100% complementary). Two nucleic acid sequences are "perfectly complementary" if all the contiguous nucleotides of a nucleic acid sequence will hydrogen bond with the same number of contiguous nucleotides in a second nucleic acid sequence. Two nucleic acid sequences are "substantially complementary" if the degree of complementarity between the two nucleic acid sequences is at least 60% (e.g., at least 65%, at least 70%, at least 75%, at least 80%, at least 85%, at least 90%, at least 95%, at least 97%, at least 98%, at least 99%, or 100%) over a region of at least 8 nucleotides (e.g., at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, or more nucleotides), or if the two nucleic acid sequences hybridize under at least moderate, or, in some embodiments high, stringency conditions. Exemplary moderate stringency conditions include overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C., or substantially similar conditions, e.g., the moderately stringent conditions described in Sambrook, J., *Molecular Cloning: A Laboratory Manual*, Cold Spring Harbor Laboratory Press; 4th edition (Jun. 15, 2012). High stringency conditions are conditions that use, for example (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride and 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at (i) 42° C. in 0.2×SSC, (ii) 55° C. in 50% formamide, and (iii) 55° C. in 0.1×SSC (optionally in combination with EDTA). Additional details and an explanation of stringency of hybridization reactions are provided in, e.g., Sambrook, supra; and Ausubel et al., eds., *Short Protocols in Molecular Biology*, 5th ed., John Wiley & Sons, Inc., Hoboken, N.J. (2002). The term "hybridization" or "hybridized" when referring to nucleic acid sequences is the association formed between and/or among sequences having complementarity.

The term "secondary structure," or "secondary structure element" or "secondary structure sequence region" as used herein in reference to nucleic acid sequences (e.g., RNA, DNA, etc), refers to any non-linear conformation of nucleotide or ribonucleotide units. Such non-linear conformations may include base-pairing interactions within a single nucleic acid polymer or between two polymers. Single-stranded RNA typically forms complex and intricate base-pairing interactions due to its increased ability to form hydrogen bonds stemming from the extra hydroxyl group in the ribose sugar. Examples of secondary structures or secondary structure elements include but are not limited to, for example, stem-loops, hairpin structures, bulges, internal loops, multiloops, coils, random coils, helices, partial helices and pseudoknots. In some embodiments, the term "secondary structure" may refer to a SuRE element. The term "SuRE" stands for stem-loop structured RNA element (SuRE).

The term "free energy," as used herein, refers to the energy released by folding an unfolded polynucleotide (e.g., RNA or DNA, etc.) molecule, or, conversely, the amount of energy that must be added in order to unfold a folded polynucleotide (e.g., RNA or DNA, etc.) The "minimum free energy (MFE)" of a polynucleotide (e.g., DNA, RNA, etc.) describes the lowest value of free energy observed for the polynucleotide when assessed for various secondary structures thereof. The MFE of an RNA molecule may be used to predict RNA or DNA secondary structure and is affected by the number, composition, and arrangement of the RNA or RNA nucleotides. The more negative free energy a structure has, the more likely is its formation since more stored energy is released by formation of the structure.

The term "melting temperature (Tm)" refers to the temperature at which about 50% of double-stranded nucleic acid structures (e.g., DNA/DNA, DNA/RNA, or RNA/RNA duplexes) denature and dissociate to single-stranded structures.

The term "recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions and may act to modulate production of a desired product by various mechanisms. Alternatively, DNA sequences encoding RNA that is not translated may also be considered recombinant. Thus, the term "recombinant" nucleic acid also refers to a nucleic acid which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, the artificial combination may be performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may comprise a naturally occurring amino acid sequence.

The terms "operably linked" and "operatively linked," as used herein, refer to an arrangement of elements that are configured so as to perform, function or be structured in such a manner as to be suitable for an intended purpose. For example, a given promoter operably linked to a coding sequence is capable of effecting the expression of the coding sequence when the proper enzymes are present. Expression is meant to include the transcription of any one or more of a recombinant nucleic acid encoding a circular RNA, or mRNA from a DNA or RNA template and can further include translation of a protein from a recombinant circular RNA comprising an IRES sequence (e.g., a non-native IRES). Thus, for example, intervening untranslated yet transcribed sequences can be present between a promoter sequence and a coding sequence and the promoter sequence can still be considered to be "operably linked" to the coding sequence.

As used herein, the term "nonviral-like particle" may refer any protein-based particle that is not a virus or viral-like particle. For example, in some embodiments, a nonviral-like particle is a protein nanogel or protein spheres that allow encapsulation.

As used herein in reference to a lipid nanoparticle, the term "decorated" refers to a lipid nanoparticle that is coupled to one or more targeting agents (e.g., small molecules, peptides, polypeptides, carbohydrates, etc.) The targeting agent binds to one or more peptides, polypeptides, carbohydrates, cells, etc., and allows for targeting of the lipid nanoparticle specifically thereto.

Circular RNAs

Circular RNAs (circRNAs) are single-stranded RNAs that are joined head to tail and were initially discovered in pathogenic genomes such as hepatitis D virus (HDV) and plant viroids (Kos et al., *Nature,* 323: 558-560 (1986); Sanger et al., *PNAS USA,* 73: 3852-3856 (1976)). circRNAs have been recognized as a pervasive class of noncoding RNAs in eukaryotic cells (Salzman et al., *PLoS One,* 7: e30733, (2012); Memczak et al., *Nature,* 495: 333-338 (2013); Hansen et al., *Nature,* 495: 384-388, (2013)). Typically generated through back splicing, circRNAs have been postulated to function in cell-to-cell information transfer or memory due to their extraordinary stability (Jeck, W. R. & Sharpless, N. E., *Nat Biotech,* 32: 453-461, (2014)).

Although the functions of endogenous circRNAs are not known, their large number and the presence of viral circRNA genomes necessitate a system of circRNA immunity, as evidenced by the recent discoveries of human circRNA modulation of viral resistance through regulation of NF90/NF110 and autoimmunity through PKR regulation. Circular RNAs can act as potent adjuvants to induce specific T and B cell responses. In addition, circRNA can induce both innate and adaptive immune responses and have the ability to inhibit the establishment and growth of tumors.

The instant inventors have previously shown that intron identity dictates circRNA immunity. See., e.g., Chen, Y G, et. al, Mol. Cell (2019) 76(1):96-109.e9; Chen, Y G, et. al, Mol. Cell (2017) 67(2):228-238.e5. Because introns are not part of the final circRNA product, it has been hypothesized that introns may direct the deposition of one or more covalent chemical marks onto circRNA. Among the over 100 known RNA chemical modifications, $m^6A$ is the most abundant modification on linear mRNAs and long noncoding RNAs, present on 0.2% to 0.6% of all adenosines in mammalian polyA-tailed transcripts (Roundtree et al., *Cell,* 169: 1187-1200 (2017)). $m^6A$ has recently been detected on mammalian circRNAs (Zhou et al., *Cell Reports,* 20: 2262-2276 (2017)). Human endogenous circRNAs appear to be marked at birth by one or more covalent $m^6A$ modifications, based on the introns that program their back splicing.

The instant disclosure provides a recombinant circular RNA molecule comprising a protein-coding nucleic acid sequence and a non-native an internal ribosome entry site (IRES) operably linked to the protein-coding nucleic acid sequence, and DNA sequences encoding the same. Recombinant circRNA molecules may be generated or engineered according to several methods. For example, recombinant circRNA molecules may be generated by back-splicing of linear RNAs. For example, in some embodiments, a recombinant circular RNA is produced by back-splicing of a downstream 5' splice site (splice donor) to an upstream 3' splice site (splice acceptor). The splice donor and/or splice acceptor may be found, for example, in a human intron or portion thereof that is typically used for circRNA production at endogenous loci as shown in FIG. 1A. In some embodiments, a recombinant circular RNA is produced by contacting a cell with a DNA plasmid, wherein the DNA plasmid encodes a linear RNA, and the linear RNA is back-spliced to produce a recombinant circular RNA. In some embodiments, the DNA plasmid comprises introns from the mammalian ZKSCAN1 gene.

Circular RNAs can be generated by any non-mammalian splicing method. For example, linear RNAs containing various types of introns, including self-splicing group I introns, self-splicing group II introns, spliceosomal introns, and tRNA introns can be circularized. In particular, group I and group II introns have the advantage that they can be readily used for production of circular RNAs in vitro as well as in vivo because of their ability to undergo self-splicing due to their autocatalytic ribozyme activity.

Alternatively, circular RNAs can be produced in vitro from a linear RNA by chemical or enzymatic ligation of the 5' and 3' ends of the RNA. Chemical ligation can be performed, for example, using cyanogen bromide (BrCN) or ethyl-3-(3'-dimethylaminopropyl) carbodiimide (EDC) for activation of a nucleotide phosphomonoester group to allow phosphodiester bond formation (Sokolova, *FEBS Lett,* 232: 153-155 (1988); Dolinnaya et al., *Nucleic Acids Res.,* 19: 3067-3072 (1991); Fedorova, *Nucleosides Nucleotides Nucleic Acids,* 15: 1137-1147 (1996)). Alternatively, enzymatic ligation can be used to circularize RNA. Exemplary ligases that can be used include T4 DNA ligase (T4 Dnl), T4 RNA ligase 1 (T4 Rnl 1), and T4 RNA ligase 2 (T4 Rnl 2).

In other embodiments, splint ligation may be used to generate circular RNA. Splint ligation involves the use of an oligonucleotide splint that hybridizes with the two ends of a linear RNA to bring the ends of the linear RNA together for ligation. Hybridization of the splint, which can be either a deoxyribo-oligonucleotide or a ribooligonucleotide, orients the 5'-phosphate and 3'-OH of the RNA ends for ligation. Subsequent ligation can be performed using either chemical or enzymatic techniques, as described above. Enzymatic ligation can be performed, for example, with T4 DNA ligase (DNA splint required), T4 RNA ligase 1 (RNA splint required) or T4 RNA ligase 2 (DNA or RNA splint). Chemical ligation, such as with BrCN or EDC, is more efficient in some cases than enzymatic ligation if the structure of the hybridized splint-RNA complex interferes with enzymatic activity (see, e.g., Dolinnaya et al. *Nucleic Acids Res,* 21(23): 5403-5407 (1993); Petkovic et al., *Nucleic Acids Res,* 43(4): 2454-2465 (2015)).

While circular RNAs generally are more stable than their linear counterparts, primarily due to the absence of free ends necessary for exonuclease-mediated degradation, additional modifications may be made to the recombinant circRNA described herein to further improve stability. Still other kinds of modifications may improve circularization efficiency, purification of circRNA, and/or protein expression from circRNA. For example, the recombinant circRNA may be engineered to include "homology arms" (i.e., 9-19 nucleotides in length placed at the 5' and 3' ends of a precursor RNA with the aim of bringing the 5' and 3' splice sites into proximity of one another), spacer sequences, and/or a phosphorothioate (PS) cap (Wesselhoeft et al., *Nat. Commun.,* 9: 2629 (2018)). The recombinant circRNA also may be engineered to include 2'-O-methyl-, -fluoro- or —O-methoxyethyl conjugates, phosphorothioate backbones, or 2',4'-cyclic 2'-O-ethyl modifications to increase the stability thereof (Holdt et al., *Front Physiol.*, 9: 1262 (2018); Krutzfeldt et al., *Nature*, 438(7068): 685-9 (2005); and Crooke et al., *CellMetab.*, 27(4): 714-739 (2018)). The recombinant circRNA molecule also may comprise one or more modifications that reduce the innate immunogenicity of the circRNA molecule in a host, such as at least one N6-methyladenosine ($m^6A$).

In some embodiments, the recombinant circular RNA molecule is encoded by a nucleic acid that comprises at least two introns and at least one exon. In some embodiments, a DNA sequence encoding a circular RNA molecule comprises sequences that encode at least two introns and at least one exon. The term "exon," as used herein, refers to a nucleic acid sequence present in a gene which is represented in the mature form of an RNA molecule after excision of introns during transcription. Exons may be translated into protein (e.g., in the case of messenger RNA (mRNA)). The term "intron," as used herein, refers to a nucleic acid sequence present in a given gene which is removed by RNA splicing during maturation of the final RNA product. Introns are generally found between exons. During transcription, introns are removed from precursor messenger RNA (premRNA), and exons are joined via RNA splicing. In some embodiments, the recombinant circular RNA molecule comprises a nucleic acid sequence which includes one or more exons and one or more introns.

Accordingly, circular RNAs can be generated by splicing of either an endogenous or exogenous intron, as described in WO 2017/222911. As used herein, the term "endogenous intron" means an intron sequence that is native to the host cell in which the circRNA is produced. For example, a human intron is an endogenous intron when the circRNA is expressed in a human cell. An "exogenous intron" means an intron that is heterologous to the host cell in which the circRNA is generated. For example, a bacterial intron would be an exogenous intron when the circRNA is expressed in a human cell. Numerous intron sequences from a wide variety of organisms and viruses are known and include sequences derived from genes encoding proteins, ribosomal RNA (rRNA), or transfer RNA (tRNA). Representative intron sequences are available in various databases, including the Group I Intron Sequence and Structure Database (rna.whu.edu.cn/gissd/), the Database for Bacterial Group II Introns (webapps2.ucalgary.ca/~groupii/index.html), the Database for Mobile Group II Introns (fp.ucalgary.ca/group2introns), the Yeast Intron DataBase (emblS16 heidelberg.de/ExternalInfo/seraphin/yidb.html), the Ares Lab Yeast Intron Database (compbio.soe.ucsc.edu/yeast_introns.html), the U12 Intron Database (genome.crg.es/cgibin/u12db/u12db.cgi), and the Exon-Intron Database (bpg.utoledo.edu/~afedorov/lab/eid.html).

In some embodiments, a DNA molecule encoding a recombinant circular RNA molecule comprises a self-splicing group I intron. Group I introns are a distinct class of RNA self-splicing introns which catalyze their own excision from mRNA, tRNA, and rRNA precursors in a wide range of organisms. All known group I introns present in eukaryote nuclei interrupt functional ribosomal RNA genes located in ribosomal DNA loci. Nuclear group I introns appear widespread among eukaryotic microorganisms, and the plasmodial slime molds (myxomycetes) contain an abundance of self-splicing introns. The self-splicing group I intron included in the circular RNA molecule may be obtained or derived from any organism, such as, for example, bacteria, bacteriophages, and eukaryotic viruses. Self-splicing group I introns also may be found in certain cellular organelles, such as mitochondria and chloroplasts, and such self-splicing introns may be incorporated into the circular RNA molecule.

In some embodiments, the recombinant circular RNA molecule is generated from a DNA molecule that comprises a self-splicing group I intron of the phage T4 thymidylate synthase (td) gene. The group I intron of phage T4 thymidylate synthase (td) gene is well characterized to circularize while the exons linearly splice together (Chandry and Belfort, *Genes Dev.*, 1: 1028-1037 (1987); Ford and Ares, *Proc. Natl. Acad. Sci. USA,* 91: 3117-3121 (1994); and Perriman and Ares, *RNA,* 4: 1047-1054 (1998)). When the td intron order is permuted (i.e., 5' half placed at the 3' position and vice versa) flanking any exon sequence, the exon is circularized via two autocatalytic transesterification reactions (Ford and Ares, supra; Puttaraju and Been, *Nucleic Acids Symp. Ser.*, 33: 49-51 (1995)).

In some embodiments, the recombinant circular RNA molecule is encoded by a DNA molecule that comprises a ZKSCAN1 intron. The ZKSCAN1 intron is described in, for example, Yao, Z., et al., Mol. Oncol. (2017) 11(4):422-437. In some embodiments, the recombinant circular RNA molecule is encoded by a DNA molecule that comprises a miniZKSCAN1 intron.

The recombinant circular RNA molecule may be of any length or size. For example, the recombinant circular RNA molecule may comprise between about 200 nucleotides and about 10,000 nucleotides (e.g., about 300, about 400, about 500, about 600, about 700, about 800, about 900, about 1,000, about 2,000, about 3,000, about 4,000, about 5,000, about 6,000, about 7,000, about 8,000, or about 9,000 nucleotides, or a range defined by any two of the foregoing values). In some embodiments, the recombinant circular RNA molecule comprises between about 500 and about 6,000 nucleotides (about 550, about 650, about 750, about 850, about 950, about 1,100, about 1,200, about 1,300, about 1,400, about 1,500, about 1,600, about 1,700, about 1,800, about 1,900, about 2,100, about 2,200, about 2,300, about 2,400, about 2,500, about 2,600, about 2,700, about 2,800, about 2,900, about 3,100, about 3,300, about 3,500, about 3,700, about 3,800, about 3,900, about 4,100, about 4,300, about 4,500, about 4,700, about 4,900, about 5,100, about 5,300, about 5,500, about 5,700, or about 5,900 nucleotides, or a range defined by any two of the foregoing values). In one embodiment, the recombinant circular RNA molecule comprises about 1,500 nucleotides.

In some embodiments, a recombinant circular RNA molecule comprises a protein-coding nucleic acid sequence region and an internal ribosome entry site (IRES) sequence region operably linked to the protein-coding nucleic acid sequence region, wherein the IRES comprises: at least one sequence region having secondary structure element; and a sequence region that is complementary to an 18S ribosomal RNA (rRNA); wherein the IRES has a minimum free energy (MFEL) of less than −18.9 kJ/mol and a melting temperature of at least 35.0° C. In some embodiments, the IRES sequence is linked to the protein-coding nucleic acid sequence region in a non-native configuration.

The disclosure also provides a recombinant circular RNA molecule comprising a protein-coding nucleic acid sequence region and an internal ribosome entry site (IRES) sequence region operably linked to the protein-coding nucleic acid sequence; wherein the IRES is encoded by any one of the nucleic acid sequences listed in of SEQ ID NO: 1-228 or SEQ ID NO: 229-17201, or a nucleic acid sequence that has at least 90% or at least 95% identity or homology thereto. In some embodiments, the IRES sequence is linked to the protein-coding nucleic acid sequence region in a non-native configuration.

circRNA Internal Ribosome Entry Sites

The recombinant circular RNAs described herein comprise an internal ribosome entry site (IRES) operably linked to a protein-coding sequence of the circRNA in a non-native configuration. Inclusion of an IRES permits the translation of one or more open reading frames from a circular RNA. The IRES element attracts a eukaryotic ribosomal translation initiation complex and promotes translation initiation. It will be appreciated that there are two known mechanisms by which translation is initiated in eukaryotes. The first is the canonical cap-dependent mechanism that is used by the vast majority of eukaryotic mRNAs, which requires an $m^7G$ cap at the 5'end of the mRNA, initiator Met-tRNAmet, more than a dozen initiation factor proteins, directional scanning, and GTP hydrolysis to place a translationally competent ribosome at the start codon. The second mechanism is cap-independent initiation that is used by some mRNAs as well as many eukaryote-infecting viruses. This mechanism bypasses the need for the cap and often many of the protein factors, using cis-acting IRES RNA elements to recruit the ribosome and initiate protein synthesis. There is great diversity among viral IRES RNAs in terms of their sequences, proposed secondary structures, and functional requirements for protein factors, but all drive a mode of translation initiation that depends on specific RNA sequences and likely specific RNA structures in the IRES.

Accordingly, provided herein are various IRES sequences which, when present in a circRNA, may drive translation of a protein. In some embodiments, the IRES of a circRNA may be operably linked to a protein-coding nucleic acid sequence. In some embodiments, the IRES of a circRNA is operably linked to a protein-coding nucleic acid sequence in a non-native configuration. In some embodiments, the IRES is a human IRES. In some embodiments, the IRES is a viral IRES.

As used herein, the term "non-native configuration" refers to a linkage between an IRES and a protein-coding nucleic acid that does not occur in a naturally occurring circRNA molecule. For example, a viral IRES may be operably linked to a protein-coding nucleic acid sequence in a circular RNA, or an IRES that is not found in naturally occurring circRNA molecules may be operably linked to a protein-coding nucleic acid sequence in a circRNA. In some embodiments, an IRES that is found in naturally occurring circRNA molecules operably linked to a certain protein-coding nucleic acid is operably linked to a different protein-coding nucleic acid (i.e., a nucleic acid to which the IRES is not operably linked in any naturally-occurring circRNA). In some embodiments, an IRES that is found in naturally occurring linear mRNAs is operably linked to a protein coding sequence in a circular RNA.

A number of linear IRES sequences are known and may be included in a recombinant circular RNA molecule as described herein. For example, linear IRES sequences may be derived from a wide variety of viruses, such as from leader sequences of picornaviruses (e.g., encephalomyocarditis virus (EMCV) UTR) (Jang et al., *J. Virol.*, 63: 1651-1660 (1989)), the polio leader sequence, the hepatitis A virus leader, the hepatitis C virus IRES, human rhinovirus type 2 IRES (Dobrikova et al., *Proc. Natl. Acad. Sci.*, 100(25): 15125-15130 (2003)), an IRES element from the foot and mouth disease virus (Ramesh et al., *Nucl. Acid Res.*, 24: 2697-2700 (1996)), and a giardiavirus IRES (Garlapati et al., *J. Biol. Chem.*, 279(5): 3389-3397 (2004)). A variety of nonviral IRES sequences also can be included in a circular RNA molecule, including but not limited to, IRES sequences from yeast, the human angiotensin II type 1 receptor IRES (Martin et al., *Mol. Cell Endocrinol.*, 212: 51-61 (2003)), fibroblast growth factor IRESs (e.g., FGF-1 IRES and FGF-2 IRES, Martineau et al., *Mol. Cell. Biol.*, 24(17): 7622-7635 (2004)), vascular endothelial growth factor IRES (Baranick et al., *Proc. Natl. Acad. Sci. U.S.A.*, 105(12): 4733-4738 (2008); Stein et al., *Mol. Cell. Biol.*, 18(6): 3112-3119 (1998); Bert et al., *RNA*, 12(6): 1074-1083 (2006)), and insulin-like growth factor 2 IRES (Pedersen et al., *Biochem. J.*, 363(Pt 1): 37-44 (2002)).

IRES sequences and vectors encoding IRES elements are commercially available from a variety of sources, such as, for example, Clontech (Mountain View, Calif.), Invivogen (San Diego, Calif.), Addgene (Cambridge, Mass.) and GeneCopoeia (Rockville, Md.), and IRESite: The database of experimentally verified IRES structures (iresite.org). Notably, these databases focus on activity of IRES sequences in mRNA (i.e., linear RNAs), and do not focus on circRNA IRES activity profiles.

Figure 19A:
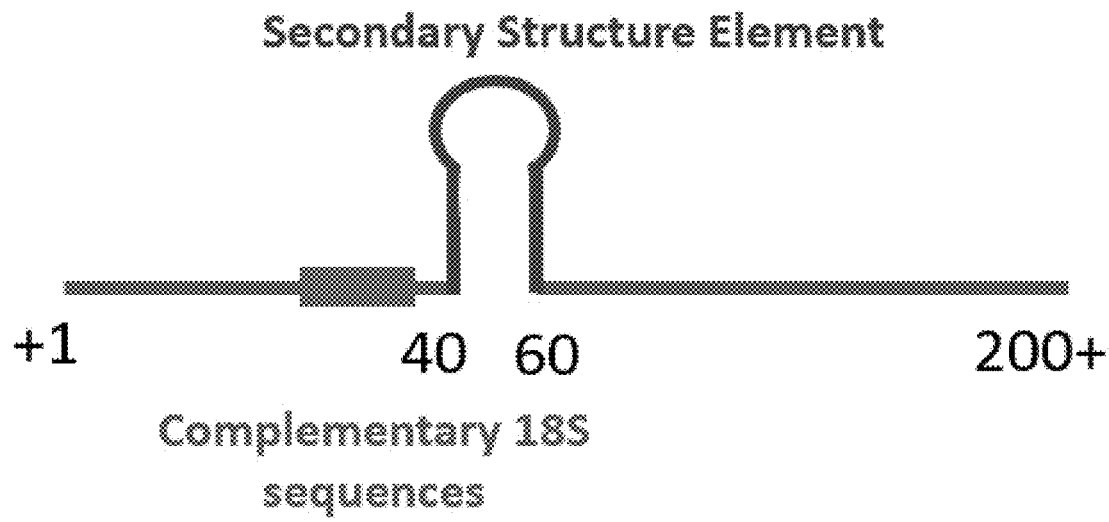
FIGS. 19A and 19B provide schematics of fixed positions of secondary structure elements as part of an IRES, wherein the secondary structure element spans from approximately nucleotide positions 40-60 bp from +1 start site of IRES sequence. The 18S complementary sequences may be positioned either 5' (FIG. 19A) or 3' (FIG. 19B) to the secondary structure element. In these figures, the secondary structure element is a hairpin; however the secondary structure element may have one or more alternative structures as described herein.
Figure 19B:
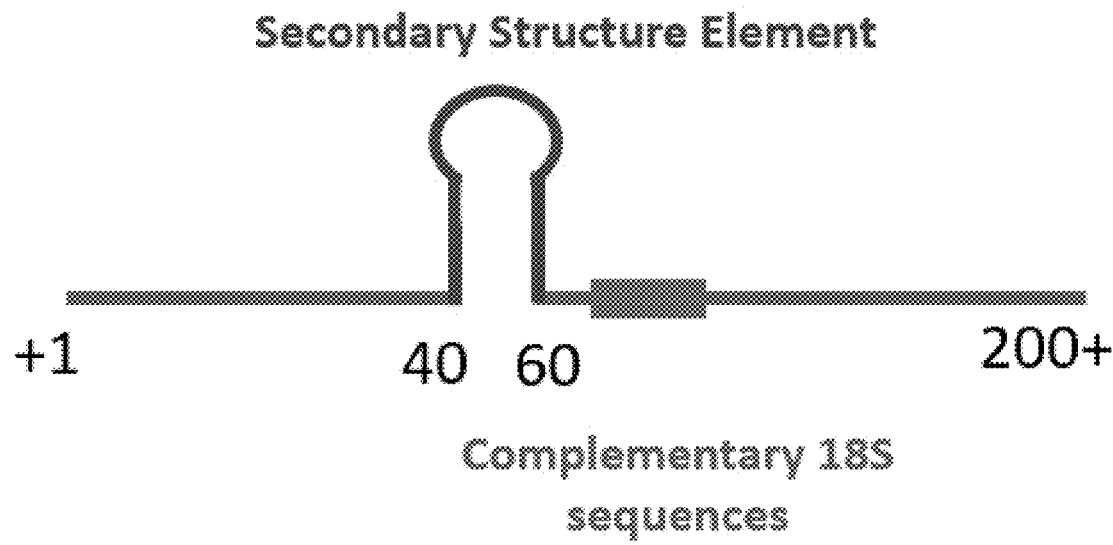

In some embodiments, the IRES comprises at least one RNA secondary structure element. Intramolecular RNA base pairing is often the basis of RNA secondary structure and in some circumstances be a critical determinant of overall macromolecular folding. In conjunction with cofactors and RNA binding proteins (RBPs), secondary structure elements can form higher order tertiary structures and thereby confer catalytic, regulatory, and scaffolding functions to RNA. Thus, the IRES may comprise any RNA secondary structure element that imparts such structural or functional determinants. In some embodiments, the RNA secondary structure may be formed from the nucleotides at about position 40 to about position 60 of the IRES, relative to the 5' end thereof. The most common RNA secondary structures are helices, loops, bulges, and junctions, with stem-loops or hairpin loops being the most common element of RNA secondary structure. A stem-loop is formed when the RNA chains fold back on themselves to form a double helical tract called the stem, with the unpaired nucleotides forming a single-stranded region called the loop. Bulges and internal loops are formed by separation of the double helical tract on either one strand (bulge) or on both strands (internal loops) by unpaired nucleotides. A tetraloop is a four-base pairs hairpin RNA structure. There are three common families of tetraloop in ribosomal RNA: UNCG, GNRA, and CUUG (N is one of the four nucleotides and R is a purine). Pseudoknots are formed when nucleotides from the hairpin loop pair with a single stranded region outside of the hairpin to form a helical segment. RNA secondary structure is further described in, e.g., Vandivier et al., Annu Rev Plant Biol., 67: 463-488 (2016); and Tinoco and Bustamante, supra). In some embodiments, the IRES of the recombinant circRNA molecule comprises at least one stem-loop structure. The at least one RNA secondary structure element may be located at any position of the IRES, so long as translation is efficiently initiated from the IRES. In some embodiments, the stem portion of the stem-loop may comprise from 3-7 base pairs, 4, 5, 6, 7, 8, 9, 10, 11 or 12 base pairs or more. The loop portion of the stem-loop may comprise from 3-12 nucleotides, including 4, 5, 6, 7, 8, 9, 10, 11, 12 or more nucleotides. The stem-loop structure may also have on either side of the stem one or more bulges (mismatches). In some embodiments, the RNA secondary structure element is formed from the nucleotides at about position 40 to about position 60 of the IRES, wherein the first nucleic acid at the 5' end of the IRES is considered to be position 1. In some embodiments, the sequence that is complementary to an 18S rRNA is located 5' to the at least one RNA secondary structure element (i.e., in the range of about position 1 to about position 40 of the IRES, See FIG. 19A). In some embodiments, the sequence that is complementary to an 18S rRNA is located 3' to the a least one RNA secondary structure element (i.e., in the range of about position 61 to the end of the IRES, See FIG. 19B). Sequences encoding exemplary secondary structure-forming RNA sequences that may be included in the IRES described herein are provided in SEQ ID NO: 17202-28976.

In some embodiments, the at least one RNA secondary structure element of the IRES is a stem-loop. In some embodiments, the at least one RNA secondary structure element is encoded by any one of the nucleic acid sequences of SEQ ID NO: 17202-28976. In some embodiments, the at least one RNA secondary structure element is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity relative to any one of SEQ ID NO: 17202-28976. In some embodiments, the at least one RNA secondary structure element is encoded by a nucleic acid sequence having at least 1, at least 2, at least 3, at least 4, at least 5, at least 6, at least 7, at least 8, at least 9 at least 10, or more nucleotide substitutions relative to any one of SEQ ID NO: 17202-28976.

RNA secondary structure typically can be predicted from experimental thermodynamic data coupled with chemical mapping, nuclear magnetic resonance (NMR) spectroscopy, and/or sequence comparison. In some embodiments, the RNA secondary structure is predicted by a machine-learning/deep-learning algorithm (e.g., CNN) (See, Zhao, Q., et al., "Review of Machine-Learning Methods for RNA Secondary Structure Prediction," Sep. 1, 2020 (available on the world wide web at: arxiv.org/abs/2009.08868). A variety of algorithms and software packages for RNA secondary structure prediction and analysis are known in the art and can be used in the context of the present disclosure (see, e.g., Hofacker I. L. (2014) Energy-Directed RNA Structure Prediction. In: Gorodkin J., Ruzzo W. (eds) RNA Sequence, Structure, and Function: Computational and Bioinformatic Methods. Methods in Molecular Biology (Methods and Protocols), vol 1097. Humana Press, Totowa, N.J.; Mathews et al., supra; Mathews, et al. "RNA secondary structure prediction," Current Protocols in Nucleic Acid Chemistry, Chapter 11 (2007): Unit 11.2. doi:10.1002/0471142700.nc1102s28; Lorenz et al., Methods, 103: 86-98 (2016); Mathews et al., Cold Spring Harb Perspect Biol., 2(12): a003665 (2010)).

In some embodiments, the IRES of the recombinant circRNA may comprise a nucleic acid sequence that is complementary to 18S ribosomal RNA (rRNA). Eukaryotic ribosomes, also known as "80S" ribosomes, have two unequal subunits, designated small subunit (40S) (also referred to as "SSU") and large subunit (60S) (also referred to as "LSU") according to their sedimentation coefficients. Both subunits contain dozens of ribosomal proteins arranged on a scaffold composed of ribosomal RNA (rRNA). In eukaryotes, eukaryotic 80S ribosomes contain greater than 5500 nucleotides of rRNA: 18S rRNA in the small subunit, and 5S, 5.8S, and 25S rRNA in the large subunit. The small subunit monitors the complementarity between tRNA anticodon and mRNA, while the large subunit catalyzes peptide bond formation. Ribosomes typically contain about 60% rRNA and about 40% protein. Although the primary structure of rRNA sequences can vary across organisms, base-pairing within these sequences commonly forms stem-loop configurations.

In some embodiments, the IRES of the recombinant circRNA may comprise any nucleic acid sequence that is complementary to any eukaryotic 18S rRNA sequence. In some embodiments, the nucleic acid sequence that is complementary to 18S rRNA is encoded by any one of the nucleic acid sequences set forth in Table 1. In some embodiments, the nucleic acid sequence that is complementary to 18S rRNA is encoded by a nucleic acid sequence that has at least 80%, at least 85%, at least 90%, at least 91%, at least 92%, at least 93%, at least 94%, at least 95%, at least 96%, at least 97%, at least 98%, or at least 99% identity or homology to a sequence set forth in Table 1. In some embodiments, the nucleic acid sequence that is complementary to 18S rRNA is encoded by a nucleic acid sequence that has at least 1, at least 2, at least 3, at least 4, at least 5, at least 6, at least 7, at least 8, at least 9, at least 10, or more nucleotide substitutions relative to a nucleic acid sequence set forth in Table 1.

TABLE 1

Illustrative DNA sequences that encode RNA sequences that are complementary to 18S RNA

| SEQ ID NO: | Nucleic Acid Sequence |
|---|---|
| 28977 | CACCTACGGAAACCTTGTTACGACTTTTACTTCCTCTAGATAGTCAAGTTCGACCGTCTTCT CAGCGCTCCGCCAGGGCCGTGGGCCGACCCCGGCGGGGCCGATCCGAGGGCCTCACTAAA CCATCCAATCGGTAGTAGCGACGGGCGGTGTGTACAAAGGGCAGGGACTTAATCAACGCA AGCTTATGACCCGCACTTACTGGGAATTCCTCGTTCATGGGGAATAATTGCAATCCCC |
| 28978 | GGGACGCCGACCGCTCGGGGGTCGCGTAACTAGTTAGCATGCCAGAGTCTCGTTCGTTATC GGAATTAACCAGACAAATCGCTCCACCAACTAAGAACGGCCATGCACCACCACCC |
| 28979 | GTTTATGGTCGGAACTACGACGGTATCTGATCGTCTTCGAACCTCCGACTTTCGTTCTTGAT TAATGAAAACATTCTTGGCAAATGCTTTCGCTCTGGTCCGTCTTGCGCCGGTCCAAGAATT TCACCTCTAGCGGCGCAATACGAATGCCCCCGGCCGTCCCTCTTAATCATGGCCTCAGTTC CGAAAACCAACAAAATAGAACCGCGGTCCTATTCCATTATTCCTAGCTGCGGTATCCAGGC GGCTCGGGCCTGCTTTGAACACTCTAATTTTTTCAAAGTAAACGCTTCGGG |
| 28980 | AGAGCATCGAGGGGGCGCCGAGAGGCAAGGGGCGGGGACGGGCGGTGGCTCGCCTCGCG GCGGACCGCCCGCCCGCTCCC |

TABLE 1-continued

Illustrative DNA sequences that encode RNA sequences that are complementary to 18S RNA

| SEQ ID NO: | Nucleic Acid Sequence |
|---|---|
| 28981 | TACGAGCTTT |
| 28982 | ATACGCTATTGGAGCTGGAATTACCGCGGCTGCTGGCACCAGACTTGCCCTCCAATGGATC CTCGTTAAAGGATTTAAAGTGGACTCATTCCAATTACAGGGCCTCGAAAGAGTCCTGTA |
| 28983 | GGGGGCGTGCGATCGGCCCGAGGTTATCTAGAGTCACCAAAGCCGCCGGCGCCCGCCCCC CGGCCGGGGCCGGAGAGGGG |

The most commonly used criterion for RNA secondary structure prediction is the minimum free energy (MFE), since, according to thermodynamics, the MFE structure is not only the most stable, but also the most probable one in thermodynamic equilibrium. The MFE of an RNA or DNA molecule is affected by three properties of nucleotides in the RNA/DNA sequence: number, composition, and arrangement. For example, longer sequences are on average more stable because they can form more stacking and hydrogen bond interactions, guanine-cytosine (GC)-rich RNAs are typically more stable than adenine-uracil (AU)-rich sequences, and nucleotide order influences the folding structure stability because it determines the number and the extension of loops and double-helix conformations. It has been found that mRNAs and microRNA precursors, unlike other non-coding RNAs, have greater negative MFE than expected given their nucleotide numbers and compositions. Thus, free energy also can be employed as a criterion for the identification of functional RNAs.

The IRES of the recombinant circRNA molecule may comprise a minimum free energy (MFE) of less than about −15 kJ/mol (e.g., less than about −16 kJ/mol, less than about −17 kJ/mol, less than about −18.5 kJ/mol, less than about −19 kJ/mol, less than about −18.9 kJ/mol, less than about −20 kJ/mol, less than about −30 kJ/mol). In some embodiments, the MFE is greater than about −90 kJ/mol (e.g., greater than about −85 kJ/mol, greater than about −80 kJ/mol, greater than about −70 kJ/mol, greater than about −60 kJ/mol, greater than about −50 kJ/mol, greater than about −40 kJ/mol). In some embodiments, the IRES has a has a minimum free energy (MFE) of about −18.9 kJ/mol or less. In some embodiments, the IRES has a MFE in the range of about −15.9 kJ/mol to about −79.9 kJ/mol. In some embodiments, the IRES may comprise a MFE in the range of about −12.55 kJ/mol to about −100.15 kJ/mol. In some embodiments, the IRES is a viral IRES and has a MFE in the range of about −15.9 kJ/mol to about −79.9 kJ/mol. In some embodiments, the IRES is a human IRES and has a MFE in the range of about −12.55 kJ/mol to about −100.15 kJ/mol.

In some embodiments, the at least one secondary structure element of an IRES of may comprise a minimum free energy (MFE) of less than about −0.4 kJ/mol, less than about −0.5 kJ/mol, less than about −0.6 kJ/mol, less than about −0.7 kJ/mol, less than about −0.8 kJ/mol, less than about −0.9 kJ/mol, or less than about −1.0 kJ/mol. In some embodiments, the at least one secondary structure element of the IRES may comprise a MFE of less than about −0.7 kJ/mol.

In some embodiments, the RNA sequence comprising the nucleotides at about position 40 to about position 60 of an IRES of a circRNA described herein may comprise a minimum free energy (MFE) of less than about −0.4 kJ/mol, less than about −0.5 kJ/mol, less than about −0.6 kJ/mol, less than about −0.7 kJ/mol, less than about −0.8 kJ/mol, less than about −0.9 kJ/mol, or less than about −1.0 kJ/mol. In some embodiments, the RNA sequence comprising the nucleotides at about position 40 to about position 60 of the IRES may comprise a MFE of less than about −0.7 kJ/mol.

As discussed, above, the minimum free energy of a particular RNA (e.g., an RNA produced from a DNA sequence) may be determined using a variety of computational methods and algorithms. The most commonly used software programs, employed to predict the secondary RNA or DNA structures by MFE algorithms, make use of the so-called nearest-neighbor energy model. This model uses free energy rules based on empirical thermodynamic parameters (Mathews et al., *JMol Biol*, 288: 911-940 (1999); and Mathews et al., *Proc NatlAcad Sci USA*, 101: 7287-7292 (2004)) and computes the overall stability of an RNA or DNA structure by adding independent contributions of local free energy interactions due to adjacent base pairs and loop regions. In sequences with homogeneous nucleotide arrangements and compositions, the additive and independent nature of the local free energy contributions suggests a linear relationship between computed MFE and sequence length (Trotta, E., *PLoS One*, 9(11): e1 13380 (2014)). Algorithms for determining MFE are further described in, e.g., Hajiaghayi et al., *BMC Bioinformatics*, 13: 22 (2012); Mathews, D. H., *Bioinformatics*, Volume 21, Issue 10: 2246-2253 (2005); and Doshi et al., *BMC Bioinformatics*, 5: 105 (2004) doi 10.1186/1471-2105-5-105).

One of ordinary skill in the art will appreciate that the melting temperature ($T_m$) of a particular circRNA molecule may also be indicative of stability. Indeed, RNA sequences with high $T_m$ generally contain thermo-stable functionally important RNA structures (see, e.g., *Nucleic Acids Res.*, 45(10): 6109-6118 (2017)). Thus, in some embodiments, the IRES of the recombinant circRNA molecule has a melting temperature of at least 35.0° C. In some embodiments, the IRES of the recombinant circRNA molecule has a melting temperature of at least 35.0° C., but not more than about 85° C. In some embodiments, in some embodiments, the RNA secondary structure has a melting temperature of at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C. or greater. In some embodiments, the melting temperature is not more than about 85° C., not more than about 75° C., not more than about 70° C., not more than about 65° C., not more than about 60° C., not more than about 55° C., not more than about 50° C. or less.

The melting temperature of a particular nucleic acid molecule can be determined using thermodynamic analyses and algorithms described herein and known in the art (see, e.g., Kibbe W. A., *Nucleic Acids Res.,* 35(Web Server issue): W43-W46 (2007). doi:10.1093/nar/gkm234; and Dumousseau et al., *BMC Bioinformatics,* 13: 101 (2012). doi.org/10.1186/1471-2105-13-101).

In some embodiments, the IRES comprises at least one RNA secondary structure element; and a nucleic acid sequence that is complementary to an 18S ribosomal RNA (rRNA); wherein the IRES has a minimum free energy (MFE) of −18.9 kJ/mol or less and a melting temperature of at least 35.0° C. In some embodiments, the RNA secondary structure element of the IRES has a has a minimum free energy (MFE) of less than −18.9 kJ/mol, and is formed from the nucleotides at about position 40 to about position 60 of the IRES, wherein the first nucleic acid at the 5' end of the IRES is considered to be position 1. In some embodiments, the RNA secondary structure element has a melting temperature of at least 35.0° C., and is formed from the nucleotides at about position 40 to about position 60 of the IRES, wherein the first nucleic acid at the 5' end of the IRES is considered to be position 1.

Because circRNA molecules are often generated from linear RNAs by back-splicing of a downstream 5' splice site (splice donor) to an upstream 3' splice site (splice acceptor), the recombinant circular RNA molecule may further comprise a back-splice junction. In some embodiments, the IRES may be located within about 100 to about 200 nucleotides of the back-splice junction. In addition, it has been observed that regions of RNA with higher G-C content have more stable secondary structures than RNA strands with lower G-C content. Thus, in some embodiments, the IRES of the recombinant circRNA molecule may further comprise a minimum level of G-C base pairs. For example, the non-native IRES of the recombinant circRNA molecule may comprise a G-C content of at least 25% (e.g., at least 30%, at least 35%, at least 40%, at least 45% or more), but not more than about 75% (e.g., about 70%, about 65%, about 60%, about 55%, about 50% or less). In some embodiments, the IRES has a G-C content of at least 25%.

G-C content of a given nucleic acid sequence may be measured using any method known in the art, such as, for example chemical mapping methods (see, e.g., Cheng et al., *PNAS,* 114 (37): 9876-9881 (2017); and Tian, S. and Das, R., *Quarterly Reviews of Biophysics,* 49: e7 doi:10.1017/S0033583516000020 (2016)).

Exemplary sequences encoding IRESs for use in the circRNA molecules of the present disclosure are set forth in of SEQ ID NO: 1-228 or SEQ ID NO: 229-17201. Thus, the disclosure further provides a recombinant circular RNA molecule comprising a protein-coding nucleic acid sequence and an IRES operably linked to the protein-coding nucleic acid sequence in a non-native configuration; wherein the IRES is encoded by any one of the nucleic acid sequences listed in of SEQ ID NO: 1-228 or SEQ ID NO: 229-17201.

In some embodiments, the IRES is encoded by any one of the nucleic acid sequences set forth in any one of SEQ ID NO: 1-228. In some embodiments, the IRES is encoded by a nucleic acid sequence that has at least 80%, at least 85%, at least 90%, at least 91%, at least 92%, at least 93%, at least 94%, at least 95%, at least 96%, at least 97%, at least 98, or at least 99% identity to any one of the nucleic acid sequences of SEQ ID NO: 1-228. In some embodiments, the IRES is encoded by a nucleic acid sequence that has at least 1, at least 2, at least 3, at least 4, at least 5, at least 6, at least 7, at least 8, at least 9, at least 10 or more nucleotide substitutions relative to any one of the sequences of SEQ ID NO: 1-228.

In some embodiments, the IRES is encoded by any one of the nucleic acid sequences set forth in any one of SEQ ID NO: 229-17201. In some embodiments, the IRES is encoded by a nucleic acid sequence that has at least 80%, at least 85%, at least 90%, at least 91%, at least 92%, at least 93%, at least 94%, at least 95%, at least 96%, at least 97%, at least 98, or at least 99% identity or homology to any one of the nucleic acid sequences of SEQ ID NO: 229-17201. In some embodiments, the IRES is encoded by a nucleic acid sequence that has at least 1, at least 2, at least 3, at least 4, at least 5, at least 6, at least 7, at least 8, at least 9, at least 10 or more nucleotide substitutions relative to any one of the sequences in any one of SEQ ID NO: 229-17201.

In some embodiments, the IRES is encoded by the nucleic acid sequences denoted Index 876 (SEQ ID NO: 531), 6063 (SEQ ID NO: 2270), 7005 (SEQ ID NO: 2602), 8228 (SEQ ID NO: 3042), or 8778 (SEQ ID NO: 3244). In some embodiments, the IRES is encoded by the nucleic acid sequence of SEQ ID NO: 33948.

In some embodiments, the IRES is encoded by any one of the nucleic acid sequences set forth in Table 2. In some embodiments, the IRES is encoded by a nucleic acid sequence that has at least 80%, at least 85%, at least 90%, at least 91%, at least 92%, at least 93%, at least 94%, at least 95%, at least 96%, at least 97%, at least 98, or at least 99% identity or homology to one or the nucleic acid sequences of Table 2. In some embodiments, the IRES is encoded by a nucleic acid sequence that has at least 1, at least 2, at least 3, at least 4, at least 5, at least 6, at least 7, at least 8, at least 9, at least 10 or more nucleotide substitutions relative to any one of the sequences in Table 2.

TABLE 2

Illustrative Sequences Encoding IRES sequences

| Oligo-nucleotide Identifier | Sequence | SEQ ID NO: |
|---|---|---|
| 4173 | CATCCTCCTGCTGAAGTGACAAGCCACGCTGCTTCTGGAGCCAAAGCTGACCAAGAAGAACAAATCCACCCCAGATCTAGACTCAGGTCACCTCCTGAAGCCCTCGTTCAGGGTCGATATCCCCACATCAAGGACGGTGAGGATCTTAAAGACCACTCAACAGAAAGTAAAAAA | 33946 |
| 2125 | GCAGAAGGGAAACGTGAAGAAGGTGAAGATGGCGGTGGCCAGGGCCGGGGTCTTGGGAGTCCAGTGGCTGCAAAGGGCATCCCGGAACGTGATGCCGCTGGGCGCACGGACAGCCTCCCACATGACCAAGGACATGTTCCCGGGGCCCTATCCTAGGACCCCAGAAGAACGGGC | 33947 |

TABLE 2-continued

Illustrative Sequences Encoding IRES sequences

| Oligo-nucleotide Identifier | Sequence | SEQ ID NO: |
|---|---|---|
| 6742 | AGACTCGGGAACTGCCTGAATGTGGTTTGGGACACGAGACCTCATC ATATTGATGAGCGAACAAACAAGAACATTTCCTCCCTCCCCTCCTTT GAATTGAAATGGCACATTAAGACTTGTCACGGCTTCTCACTGGGACT GGAGACCTCGTTCCTTCACCCCGCGTGTCGCCAG | 33948 |
| 8839 | AGGTGGGCGGTGGCGGTAGGTGGGTGGCCAGCGACTGGCAACGCGG TGGCTTAGACGCGCGAGATCCGGCCAGGGTCAGAGTACTGTAAGAT TGATGTTAAAGGCATGGTGTTCACCCCACTTCATCAGCGTACATAAG TTATCTCTTCTTTTGGACCCTTATTTTATGCCATA | 33949 |
| 8279 | GGAGGCAGGTTGATGTGTTTGTGCTTCCTTCTACAGCCAATATGAAA AGGCCTAGTAAGTGGGGTCGGGAGGCGGGCGTGGAGGGACCCACGT CTGGAAGTTGCTGCAGCCACCACGACGCTCTTCTACGGCTACGGCTT TGTCTCTGCTGAGTTAAAGAAAGCAAGTAAACGC | 33950 |
| 1637 | ATTTATAAGCAATAGTAGCTTATTTGGCTCACAGTTCTGGAGGCTGA GAAGATCGTGAGGCTGCATCTGGCAAGGGCCTTCTTGCTGCTTCATA ACATGGCAGAAGACATCATGCGGGTGTGTGTCTGGGGAAGAGACTT ACAGAAGTGGAGTTGCTGAGTCAAAGATCTAACC | 33951 |
| 27147 | TCTTTTGGTGCAGAAGGTGACGGGAAACAGGCCGCAGACCTGAACT TCCAACCGTATGTAGGCGAGAAGCCGGTGCCGATACTCCCACTATCC CACAATGTCCCACTGGGCCCCAGAGTGGAAGAGGGCGGAGGCTAAT CCAAGAGACCTTGGGGCCAGCTGGGATGTCAGGGG | 33952 |
| 7408 | ATCCACCATGAAGCAGAATCTAAAGAAAAAGGTCCAAGCATGAAGG AACCAAATCCAATTTCTCCACCAATTTTCCATGGTCTGGACACCCTA ACCGTGATGGGCATTGCGTTTGCAGCCTTTGTGATCGGAGCACTCCT GACGGGGCCTTGTGGTACATCTATTCTCACACA | 33953 |
| 29135 | CAGATTAGAGGACGGGCGCTTTGGAGCCGGCCCCAGGCAGCGTGTG TCGGTCGCCTAGTCTGGAGAACTAGTCCTCGACTCACGTGCAAGGAT GATGCTGAAAGGAATAACAAGGCTTATCTCTAGGATCCATAAGGCC AAGCATGGGGATCAGCACGAGGGTCAGCACTACAA | 33954 |
| 7806 | CTCTCGGGGGCCAGGGGTCATCGGTTTGACCCCTGACCTATAAGCCA AGATACCCCATAAACACACTCAGAAAGCAGAGAAAAAGGACAAGA GTCTGTGTTTGAGAGGGGGTCTGCCATTCCTGCTTGGGGACTGGTGG GGAAGAGGGCCAGGACATCTTCTGAGCCAGGACGT | 33955 |
| 661 | AGTCTGGCTGCGGCGGCAGAGCTGAAGTGAGCGGAGCCACCAGGAG GCCATGTCGGGTGAGGACGCTGAGGTCCGGGCAGTCTCTGAAGATG TCTCCAATGGAAGCAGTGGCTCGCCCAGCCCTGGGGACACACTGCCC TGGAACCTTGGGAAAACGCAGCGGAGCCGGCGCAG | 33956 |
| 1258 | ATCTGCCTCAGCCTCTTTGTCACTGCCTGGACCATTGTCCCTGCTGTT TCTCAGACAGCATAGAGGCTGAGGCTGGGGCCAGGACCCAGACAGA GACACACGGTCACTGCAGCTGAAGCCGCTGCCCCTGCTACAGGCAC CACCAGGACCAGCTGATCATTCCAGCCCACAGCA | 33957 |
| 6757 | CTCAGGCTGTGGCCCCACCTGCCCCCAAGCCCACCCAGGCTGGGGA AGGAACGCTGTCAGAGGCCCTGCTGCAGCTGCAGTTTGATGATGAA GACCTGGGGGCCTTGCTTGGCAACAGCACAGACCCAGCTGTGTTCAC AGACCTGGCATCCGTCGACAACTCCGAGTTTCAGC | 33958 |
| 5825 | CTCAAGGTTTTGAAGAGACAGGGGACACGCTCTATGCCCCCTATTCC ACACATTTTCAGCTGCAGAACCAGCCTCCCCAAAAGGAATTCTCCAT CCCACGGGCCCACGCTTGGCCGAGCCCTTACAAAGACTATGAAGTA AAGAAAGAGGGCAGCTAACTCTGTCCTGAAGAGT | 33959 |
| 27115 | GCTTCCGTAGAGGCCAGCTGGTTGCTACGCAGCAACAGGAAACATT CCGCGCTACCGAGTACTTTCTACTCCCGACCAGGCATTGCTCTCTCTG GAGACCCTCGGCGGTGGTTGCTGTATTTTGACTTGGAGTAAGGATGA CTTTTCGGGCCACAGATAGTGAATTTGACCTGA | 33960 |
| 3130 | CTGGAGGGCCGCACTCCCGTTCCAGCCAGGCTGAGCCTTCTGTCCCC TGCCTCTGGGGCCTGGGAACCCCCCTTCTTCTTTCTCCTGAATGGCAC CCCGCCCTAGAATCCAGACACCGAGTTTCCCACTGTGGCTGGTTCA AGGAGCTCCCTGGTGACAGTCTGTGGCTGAGC | 33961 |

TABLE 2-continued

Illustrative Sequences Encoding IRES sequences

| Oligo-nucleotide Identifier | Sequence | SEQ ID NO: |
|---|---|---|
| 5065 | TAGAGTGGGGGGTGGAAGATGATTCTCGCCTGTTGCTGGGGATTTAT GAACATGGCTATGGAAACTGGGAGTTAATTAAAACAGACCCAGAGC TTAAATTAACTGACAAAATTCTGCCGGTGGAGACAGATAAAAAGCC TCAGGGGAAGCAGCTACAGACCCGAGCGGATTACT | 33962 |
| 8066 | AGCGGCTGCAGCATCCAGCCAGCTTGGATGTCTGGCCTGTGAGCCTG GGGAAACTATTATTAATAATATTTACTGTTGATAATATTGGGGAAAA CAGCCCTTAACTCTGAGGTTTCTGCTGTGCTCCTTTCCAAAACAGACT TCCAGGACTCTGAAGAAACAGTTACAAGCAGG | 33963 |
| 1952 | AAGGGAGGAGGCGCCGAGCTGACCGGGCGACGCCGCGGGAGGTTCT GGAAACGCCGGGAGCTGCGAGTGTCCAGACACTTCCCTCTGTGACC ATGAAACTCTGGGTGTCTGCATTGCTGATGGCCTGGTTTGGTGTCCT GAGCTGTGTGCAGGCCGAATTCTTCACCTCTATTG | 33964 |
| 5020 | GCGAACTGAAGGTGGCCCAAGGGAAGGCTCTGCAAGAGAATTTGGC CCTCCTGACCCAGACCCTAGCTGAAAGAGAAGAGGAGGTGGAGACT CTGCGGGGACAAATCCAGGAACTGGAGAAGCAACGGGAAATGCAG AAGGCTGCTTTGGAATTGCTGTCTCTGGACCTGAAGA | 33965 |
| 8766 | AGGAAGCCGAGGAAGGCTGTGTTTCTGACTCACACGGGGGAGTCGG GGGAGTCGTAAACAACCCTGAAGAGAACAGCCAGGCCTGGCGCTCT GGGCTTGGTCCTGGGACACCCGTTTGACACTGTAAAGGTGAGGCTGC AGACCCAGACCACCTACCGGGGCATCGTTGATTGC | 33966 |
| 27433 | CTGCCTCCCCCCCGCTCCCGCTCCCCTGAGCCCAGCCAGACCCCGCG CCGCCCGCGCCCCGCTCGACTCCGGAGGCTCCCGCAGCCCGGCGTC CGCCCCGCTGCCCCCTCCCCCGGGGGCCATGGGGGCGCCCCCGGGCT ACCGGCCCTCAGCTTGGGTGCATCTCCTCCACC | 33967 |
| 27818 | CTCAGTGAAGCAACGAGGATGCCGGGGAGAGGGAAGGGGCTGGGC TCTGGGCGGTGCCAAGTCTGTGAGGGGGCGCGGTCACCGCCCAGGG TTCCCACGAACGCCAAGGCGGCCACGTCCTGCTCCCCCTGGTGAAGA AGCTGCCCTGGGCTTGTCGTCCTAGGGTCTCCAGAC | 33968 |
| 8861 | CTGATGTGAGCTAGTTTGTCTGGTTGAGTTGGATGTTTAAATAGAAG GCAGAACAACAACAGGTACTCCACATCAGCATTCTCAAGACTGGAG AAGTTAGGCCTCAGACATCCCAAGCCTTCTCCTTTCATTGGAAACTT GACATTTTTCCGCCAGGGTTTTTGGGAAAGCCAA | 33969 |
| 8040 | GCCACATTCCACACTAACGTGTTGGTGAATTCTTCTGGGCATTGCCA GTACCTGCCTCCAGGCATATTCAAGAGTTCCTGCTACATCGATGTAC GCTGGTTTCCCTTTGATGTGCAGCACTGCAAACTGAAGTTTGGGTCC TGGTCTTACGGAGGCTGGTCCTTGGATCTGCAG | 33970 |
| 27907 | TCCTGCCTCGGCAACCCCGGGCCCTGAGGGCAGGCCCCAACCGCGG AGGAGCAGGAGAGGGCGGAGGCCGGCGGGCCATGCCCTGGTCGTCC CGCGGCGCCCTCCTTCGGGACCTGGTCCTGGGCGTGCTGGGCACCGC CGCCTTCCTGCTCGACCTGGGCACCGACCTGTGGG | 33971 |
| 2392 | AAGTTTGAAACTGGTAACTTCGGGAGTTGAGCCACGAGCTGTTGTGC ATCCAGAGGTGGAATTGGGGCCCGGCATTCCCTCCTCGTCCCGGGCT GGCCCTTGCCCCCACCCTGCAACTCCTGGTTGAGATGGGCTCAGCCA AGAGCGTCCCAGTCACACCAGCGCGGCCTCCGC | 33972 |
| 7802 | AGCCTTCGCTGGATCTCCTTCCCGAACTCACAAATCCTGACGAGCTC CTGTCTTATCTGGACCCCCCCGACCTGCCGAGCAATAGTAACGATGA CCTCCTGTCTCTATTTGAGAACAACTGAGGGCCACCCGGTCGGGGCC ATCCCTCCACACTCTGCATCCTACCCCACCTAC | 33973 |
| 7655 | TTTTTAGAGGTTGGTTGTTGTGTTTTAGGATTCTGTCCATTTTCTTTTA AAGTTATAAACACGTACTTGTGCGAATTATTTTTTTAAAGTGATTTGC CATTTTTGAAAGCGTATTTAATGATAGAATACTATCGAGCCAACATG TACTGACATGGAAAGATGTCAAAGATATGT | 33974 |
| 981 | AGCCAGCGGACGTCCAGGAACCGGGATGCCTCCAGCAGTGAGGCGG TCAGCCTGCAGCATGGGATGGCTGTGGATCTTTGGGGCAGCCCTGGG GCAGTGTCTGGGCTACAGTTCACAGCAGCAAAGGGTGCCATTTCTTC AGCCTCCCGGTCAAAGTCAACTGCAAGCGAGTTA | 33975 |

TABLE 2-continued

Illustrative Sequences Encoding IRES sequences

| Oligo-nucleotide Identifier | Sequence | SEQ ID NO: |
|---|---|---|
| 5027 | GGGACCAGGAACTGGAGGCTCTGCAGCAAGAACAGCAGCAGGCCCAGGGACAGGAGGAGAGGGTGAAGGAAAAGGCAGACGCCCTCCAGGGAGCTCTGGAGCAAGCCCATATGACACTGAAGGAGCGTCATGGAGAGCTTCAGGACCACAAGGAACAGGCACGAAGGCTGGAGG | 33976 |
| 7683 | CTACTCCGGAGCCTGAGGTGGGAGGATCGCTTGAGTCTGGGAGGCAGAGGCTGCATTGAGCTATGATCATGGCACTGCATTCCAGCCTGGGTGACAGTGCAAGACCTTGTCTCAGAATAAATAAAGTATGTGATGAAGATGTGCATACATTATATGCAAATACTGTTTTTTTTT | 33977 |
| 8650 | CACCAATTCGGCTGGCGTCTCCGAGACCGCGGACTCCCGTAGGGTCCCCGTGGCCCCGAGTTGTAGTCGGGACACCCCGGCCGCGGGTGATCGTCGGGTCTCCACGCGCCCGGGTCGCTGACGCGGATCCGGCCTCGGCGCCTTCTCAGGGCGCCCTGCAAGGCCGCAGGCAGG | 33978 |
| 6898 | CCTCCTCTCTGGCTAATCAACAGCTGCCCCCAGCCTGTGGTGCCAGGCAACTCAGCAAGCTGAAAAGGTTCCTTACTACCCTGCAGCAGTTTGGCAATGACATTTCACCCGAGATAGGAGAAAGAGTTCGCACCCTCGTTCTGGGACTAGTGAACTCCACTTTGACAATTGAAG | 33979 |
| 2042 | TTTAGTGTCACAGGAGACACGAGGGCAAAGTGCTGAGGAAACTCTAGAGCAACATCGGAATGCATGGTGAAGCATCAGATGGTGAAGGAGAAGGAGACACAGAAGTGATGCAGCAGGAGACAGTTCCAGTTCCTGTACCTTCAGAGAAAACCAAACAGCCTAAAGAATGTTTTT | 33980 |
| 1686 | GCCACTTCTCTTCCCTTCATTCTTCGCCAGGCTCTCTGCTGACTCAAGTTCTTCAGTTCACGATCTTCTAGTTGCAGCGATGAGTGCACGAGTGAGATCAAGATCCAGAGGAAGAGGAGATGGTCAGGAGGCTCCCGATGTGGTTGCATTCGTGGCTCCCGGTGAATCTCAGCA | 33981 |
| 5902 | CTTCAACTTGGCAACAGTTGCCTGGGGTAGCTCTACACAACTCTGTCCAGCCCACAGCAATGATTCCAGAGGCCATGGGAGTGGACAGCAGCTAGCTGACTGGAGGAATGCCCACTCTCATGGCAACCAGTACAGCACTATCATGCAGCAGCCATCCTTGCTGACTAACCATG | 33982 |
| 3399 | CACCCTGACCCAAGCCGAGACAGGTTCCAAACCTCAACCTGCAGCCGGAAGGGGGAAGTGAAACTCGGCTGGGGGTGGGGGCTCAGAAGCCGCCCCAGAAAGCACTGAAAGCCACAGCACGTACACCCACTCCAGGGATCTGCCAGCACCCTGTGGGGCCCAGACTACAGGCTG | 33983 |
| 6560 | GGGACGCCATTGTGATTGGGGCGGGGATCCAGGGCTGCTTCACTGCATACCACCTGGCCAAACACAGGAAGAGGATCCTCCTGCTGGAGCAGTTCTTTCTACCACACTCCCGAGGAAGCTCCCATGGACAAAGCCGGATAATCCGAAAGGCGTACCTGGAAGACTTTTACACCC | 33984 |
| 2890 | CACCGTAGTGCTTAGAGGCCGAAAAAGTACAGCCCCTTCCGGGCTCCGCGGTACGGGAAGACAGCTTTGGGATGTCGGAAGATCCTAGAGGTCCCAAGGTACCACGAAAGGCAGTGGTAGAAAAGCCAGCTCGGGCAGCAGAGCGAGAGGCCCGGGCCCTGCTGGAGAAGAACC | 33985 |
| 4343 | ATTGGCTGAGCCCGGCTGTCAGTCCTTTCGCGCCTCGGCGGCGCGGCATAGCCCGGCTCGGCCTGTAAAGCAGTCTCAAGCCTGCCGCAGGGAGAAGATGGCGGTCGCCGTGAGAACTTTGCAGGAACAGCTGGAAAAGGCCAAAGAGAGTCTTAAGAACGTGGATGAGAACAT | 33986 |
| 6138 | ACAAGGAGACTGGGAGGTGTCTCAAGTGCCTGTACCACACGGAAGGGGAACACTGTCAGTTCTGCCGGTTTGGATACTATGGTGATGCCCTCCAGCAGGACTGTCGAAAGTGTGTCTGTAATTACCTGGGCACCGTGCAAGAGCACTGTAACGGCTCTGACTGCCAGTGCGACA | 33987 |
| 2241 | GAGGAAGGAGAGAGTGGAGGAGGAGGGCTTTGGGTTAGGGAGAGTGCTTTCGTTTGTTTTAAATGGGAGAAACTGGAGCATGTTGCCAAGGGCAGAGAGCCAGCAGAGAGGGGTGAATGAAGAAGGAGCGAGAAGGGGGTTACTGACGAAGCCTTATCCTGGAGGAGAGAAGG | 33988 |
| 5715 | CAAGTGGTCCTGTCGAAGTATTTATCACTGAGACTCCGAGTCAGCCCAACTCCCACCCCATCCAGTGGAATGCACCACAGCCATCTCACATTTCCAAGTACATTCTCAGGTGGAGACCTAAAAATTCTGTAGGCCGTTGGAAGGAAGCTACCATACCAGGCCACTTAAACTCCT | 33989 |

TABLE 2-continued

Illustrative Sequences Encoding IRES sequences

| Oligo-nucleotide Identifier | Sequence | SEQ ID NO: |
|---|---|---|
| 3456 | CTAGACCAAAGGGTGCGGCTGCTGCAGAGGTGGCTGATGCAGGTTT CCATCCTTGGGGAATGACCACGCAACTGGGCCCAGCCCTGGTGCTGG GGGTGGCCCTGTGCCTGGGTTGTGGCCAGCCCCTACCACAGGTCCCT GAACGCCCCTTCTCTGTGCTGTGGAATGTACCCT | 33990 |
| 5260 | ATCTCCAGCCATTGCTCCTCCAACAGAGACCATGGCTCCTCCAGTCA GGGATCCTGTTCCTGGGAAACCCACGGTCACCATCCGGACTCGAGGC GCCATTATTCAAACCCCAACCCTAGGCCCCATCCAGCCTACTCGGGT GTCAGAAGCTGGCACCACAGTTCCTGGCCAGAT | 33991 |
| 1288 | GGAGGCAGGCGGTGCCGCGGCGCCGGGACCCGACTCATCCGGTGCT TGCGTGTGGTGGTGAGCGCAGCGCCGAGGATGAGGAGGTGCAACAG CGGCTCCGGGCCGCCGCCGTCGCTGCTGCTGCTGCTGCTGTGGCTGC TCGCGGTTCCCGGCGCTAACGCGGCCCCGCGGTCG | 33992 |
| 8756 | CACCCCCACCGACCTCTCGGAGACAGGAATCCGCTCTGCCCCTGCAT CCTCCTCTGCTCACCCTTCTCTCAGTAGTGTTTGTCAGACACCAGTCC GGACCTCAGCTCTCGATCTAGTTCCCGAGTAAGATTTAGCTCCCGGG AAAGCGTGCCTGAAACAAGCCGGAGTGAGCCT | 33993 |
| 8952 | CCTGTACCATAACCAGGAGGCTGATGGTTGCTCAGGCCTCCCTCAAA CTAGCCAATGAGAAGTGCACGGGTCCTGGTCGCCTAGGAAACCGCG TGACAACAAGATGGCGGCGCTGCGGGACGGCTAGCGGCCCTGCGTG GGAGTTCCTGACAGCTGGATTCTAGAAGTAGAACT | 33994 |
| 2759 | TTCCCCGGAAGTGTTGGTTAAAGCCCCTCCAATCAGCGGCTCGGTGC GGCAAGTTTGAATTTCGTGGAGGCTCGGGTTGTGAGGGTTCCTGCTT CGGAGTCGGCGGTGGTCGTCCAGACCGAGTGTTCTTTACTTTTTGTTT GGTTGAGGTTTCACGCTAGAAGGTGGCTCAGG | 33995 |
| 1241 | CTGTCCATACACTCTCTCATCATCCTGTTCCTTGGATTGGACTTCACT AAGCAATTTATCACTCACCTTCAGACTTACATGTGGGAGTTTTCACA ACAGTAGTTTTGGAATCATTAGAACTTGGATTGATTTCATCATTTAAC AGAAACAAACAGCCCAAATTACTTTATCACC | 33996 |
| 28013 | GAGCTCCAGCCTCCAGGCACCCGGGATCCAGCGCCGCCGCTCATAA CACCCGCGACCCCGCAGCTAAGCGCAGCTCCCGACGCAATGGACCC GGCGCTGGCAGCCCAGATGAGCGAGGCTGTGGCCGAGAAGATGCTC CAGTACCGGCGGGACACAGCAGGCTGGAAGATTTGC | 33997 |
| 4681 | TGTTGACTCATGCAAATGAGGTATCTGAACTGCAGCTTCAGTATTAG CAGAGCCACAGGCCGCCTCTGTGGCATCACCAGGGTTTCTCTGAAGA AGAGGGTCTGCATTTTCCTAAACCCAGTGCTGCTCTCCCATCTCCCAT CTTCCTCTCGCAGCTTGATGAGCCCCGGTGTG | 33998 |
| 5602 | TGCCCCAGCCCTCAGGGCCGCCAGCAAGGAAGAAATTTGTGATACC CCTCGACGAGGATGAGGTCCCTCCTGGAGTGGCCAAGCCCTTATTCC GATCTACACAGAGCCTTCCCACTGTGGACACCTCGGCCCAGGCGGCC CCTCAGACCTACGCCGAATATGCCATCTCACAGC | 33999 |
| 1945 | GAGAGGCCGGCGTCTCTCCCCCAGTTTGCCGTTCACCCGGAGCGCTC GGGACTTGCCGATAGTGGTGACGGCGGCAACATGTCTGTGGCTTTCG CGGCCCCGAGGCAGCGAGGCAAGGGGGAGATCACTCCCGCTGCGAT TCAGAAGATGTTGGATGACAATAACCATCTTATT | 34000 |
| 5229 | AACCCCAACCCTAGGCCCCATCCAGCCTACTCGGGTGTCAGAAGCTG GCACCACAGTTCCTGGCCAGATTCGCCCAACGATGACCATTCCTGGC TATGTGGAGCCTACTGCAGTTGCTACCCCTCCCACAACCACCACCAA GAAGCCACGAGTATCCACACCAAAACCAGCAAC | 34001 |
| 7542 | CTGCAGCATCTTCTACGTCGGGACCACAGCCTCCGCCTCCACAAAGC CTGAACCTCCTTTCGCAGGCTCAGCTGCAGGCACAGCCTCTTGCGCC AGGCGGAACTCAAATGAAAAAGAAAAGTGGCTTCCAGATAACTAGC GTTACTCCTGCTCAGATCCCGCTAGTATCAGCT | 34002 |
| 6866 | CCAATACCTGGGATCCATTGCCTCTCCTTCTGTGCACCCAGCAACGC CCATTTCACCTGGACGTGCCAGCGGCATGACAACCCTCTCTGCAGAA CTTTCCAGTCGACTCTCAACGGCACCCGACCTGACAGCGTTCAGCGA CCCGCGCCAGTTCCCCGCGCTGCCCTCCATCTC | 34003 |

TABLE 2-continued

Illustrative Sequences Encoding IRES sequences

| Oligo-nucleotide Identifier | Sequence | SEQ ID NO: |
|---|---|---|
| 1849 | TCTCTTGCTTCAACAGTGTTTGGACGGAACAGATCCGGGGACTCTCT TCCAGCCTCCGACCGCCCTCCGATTTCCTCTCCGCTTGCAACCTCCGG GACCATCTTCTCGGCCATCTCCTGCTTCTGGGACCTGCCAGCACCGTT TTTGTGGTTAGCTCCTTCTTGCCAACCAACC | 34004 |
| 2558 | AGTTACCTCTCCCCTTTCACGTAGTTTTCATTTGTGGTGAGATTCTCT CCCAGGCCACAAGACATTTCCTGCTCGGAACCTTGTTTACTAATTTC CACTGCTTTTAAGGCCCTGCACTGAAAATGCAAGCTCAGGCGCCGGT GGTCGTTGTGACCCAACCTGGAGTCGGTCCCG | 34005 |
| 2109 | ATCAGCCCAAAGGTAGGCTCAGGCTCCGACGGTGGCCGGCGGGGGT CACGAGGCTTCGTAGTGGAGGAACGGGTTTGGCGTGTGGGACGCAG CTGCCTCTGTACTGGGGAGTCACGGAGTGGCCGGGCTCCAGGGACA TGGCGGCGGCCTCTGCGGTGTCGGTGCTGCTGGTGG | 34006 |
| 297 | ATCCGGAGGCAGCCTGCAGGAAGCCGTAGCGCCGGTACGTGCCCCT CTCCTGTCTGGAGGCGGGTGTAGAAGTCCGACCGCGGAAGCCAGAC TGCTGTCCAGTCGGCGAGCGCGTACCATTCAGCATCGGCTCCGCCCG AGTCCCACCTTCCTCAGGCTCTGATTGGCTGACAC | 34007 |
| 2621 | CAACAGAAGCCAAGAAGGAAGCCGTCTATCTTGTGGCGATCATGTA TAAGCTGGCCTCCTGCTGTTTGCTTTTCATAGGATTCTTAAATCCTCT CTTATCTCTTCCTCTCCTTGACTCCAGGGAAATATCCTTTCAACTCTC AGCACCTCATGAAGACGCGCGCTTAACTCCGG | 34008 |
| 6574 | TGGCTGACACATTCCTGGAGCACATGTGCCGCCTGGACATTGATTCA CCACCCATCACAGCCCGGAACACTGGCATCATCTGTACCATTGGCCC AGCTTCCCGATCAGTGGAGCTGAAGAAGGGAGCCACTCTCAAAATC ACGCTGGATAACGCCTACATGGAAAAGTGTGACG | 34009 |
| 1033 | GACATTTACATCCTGCCCAGCGACAACTCTGGACAAGTCAGTCCCCC AGAGTCTCCAACTGTGACCACTTCCTGGCAGTCTGAGAGCTTACCTG TGTCACTGTCAGCTAGCCAGAGTTGGCACACAGAAAGCCTGCCAGT GTCACTAGGCCCTGAGTCCTGGCAGCAGATTGCA | 34010 |
| 8789 | CCTCTGACTTGACCCAATGAAAGAAGCATATGGCACTTGTGAAGATA AATGTTACTCCTCCCTTTTTAATTGGAACTTCTGCTTAGGACCTGTGT ATGACGTTTCACCTGTGATCTGTTCTTTCGGTAGCCACTGACTTTGAG TTACAGGAAGGTCTCCGAAGATTTGTGTCAA | 34011 |
| 6392 | CTTCCCTGAGGAGGACGACCCCACCAACTGGCTGCGTTGCTACTACT ACGAAGACACCATCAGCACCATCAAGTCTGTGGCCTGGGAGGGAGG GGCCTGTCCAGCCTTCCTGCCATCCCTACGACCACTGCCCCCTCACAT CACCTTCTCATGGGTCCCTCTCCCACTCCAAAGC | 34012 |
| 6885 | ATTTATGATTTCAACATGGATACATATTTCAGTTCTTTCTTTTTCTCAC TATCTGAAAATACATTTCCCTCCCTCTCTTCCCCCCAATATCTCCCTT TTTTTCTCTCTTCCTCTATCTTCCAAACCCCACTTTCTCCCTCCTCCTT TTCCTGTGTTCTCTTAAGCAGATAGCAC | 34013 |
| 561 | CCCTTCCGGCTGGCCCCGCTCAGTCACCCGCAGCAGGCGTGCAGTTT CCCGGCTCTCCGCGCGGCCGGGGAAGGTCAGCGCCGTAATGGCGTT CTTGGCGTCGGGACCCTACCTGACCCATCAGCAAAAGGTGTTGCGGC TTTATAAGCGGGCGCTACGCCACCTCGAGTCGTG | 34014 |
| 7556 | ATACAAATTTGCCTTTGGCACAACAGATACCACTAAGTTCTACCCAG TTCTCCGCACAATCATTAGCTCAGGCAATTGGAAGCCAAATTGAAGA TGCCAGGCGTGCAGCGGAGCCCTCCTTAGTTGGCTTACCTCAGACTA TCAGTGGTGACAGTGGGGGAATGTCAGCAGTTT | 34015 |
| 8800 | TCCGTCCTCCAGGATCTGGGGAGAAAGAGCCCCATCCCTTCTCTCTC TGCCACCATTTCGGACACCCCGCAGGGACTCGTTTTGGGATTCGCAC TGACTTCAAGGAAGGACGCGAACCCTTCTCTGACCCCAGCTCGGGCG GCCACCTGTCTTTGCCGCGGTGACCCTTCTCTC | 34016 |
| 5781 | GTTTACTTCCCCTGCCAGCATTGGGGTGCTCTCTAAGCAACAGTAGG CGGAGAGTGGTCTGGCGTATTAAAAACAAAGGATCGTCAAGTGGGC CTTCCAGGCATTGCTTTGACTTAGTACATGTAGAGGATGTGGCAGT TCTCTCCGTCCCTGCCACTGCTGGTTTCTTTGTT | 34017 |

TABLE 2-continued

Illustrative Sequences Encoding IRES sequences

| Oligo-nucleotide Identifier | Sequence | SEQ ID NO: |
|---|---|---|
| 2930 | TATTTTAAGCCCAGTCTTCCCTGGGCCACCTTTAGCAGATCCTCGTGC GCCCCCGCCCCTGGCCGTGAAACTCAGCCTCTATCCAGCAGCGACG ACAAGTAAAGTGGCCCGCCGGTTTCTGAGCCTTCTGCCCTGCGGGA CACGGTCTGCACCCTGCCCGCGGCCACGGACC | 34018 |
| 3426 | CCAGCGGAAGTAATTCTTTCGACTGCCCCGGAACCCACCGGAGCAG GCAGCTGGGGGTGGGGGGCGGCCCTGGGATAGGGGCTGTGGCAGT ACGCGGGGACCCGGCTGCGGTGGCTGCGGGACTGACGAATGGAGAG GAGAAAACCTATGGTGGCTGTGAAGGACCTGATGCC | 34019 |
| 5800 | ATGGGGAAGGTGAAGGTCGGAGTCAACGGATTTGGTCGTATTGGGC GCCTGGTCACCAGGGCTGCTTTTAACTCTGGTAAAGTGGATATTGTT GCCATCAATGACCCCTTCATTGACCTCAACTACATGGTTTACATGTTC CAATATGATTCCACCCATGGCAAATTCCATGGC | 34020 |
| 27433 | CTGCCTCCCCCCGCTCCCGCTCCCCTGAGCCCAGCCAGACCCCGCG CCGCCCGCGCCCCGCTCGACTCCGGAGGCTCCCGCAGCCCCGGCGTC CGCCCCGCTGCCCCCTCCCCGGGGGCCATGGGGGCGCCCCCGGGCT ACCGGCCCTCAGCTTGGGTGCATCTCCTCCACC | 34021 |
| 424 | ATTTCTGGGAAGCAGTCGATATTATCTGTACGCCTAGAACAGTGCCC TCTGCAGCTGAATAACCCTTTTAACGAGTATTCCAAATTTGATGGCA AGGGTCATGTAGGTACAACAGCAACCAAGAAGATCGATGTCTACCT CCCTCTGCACTCGAGCCAGGACAGACTGCTGCCA | 34022 |
| 28259 | CTCTGGTGATACAGAAGAAAAGACAGTCTCCATTTTCAAACAGTCCC TCCTGGGAGAACACAGACAGGCAGAGGATTACAACACAAGGCAGCA AGCACTGGGAGACGAAAGTTTTGGCATCTGTTCCCTGGCTGTGCCAA GATGGGCGATTGGAGCTTCCTGGGAAATTTCCTG | 34023 |
| 6972 | GTCTACTATGTCTGAACTGTGGTTTCTTGTTTATCCTTTTTTCCTTAGT TGGACTGTAATGTATGGTCTGTCAACCTGTGAATCTTTAAAGTATGA TTCAGGTATTGTTGTATTCTTTACTGTGTAATAAAAAAGTTGAAAAA AATCTGGATCCTCTGTCTCCCTCGTCCCCGG | 34024 |
| 417 | TTTCGTGACCTTGTCCAGTAGAAGGCTATTTAATTTTCACAACTGCTT GAATTTTGACATACAAGATGAAGCAAGATGCCTCAAGAAATGCTGC CTACACTGTGGATTGTGAAGATTATGTGCATGTGGTAGAATTTAATC CCTTTGAGAATGGGGATTCAGGAAACCTAATTG | 34025 |
| 8182 | TGTCTGCACCAGCCGGCCTCCAGCCTGGCTGGACCCTGCTGCCTGTG TGGCCCGGAGCCAGAGGCCCCCACACTCCCAGCTGCTCTTCTACAGA TGCCATCAACGAGCAGGACTCTGGGTGGCTCCACTGTCTAAGGGCTC TGCGAGTGACCCGGCGGGCGAGCTCCGTGCTGC | 34026 |
| 7572 | CTTACGTAGTAATTACATTTCCTTGAAAAAACTATAGTGAATAGAAA TCCCTAGCCATTTCATTTTTTATGTTTTTAATGAAGATCTTTAAAATA CCATAGGTGGTAATCGTGGAAAATTTGAAAAATCTCATGTCAGTGTA TTAAGATGGTGGAGAAGTTTTTTTCTCCATTA | 34027 |
| 1415 | ATTCATGAAAATCCACTACTCCAGACAGACGGCTTTGGAATCCACCA GCTACATCCAGCTCCCTGAGGCAGAGTTGAGAATGGAGAGAATGTT ACCTCTCCTGGCTCTGGGGCTCTTGGCGGCTGGGTTCTGCCCTGCTGT CCTCTGCCACCCTAACAGCCCACTTGACGAGGA | 34028 |
| 7327 | GAGCTTCCAGGGATATTTGAGGCACCATCCCTGCCATTGCCGGGCAC TCGCGGCGCTGCTAACGGCCTGGTCACATGCTCTCCGGAGAGCTACG GGAGGGCGCTGGGTAACCTCTATCCGAGCCGCGGCCGCGAGGAGGA GGGAAAAGGCGAGCAAAAAGGAAGAGTGGGAGGA | 34029 |
| 705 | GCCCCCTCCCCTGACTATCAAAGCAGCGGCCGGCTGTTGGGGTCCAC CACGCCTTCCACCTGCCCCACTGCTTCTTCGCTTCTCTCTTGGAAAGT CCAGTCTCTCCTCGGCTTGCAATGGACCCCAACTGCTCCTGCGCCGC TGGTGTCTCCTGCACCTGCGCTGGTTCCTGCA | 34030 |
| 8561 | AGTCGCATAGTGGTTTTTCCGCTCGCGTCGCTGTGTGAAAGTTGGCT CGCCGCTCTTTGCACGCCCTCCCTGGAGGCCGACCCGAGACGCCAAG CTGGAGAGACCGTGCCTCCCCGAGGCCGGCCGCCCCGCGAGCACAG CCTCCGCCCCCGTTGCACTGCCGGGCTGGGCAAT | 34031 |

TABLE 2-continued

Illustrative Sequences Encoding IRES sequences

| Oligo-nucleotide Identifier | Sequence | SEQ ID NO: |
|---|---|---|
| 1679 | GGTGGCGGGAAGAGGAGGCGCGAGAATGGAGGTGGAGGCCGTCTG TGGTGGCGCGGGCGAGGTGGAGGCCCAGGACTCTGACCCTGCCCCT GCCTTCAGCAAGGCCCCCGGCAGCGCCGGCCACTACGAACTGCCGT GGGTTGAAAAATATAGGCCAGTAAAGCTGAATGAAAT | 34032 |
| 5635 | TATTTCCCTCTACTGAGTAAACCCTATCTGTGATTCCCCCAAACATCT GGCATGGCTCCCTTTTGTCCTTCCTGTGCCCTGCAAATATTAGCAAA GAAGCTTCATGCCAGGTTAGGAAGGCAGCATTCCATGACCAGAAAC AGGGACAAAGAAATCCCCCCTTCAGAACAGAGG | 34033 |
| 5583 | TGTTACTTAAGAATGCTTTCCAGGTGGAAAGTTCCTTAAGTTTGAGG CTTCAAATTCCATACAGCACATTAAAATCCCATTCATGAGTTTGAAA TACTGCTCTGTTGTCTTGGAAATACCAATCAGATTGTTGGCTGAAGT GATGTGGATAAAGAAGGGATCTTAGAAAAACTA | 34034 |
| 9027 | ACGAAGTTCCGGAAATGGAATTACCGAGTCAGATGAGAAACACAAG TCATCAATGAATTAACAAGCAACACATTGTCACATCCAGCTGTTGAA GAGTGGTTAACTCAGCTTGATCTCCGAAGACTCTTCTGCACCCCACC CCGCCCCCAACTGCTTTCCAAAGAGAAACAGAAA | 34035 |

The IRES may be of any length or size. For example, the IRES may be about 100 nucleotides to about 600 nucleotides in length (e.g., about 200, about 225, about 250, about 275, about 300, about 325, about 350, about 375, about 400, about 425, about 450, about 475, about 500, about 525, about 550, or about 575 nucleotides in length, or a range defined by any two of the foregoing values). In some embodiments, the IRES may be about 200 nucleotides to about 800 nucleotides in length (about 200, about 210, about 220, about 240, about 260, about 280, about 320, about 340, about 360, about 380, about 420, about 440, about 460, about 480, about 500, about 520, about 540, about 560, about 580, about 600, about 620, about 640, about 660, about 680, about 700, about 720, about 740, about 760, about 780, or about 800 nucleotides in length, or a range defined by any two of the foregoing values). In some embodiments, the IRES may be about 200 to about 400, about 400 to about 600, about 600 to about 700, or about 600 to about 800 nucleotides in length. In some embodiments, the IRES is about 210 nucleotides in length. In some embodiments, the IRES may be about 100 to about 3000 nucleotides in length.

In some embodiments, a circular RNA molecule comprises of an IRES sequence that consists of a sequence encoded by a DNA sequence of any one of SEQ ID NO: 1-228 or SEQ ID NO: 229-17201. In some embodiments, a circular RNA molecule comprises an IRES sequence encoded by a DNA sequence of any one of SEQ ID NO: 1-228 or SEQ ID NO: 229-17201, wherein the IRES sequence additionally comprises up to 1000 additional nucleotides. In some embodiments, the IRES sequence is encoded by a sequence of any one of SEQ ID NO: 1-228 or SEQ ID NO: 229-17201 and additionally comprises up to 1000 additional nucleotides located at the 5' end of that sequence. In some embodiments, the IRES sequence is encoded by a sequence of any one of SEQ ID NO: 1-228 or SEQ ID NO: 229-17201 and additionally comprises up to 1000 additional nucleotides located at the 3' end of that sequence. In some embodiments, the IRES sequence is encoded by a sequence of any one of SEQ ID NO: 1-228 or SEQ ID NO: 229-17201 and additionally comprises up to 1000 additional nucleotides located at the 5' end of that sequence and up to 1000 additional nucleotides located at the 5' end of that sequence.

In some embodiments, a circular RNA molecule comprises an internal ribosome entry site (IRES) sequence region, wherein the IRES sequence region comprises a sequence encoded by a DNA sequence of any one of SEQ ID NO: 1-228 or SEQ ID NO: 229-17201, and wherein the sequence encoded by a DNA sequence of any one of SEQ ID NO: 1-228 or SEQ ID NO: 229-17201 has a minimum free energy (MFE) of less than −18.9 kJ/mol and a melting temperature of at least 35.0° C.

In some embodiments, a circular RNA molecule comprises an internal ribosome entry site (IRES) sequence region, wherein the IRES sequence region comprises a sequence encoded by a DNA sequence of any one of SEQ ID NO: 1-228 or SEQ ID NO: 229-17201, and wherein the IRES sequence region has a minimum free energy (MFE) of less than −18.9 kJ/mol and a melting temperature of at least 35.0° C., over its entire length.

In some embodiments, a circular RNA molecule comprises an internal ribosome entry site (IRES) sequence region, wherein the IRES sequence region comprises a sequence encoded by a DNA sequence of any one of SEQ ID NO: 1-228 or SEQ ID NO: 229-17201, and additionally comprises up to 1000 additional nucleotides located at the 5' end of and up to 1000 additional nucleotides located at the 5' end, and wherein the IRES sequence region has a minimum free energy (MFE) of less than −18.9 kJ/mol and a melting temperature of at least 35.0° C., over its entire length.

In some embodiments, the recombinant circular RNA molecule comprises a protein-coding nucleic acid sequence operably linked to the IRES in a non-native configuration. Any protein or polypeptide of interest (e.g., a peptide, polypeptide, protein fragment, protein complex, fusion protein, recombinant protein, phosphoprotein, glycoprotein, or lipoprotein) may be encoded by the protein-coding nucleic acid sequence. In some embodiments, the protein coding-nucleic acid sequence encodes a therapeutic protein. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the protein-coding nucleic acid sequence can encode an antigen of a pathogen (e.g., a bacterium, virus, fungus, protist, or parasite), and the circRNA can be used as, or as one component of, a vaccine. Therapeutic proteins, and examples thereof, are further described in, e.g., Dimitrov, D. S., *Methods Mol Biol.*, 899: 1-26 (2012); and Lagassé et al., *F1000Research*, 6: 113 (2017).

Ideally, the IRES is "in-frame" with respect to the protein-coding nucleic acid sequence, that is, the IRES is positioned in the circRNA molecule in the correct reading frame for the encoded protein. Examples of IRES elements that were found to be in-frame with one or more coding sequences are set forth in SEQ ID NO: 28984-32953. In some embodiments, however, the IRES may be "out of frame" with respect to the protein-coding nucleic acid sequence, such that the position of the IRES disrupts the ORF of the protein-coding nucleic acid sequence. In other embodiments, the IRES may overlap with one or more ORFs of the protein-coding nucleic acid sequence. In addition, while in some embodiments the protein-coding nucleic acid sequence comprises at least one stop codon, in other embodiments the protein-coding nucleic acid sequence may lack a stop codon. The instant inventors have found that a circRNA molecule comprising a protein-coding nucleic acid sequence having an in frame non-native IRES and lacking a stop codon can initiate a recursive (i.e., infinite loop) translation mechanism. Such recursive translation may produce a concatenated protein multimer (e.g., >200 kDa). This particular circRNA design allows for the production of repeating ORF units up to 10 times the size of the single ORF. Without being bound to any particular theory, use of the circRNAs described herein for recursive gene encoding may represent a novel "data compression" algorithm for genes, addressing the gene size limitation associated with many current gene therapy applications.

In some embodiments, the IRES comprises (i) at least one RNA secondary structure element and (ii) a sequence that is complementary to an 18S rRNA. In some embodiments, the IRES comprises (i) at least one RNA secondary structure element and (ii) a sequence that is complementary to an 18S rRNA, wherein the RNA secondary structure of the IRES is formed from the nucleotides at about position 40 to about position 60 of the IRES, wherein the first nucleic acid at the 5' end of the IRES is considered to be position 1. The relative location of the at least one RNA secondary structure and the sequence that is complementary to an 18S RNA may vary. For example, in some embodiments, the IRES comprises (i) at least one RNA secondary structure element and (ii) a sequence that is complementary to an 18S rRNA, and wherein the at least one RNA secondary structure is located 5' to the sequence that is complementary to an 18S rRNA (See FIG. 4K). In some embodiments, the IRES comprises (i) at least one RNA secondary structure element and (ii) a sequence that is complementary to an 18S rRNA, and wherein the at least one RNA secondary structure element is located 3' to the sequence that is complementary to an 18S rRNA (See FIG. 19B).

DNA Molecules, Vectors, and Cells

In some embodiments, the disclosure provides a DNA molecule comprising a nucleic acid sequence encoding any one of the recombinant circRNA molecules disclosed herein. Accordingly, described herein are DNA sequences that may be used to encode circular RNAs. In some embodiments, a DNA sequence encodes a circular RNA comprising an IRES. In some embodiments, a DNA sequence encodes a circular RNA comprising a protein-coding nucleic acid. In some embodiments, the DNA sequence encodes a circular RNA molecule; wherein the circular RNA molecule comprises a protein-coding nucleic acid sequence and an internal ribosome entry site (IRES) operably linked to the protein-coding nucleic acid sequence in a non-native configuration. In some embodiments, the DNA sequence encodes a protein coding-nucleic acid sequence, wherein the protein is a therapeutic protein.

The DNA sequences disclosed herein may, in some embodiments, comprise at least one non-coding functional sequence. For example, the non-coding functional sequence may be a microRNA (miRNA) sponge. A microRNA sponge may comprise a complementary binding site to a miRNA of interest. In some embodiments, a sponge's binding sites are specific to the miRNA seed region, which allows them to block a whole family of related miRNAs. In some embodiments, the miRNA sponge is selected from any one of the miRNA sponges shown in Table 3, below.

TABLE 3 miRNA sponges

| miRNA | Binding sites | Cell context |
|---|---|---|
| 92, empty | four bulged sites | rat cerebellar neuronal cultures |
| miR-155, empty | eight bulged sites | B cell lymphoma cell line |
| 15a, empty | two perfect sites | human prostate cell lines, xenograft |
| 113, empty | two perfect sites | mouse cardiac myocytes, heart |
| 326, empty | seven bulged sites | tail vein injection, TH cells |
| 16, 20,21, 30-5p, CXCR4 | tour to nine bulged sites | mammalian cell lines |
| 16, 20, CXCR4 | four to nine bulged sites | mammalian cell lines |
| let-7, 22,124, 125, 132, 143, empty | five to seven bulged sties | rat hippocampal neuronal cultures |
| 183, CXCR4 | seven bulged sites | HEK293T cell line |
| A.t. 156, 319, empty | one bulged site | transgenic *Arabidopsis* plants |
| 16, CXCR4 | seven to nine bulged sites | human multiple myeloma cell lines, xenograft |
| 16, 23a, 142-3p. 221,223, nonspecific | four perfect or four bulged sites | U937 cell line, mouse hematopoietic stem/progenitor cells, transplant |
| KSHV miR-K1, CXCR4, empty | nine bulged sites | BC-3 B cell lymphoma cell line |

TABLE 3-continued miRNA sponges

| miRNA | Binding sites | Cell context |
| --- | --- | --- |
| 21, 140-3p, 140-5p, empty | one to two perfect sites | mammalian cell lines |
| 133, empty | three perfect sites | mouse cardiac myocytes |
| 204, 211, empty | two perfect sites | ST2 cell line, osteogenic and adipogenic differentiation |
| 96/182/183, empty | four bulged sites each | mouse retina |
| let-7, 16, empty | six to nine bulged sites | lung cancer cell line |
| D.m. 7, 8, 9a, 276a | 10 bulged sites | Transgenic fruitflies |
| 9, 10b, CXCR4 | eight bulged sites | 4T1 breast cancer cell line, xenograft |
| herpesvirus miR-K12-7, K12-8, BART1-5p, BART4, empty | six bulged sites | human B cell lines |
| 144, 451, empty | four perfect sites | mouse hematopoietic stem/progenitor cells, transplant |
| let-7, 29, 125, let-7/125, 128, empty | 16 bulged sites | neural stem cells |
| 21, empty | two perfect sites | mouse cardiocytes |
| 18a, 19b, 20a, nonspecific | one perfect site | K562 cell line |
| 145/146, empty | eight to nine bulged sites each | mouse hematopoietic stem/progenitor cells, transplant |
| 31, CXCR4 | seven bulged sites | MCF7-Ras breast cancer cell line, xenograft |

In some embodiments, the non-coding sequence may be an RNA binding protein site. RNA binding proteins and binding sites therefore are listed in numerous databases known to those of skill in the art, including RBPDB (rbpdb.ccbr.utoronto.ca). In some embodiments, the RNA binding protein comprises one or more RNA-binding domains, selected from RNA-binding domain (RBD, also known as RNP domain and RNA recognition motif, RRM), K-homology (KH) domain (type I and type II), RGG (Arg-Gly-Gly) box, Sm domain; DEAD/DEAH box (SEQ ID NOs: 34036 and 34037), zinc finger (ZnF, mostly C-x8-X-x5-X-x3-H (SEQ ID NO: 34038)), double stranded RNA-binding domain (dsRBD), cold-shock domain; Pumilio/FBF (PUF or Pum-HD) domain, and the Piwi/Argonaute/Zwille (PAZ) domain.

In some embodiments, the DNA sequence comprises an aptamer. Aptamers are short, single-stranded DNA molecules that can selectively bind to a specific target. The target may be, for example, a protein, peptide, carbohydrate, small molecule, toxin, or a live cell. Some aptamers can bind DNA, RNA, self-aptamers or other non-self aptamers. Aptamers assume a variety of shapes due to their tendency to form helices and single-stranded loops. Illustrative DNA and RNA aptamers are listed in the Aptamer database (scicrunch.org/resources/Any/record/nlx_144509-1/SCR_001781/resolver?q=*&l=).

In some embodiments, the DNA sequence encodes a circular RNA molecule that comprises between about 200 nucleotides and about 10,000 nucleotides.

In some embodiments, the DNA sequence encodes a circular RNA molecule that comprises a spacer between the IRES and a start codon of the protein-coding nucleic acid sequence. The spacer may be of any length. For example, in some embodiments, the length of the spacer is selected to optimize translation of the protein-coding nucleic acid sequence.

In some embodiments, the DNA sequence encodes a circular RNA molecule comprising an IRES that is configured to promote rolling circle translation. In some embodiments, the DNA sequence encodes a circular RNA comprising a protein-coding nucleic acid sequence that lacks a stop codon. In some embodiments, the DNA sequence encodes a circular RNA molecule comprising (i) an IRES that is configured to promote rolling circle translation, and (ii) a protein-coding nucleic acid sequence that lacks a stop codon.

The DNA sequences described herein may be comprised in one or more vectors. For example, in some embodiments, a viral vector comprises a DNA sequence encoding a circular RNA. The viral vector may be, for example, an adeno-associated virus (AAV) vector, an adenovirus vector, a retrovirus vector, a lentivirus vector, a vaccinia or a herpesvirus vector.

In some embodiments, the viral vector is an AAV. As used herein, the term "adeno-associated virus" (AAV), includes but is not limited to, AAV1, AAV2, AAV3 (including types 3 A and 3B), AAV4, AAV5, AAV6, AAV7, AAV8, AAV9, AAV10, AAV11, AAV12, avian AAV, bovine AAAV, canine AAV, equine AAV, ovine AAV, and any other AAV now known or later discovered. In some embodiments, the AAV vector may be a modified form (i.e., a form comprising one or more amino acid modifications relative thereto) of one or more of AAV1, AAV2, AAV3 (including types 3 A and 3B), AAV4, AAV5, AAV6, AAV7, AAV8, AAV9, AAV10, AAV11, AAV12, avian AAV, bovine AAV, canine AAV, equine AAV, or ovine AAV. Various AAV serotypes and variants thereof are described, e.g., BERNARD N. FIELDS et al, VIROLOGY, volume 2, chapter 69 (4th ed., Lippincott-Raven Publishers). A number of relatively new AAV serotypes and clades have been identified (see, e.g., Gao et al. (2004) J Virology 78:6381-6388; Moris et al. (2004) Virology 33-:375-383). The genomic sequences of various serotypes of AAV, as well as the sequences of the native terminal repeats (TRs), Rep proteins, and capsid subunits are known in the art. Such sequences may be found in the literature or in public databases such as the GenBank® Database. See, e.g., GenBank Accession Numbers NC_044927, NC_002077, NC_001401, NC_001729, NC 001863, NC 001829, NC_001862, NC_000883, NC_001701, NC_001510, NC_006152, NC_006261, AF063497, U89790, AF043303, AF028705, AF028704, J02275, JO 1901, J02275, X01457, AF288061, AH009962, AY028226, AY028223, NC 001358, NC 001540, AF513851, AF513852, AY530579; the disclosures of which are incorporated by reference herein for teaching parvovirus and AAV nucleic acid and amino acid sequences. See also, e.g., Srivistava et al. (1983) J Virology 45:555; Chiorini et al. (1998) J. Virology 71:6823; Chiorini et al (1999) J Virology 73:1309; Bantel-Schaal et al. (1999) J. Virology 73:939; Xiao et al. (1999) J. Virology 73:3994; Muramatsu et al. (1996) Virology 221:208; Shade et al. (1986) J Virol. 58:921; Gao et al. (2002) Proc. Nat. Acad. Sci. USA 99: 1 1854; Moris et al. (2004) Virology 33-:375-383; international patent publications WO 00/28061, WO 99/61601, WO 98/11244; and U.S. Pat. No. 6,156,303; the disclosures of which are incorporated by reference herein.

In some embodiments, a DNA sequence described herein is comprised in an AAV2 vector, or a variant thereof. In some embodiments, a DNA sequence described herein is comprised an AAV4 vector, or a variant thereof. In some embodiments, a DNA sequence described herein is comprised in an AAV8 vector, or a variant thereof. In some embodiments, a DNA sequence described herein is comprised in an AAV9 vector, or a variant thereof.

In some embodiments, a DNA sequence described herein is comprised in a viral-like particle (VLP). Viral like particles are molecules that closely resemble viruses, but are non-infectious because they contain little or no viral genetic material. They can be naturally occurring or synthesized through the individual expression of viral structural proteins, which can then self-assemble into a virus-lie structure. Combinations of structural capsid proteins from different viruses can be used to create VLPs. For example VLPs may be derived from the, AAVs, retrovirus, Flaviviridae, paramyoxoviridae, or bacteriophages. VLPs can be produced in multiple cell culture systems, including bacteria, mammalian cell lines, insect cell lines, yeast and plant cells.

In some embodiments, a DNA sequence described herein is comprised in a non-viral vector. The non-viral vector may be, for example, a plasmid comprises the DNA sequence. In some embodiments, the non-viral vector is a closed-ended DNA. A closed-ended DNA is a non-viral, capsid-free DNA vector with covalently closed ends (see, e.g., WO2019/169233). In some embodiments, a mini-intronic plasmid vector comprises a DNA sequence described herein. Mini-intronic plasmids are expression systems that contain a bacterial replication origin and selectable marker maintaining the juxtaposition of the 5' and the 3' ends of transgene expression cassette as in a minicircle (see, e.g., Lu, J., et al., Mol Ther (2013) 21(5) 954-963).

In some embodiments, a DNA sequence described herein is comprised in a lipid nanoparticle. Lipid nanoparticles (or LNPs) are submicron-sized lipid emulsions, and may offer one or more of the following advantages: (i) control and/or targeted drug release, (ii) high stability, (iii) biodegradability of the lipids used, (iv) avoid organic solvents, (v) easy to scale-up and sterilize, (vi) less expensive than polymeric/surfactant based carriers, (vii) easier to validate and gain regulatory approval. In some embodiments, the lipid nanoparticles range in diameter between about 10 and about 1000 nm.

In some embodiments, a DNA sequence encodes a circular RNA molecule, wherein the circular RNA molecule comprises a protein-coding nucleic acid sequence and an internal ribosome entry site (IRES) operably linked to the protein-coding nucleic acid sequence in a non-native configuration wherein the IRES comprises: at least one RNA secondary structure; and a sequence that is complementary to an 18S ribosomal RNA (rRNA).

In some embodiments, a DNA sequence encodes a circular RNA molecule, wherein the circular RNA molecule comprises a protein-coding nucleic acid sequence and an internal ribosome entry site (IRES) operably linked to the protein-coding nucleic acid sequence in a non-native configuration wherein the IRES comprises: at least one RNA secondary structure element; and a sequence that is complementary to an 18S ribosomal RNA (rRNA); wherein the IRES has a minimum free energy (MFE) of less than −18.9 kJ/mol and a melting temperature of at least 35.0° C.; and wherein the RNA secondary structure element is formed from the nucleotides at about position 40 to about position 60 of the IRES, wherein the first nucleic acid at the 5' end of the IRES is considered to be position 1.

In some embodiments, a DNA sequence comprises a nucleic acid sequence encoding a circular RNA molecule; wherein the circular RNA molecule comprises a protein-coding nucleic acid sequence and an internal ribosome entry site (IRES) operably linked to the protein-coding nucleic acid sequence in a non-native configuration; wherein the IRES is encoded by any one of the nucleic acid sequences listed of SEQ ID NO: 1-228 or SEQ ID NO: 229-17201, or a nucleic acid sequence that is at least 90% or at least 95% identical thereto.

Also provided herein are cells comprising a recombinant circRNA molecule, a DNA molecule, or a vector described herein. Any prokaryotic or eukaryotic cell that can be contacted with and stably maintain the recombinant circRNA molecule, DNA molecule encoding the recombinant circRNA molecule, or vector comprising the recombinant circRNA molecule may be used in the context of the present disclosure. Examples of prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. In some embodiments, the host cell is a eukaryotic cell. Suitable eukaryotic cells are known in the art and include, for example, yeast cells, insect cells, and mammalian cells. Examples of yeast cells include those from the genera *Hansenula, Kluyveromyces, Pichia, Rhinosporidium, Saccharomyces*, and *Schizosaccharomyces*. Suitable insect cells include Sf-9 and HIS cells (Invitrogen, Carlsbad, Calif.) and are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993).

In some embodiments, the cell is a mammalian cell. A number of mammalian cells are known in the art, many of which are available from the American Type Culture Collection (ATCC, Manassas, Va.). Examples of mammalian cells include, but are not limited to, HeLa cells, HepG2 cells, Chinese hamster ovary cells (CHO) (e.g., ATCC No. CCL61), CHO DHFR-cells (Urlaub et al., *Proc. Natl. Acad. Sci. USA*, 97: 4216-4220 (1980)), human embryonic kidney (HEK) 293 or 293T cells (e.g., ATCC No. CRL1573), and 3T3 cells (e.g., ATCC No. CCL92). Other mammalian cell lines are the monkey COS-1 (e.g., ATCC No. CRL1650) and COS-7 cell lines (e.g., ATCC No. CRL1651), as well as the CV-1 cell line (e.g., ATCC No. CCL70). Further exemplary mammalian host cells include primate cell lines and rodent cell lines, including transformed cell lines. Normal diploid cells, cell strains derived from in vitro culture of primary tissue, as well as primary explants also are suitable. Other mammalian cell lines include, but are not limited to, mouse neuroblastoma N2A cells, HeLa, mouse L-929 cells, and BHK or HaK hamster cell lines, all of which are available from the American Type Culture Collection (ATCC; Manassas, Va.). Methods for selecting mammalian cells and methods for transformation, culture, amplification, screening, and purification of such cells are well known in the art (see, e.g., Ausubel et al., supra). In some embodiments, the mammalian cell is a human cell.

Method of Producing a Protein

The disclosure further provides a method of producing a protein in a cell, which comprises contacting a cell with the above-described recombinant circular RNA molecule, the above-described DNA molecule comprising a nucleic acid sequence encoding the recombinant circRNA molecule, or a vector comprising the recombinant circRNA molecule under conditions whereby the protein-coding nucleic acid sequence is translated and the protein is produced in the cell.

In some embodiments, a method of producing a protein in a cell comprises contacting a cell with a DNA sequence described herein, or a vector comprising the DNA sequence, under conditions whereby the protein-coding nucleic acid sequence is translated and the protein is produced in the cell. Also provided is a protein produced by the disclosed methods.

In some embodiments, production of the protein is tissue-specific. For example, the protein may be selectively produced in one or more of the following tissues: muscle, liver, kidney, brain, lung, skin, pancreas, blood, or heart.

In some embodiments, the protein is expressed recursively in the cell.

In some embodiments, the half-life of the circular RNA in the cell is about 1 to about 7 days. For example, the half-life of the circular RNA may be about 1, about 2, about 3, about 4, about 5, about 6, about 7, or more days.

In some embodiments, the protein is produced in the cell for at least about 10%, at least about 20%, or at least about 30% longer than if the protein-coding nucleic acid sequence is provided to the cell using a viral vector encoding a linear RNA or as a linear RNA.

In some embodiments, the protein is produced in the cell at a level that is at least about 10%, at least about 20%, or at least about 30% higher than if the protein-coding nucleic acid sequence is provided to the cell using a viral vector or as a linear RNA.

Use of the IRES sequences described herein to express a protein from a circular RNA may, in some embodiments, allow for continued expression of a protein from the circular RNA in a cell even under stress conditions. In response to one or more stress conditions, production of proteins from linear RNA is often suppressed. Accordingly, in some embodiments, circRNA can be used as an alternative for production of proteins from linear RNAs during stress conditions. In some embodiments, a protein expressed from a circular RNA in a cell is expressed under one or more stress conditions. In some embodiments, expression of a protein from a circular RNA in a cell is not substantially disrupted when the cell is exposed to one or more stress conditions. For example, exposure of the cell to one or more stress conditions may change expression of a protein from a circular RNA by less than 15%, less than 10%, less than 5%, less than 3%, less than 1%, or less than 0.5%. In some embodiments, a protein expressed from a circular RNA is expressed at a level under one or more stress conditions that is substantially the same as the level expressed in the same cell in the absence of the one or more stress conditions. In some embodiments, the level of expression of a protein from a circular RNA in a cell is at least about 70%, at least about 75%, at least about 80%, at least about 85%, at least about 90%, at least about 95%, or at least about 99%, relative to the level of expression in the absence of the one or more stress conditions. A non-limiting list of conditions which may cause cellular stress include changes in temperature (including exposure to extreme temperatures and/or heat shock), exposure to toxins (including viral or bacterial toxins, heavy metals, etc.), exposure to electromagnetic radiation, mechanical damage, viral infection, etc.

In some embodiments, the circRNAs described herein (including components thereof, such as the IRES sequences) facilitate cap-independent translation activity from the circRNA. Canonical translation via a cap-independent mechanism may be reduced in some human diseases. Accordingly, the use of circRNAs to express proteins may be particularly helpful for treating such diseases. In some embodiments, use of the circRNAs described herein facilitates cap-independent translation activity from the circRNA under conditions wherein cap-dependent translation is reduced or turned-off in a cell.

As discussed above, translation of the protein-coding nucleic acid sequence may occur in an infinite loop (i.e., recursively) when the IRES is in-frame with the protein-coding nucleic acid sequence and the protein-coding sequence lacks a stop codon. Thus, in some embodiments, the method of producing a protein in a cell produces a concatenated protein.

Any prokaryotic or eukaryotic host cell described herein may be contacted with the recombinant circRNA molecule or a vector comprising the circRNA molecule. The host cell may be a mammalian cell, such as a human cell. In some embodiments, the cell is in vivo. In some embodiments, the cell is in vitro. In some embodiments, the cell is ex vivo. In some embodiments, the cell is in a mammal, such as a human.

In some embodiments, regardless of cell type chosen, 5' cap-dependent translation is impaired in the cell (e.g., decreased, reduced, inhibited, or completely obliterated). In some embodiments, there is no substantial 5' cap-dependent translation in the cell.

The recombinant circular RNA molecule, a DNA molecule encoding same, or vectors comprising same, may be introduced into a cell by any method, including, for example, by transfection, transformation, or transduction. The terms "transfection," "transformation," and "transduction" are used interchangeably herein and refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature,* 346: 776-777 (1990)); strontium phosphate DNA co-precipitation (Brash et al., Mol. Cell. Biol., 7: 2031-2034 (1987); and magnetic nanoparticle-based gene delivery (Dobson, J., *Gene Ther,* 13 (4): 283-7 (2006)).

Naked RNA, DNA molecules encoding circular RNA molecules, or vectors comprising the circular RNAs or DNAs encoding circular RNAs may be administered to cells in the form of a composition. In some embodiments, the composition comprises a pharmaceutically acceptable carrier. The choice of carrier will be determined in part by the particular circular RNA molecule, DNA sequence, or vector and type of cell (or cells) into which the circular RNA molecule, DNA sequence, or vector is introduced. Accordingly, a variety of formulations of the composition are possible. For example, the composition may contain preservatives, such as, for example, methylparaben, propylparaben, sodium benzoate, and benzalkonium chloride. A mixture of two or more preservatives optionally may be used. In addition, buffering agents may be used in the composition. Suitable buffering agents include, for example, citric acid, sodium citrate, phosphoric acid, potassium phosphate, and various other acids and salts. A mixture of two or more buffering agents optionally may be used. Methods for preparing compositions for pharmaceutical use are known to those skilled in the art and are described in more detail in, for example, Remington: The Science and Practice of Pharmacy, Lippincott Williams & Wilkins; 21st ed. (May 1, 2005).

In some embodiments, the composition containing the recombinant circular RNA molecule, DNA sequence, or vector, can be formulated as an inclusion complex, such as cyclodextrin inclusion complex, or as a liposome. Liposomes can be used to target host cells or to increase the half-life of the circular RNA molecule. Methods for preparing liposome delivery systems are described in, for example, Szoka et al., Ann. Rev. Biophys. Bioeng., 9: 467 (1980), and U.S. Pat. Nos. 4,235,871; 4,501,728; 4,837,028; and 5,019,369. The recombinant circRNA molecule may also be formulated as a nanoparticle.

A host cell can be contacted in vivo or in vitro with a recombinant circRNA molecule, a DNA sequence, or a vector, or compositions containing any of the foregoing. The term "in vivo" refers to a method that is conducted within living organisms in their normal, intact state, while an "in vitro" method is conducted using components of an organism that have been isolated from its usual biological context. When the method is conducted in vivo, in some embodiments the production of the protein is tissue-specific. By "tissue-specific" is meant that the protein is produced in only a subset of tissue types within an organism, or is produced at higher levels in a subset of tissue types relative to the baseline expression across all tissue types. The protein may be produced in any tissue type, such as, for example, tissues of muscle, liver, kidney, brain, lung, skin, pancreas, blood, or heart.

Inhibiting circRNA Translation

The disclosure also provides an oligonucleotide molecule comprising a nucleic acid sequence that hybridizes to an internal ribosome entry site (IRES) present on a circular RNA molecule and inhibits translation of the circular RNA molecule. In some embodiments, the circular RNA molecule is a naturally occurring circular RNA molecule. In some embodiments, the circular RNA molecule is a recombinant circular RNA molecule, such as the recombinant circRNA molecule described herein. In some embodiments, the recombinant circRNA molecule may comprise a protein-coding nucleic acid sequence and an IRES operably linked to the protein-coding nucleic acid sequence (optionally, in a non-native configuration), wherein the IRES comprises at least one RNA secondary structure; and a sequence that is complementary to an 18S ribosomal RNA (rRNA); and wherein the IRES has a minimum free energy (MFE) of less than −18.9 kJ/mol and a melting temperature of at least 35.0° C., as described herein. In some embodiments, the recombinant circRNA molecule may comprise a protein-coding nucleic acid sequence and an IRES operably linked to the protein-coding nucleic acid sequence (optionally, in a non-native configuration); wherein the IRES is encoded by any one of the nucleic acid sequences listed in SEQ ID NO: 1-228 or SEQ ID NO: 229-17201, or a nucleic acid sequence that is at least 90% or at least 95% identical thereto.

The oligonucleotide that hybridizes to the IRES on a recombinant circRNA molecule may be of any type and size. In some embodiments, the oligonucleotide may be about 8 to about 80 nucleotides in length, such as about 15 to about 30 nucleotides in length. In some embodiments, the oligonucleotide may be about 20, about 22, or about 24 nucleotides in length. In some embodiments, the oligonucleotide may be an antisense oligonucleotide (also referred to as "ASO"). The term "antisense oligonucleotide," as used herein, refers to a short, synthetic, single-stranded oligodeoxynucleotide or oligodeoxyribonucleotide which is complementary to a target RNA sequence and can reduce, restore, or modify protein expression through several distinct mechanisms (Rinaldi, C., Wood, M., Nat Rev Neurol, 14: 9-21 (2018); Crooke, S. T., Nucleic Acid Ther., 27: 70-77 (2017); and Chan et al., Clin. Exp. Pharmacol. Physiol. 33: 533-540 (2006)). In some embodiments, the antisense oligonucleotide may be a locked nucleic acid oligonucleotide (LNA). The term "locked nucleic acid (LNA)" refers to oligonucleotides that contain one or more nucleotide building blocks in which an extra methylene bridge fixes the ribose moiety either in the C3'-endo (beta-D-LNA) or C2'-endo (alpha-L-LNA) conformation (Grunweller A, Hartmann R K, BioDrugs, 21(4): 235-243 (2007)). In some embodiments, the oligonucleotide is a small interfering RNA (siRNA), small hairpin RNA (shRNA), CRISPR (sgRNA), or micro RNA (miRNA).

The oligonucleotide may comprise one or more modifications that enhance hybridization of the oligonucleotide to the IRES of the circRNA molecule and/or inhibition of translation of the circRNA molecule. The modification may be at the 5' or at the 3' end of the oligonucleotide. Suitable modifications include, but are not limited to, a modified internucleoside linkage, a modified sugar, or a modified nucleobase. In some embodiments, the oligonucleotide may be conjugated to a fluorophore (e.g., Cy3, FAM, Alexa 488, etc.) or to another molecule (e.g., biotin, alkaline phosphatase, antibody, nucleic acid aptamer, peptide, etc.). In some embodiments, the oligonucleotide may be labeled with a peptide or protein, for example using CLICK chemistry. It will be appreciated that the naturally occurring internucleoside linkage of RNA and DNA is a 3' to 5' phosphodiester linkage. Oligonucleotides having one or more modified, i.e. non-naturally occurring, internucleoside linkages are known to exhibit desirable properties such as, for example, enhanced cellular uptake, enhanced affinity for target nucleic acids, and increased stability in the presence of nucleases. Modified internucleoside linkages include, for example, internucleoside linkages that retain a phosphorus atom as well as internucleoside linkages that do not have a phosphorus atom. Representative phosphorus-containing internucleoside linkages include, but are not limited to, phosphodiesters, phosphotriesters, methylphosphonates, phosphoramidate, and phosphorothioates. Methods of preparing phosphorous-containing and non-phosphorous-containing linkages are well known.

In some embodiments, the oligonucleotide molecule may comprise a modified backbone. Oligonucleotides having modified backbones include those that retain a phosphorus atom in the backbone and those that do not have a phosphorus atom in the backbone. Modified oligonucleotides that do not have a phosphorus atom in their internucleoside backbone may be referred to as "oligonucleosides." Examples of modified oligonucleotide backbones include, but are not limited to, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5', or 2' to 2' linkage.

The oligonucleotide molecule may further comprise one or more nucleotides having modified sugar moieties. Sugar modifications may impart nuclease stability, binding affinity or some other beneficial biological property to the oligonucleotide. The furanosyl sugar ring of a nucleoside can be modified in a number of ways including, but not limited to, addition of a substituent group, particularly at the 2' position; bridging of two non-geminal ring atoms to form a bicyclic nucleic acid (BNA); and substitution of an atom or group such as —S—, —N(R)— or —C($R^1$)($R^2$) for the ring oxygen at the 4'-position. Modified sugars include, but are not limited to: substituted sugars, especially 2'-substituted sugars having a 2'-F, 2'-$OCH_2$ (2'-OMe) or a 2'-O($CH_2$)2-$OCH_3$ (2'-O-methoxyethyl or 2'-MOE) substituent group; and bicyclic modified sugars (BNAs), having a 4'-($CH_2$)n-O-2' bridge, where n=1 or n=2. Methods for the preparation of modified sugars are well known to those skilled in the art.

In some embodiments, the oligonucleotide may be chemically modified at its 5' and/or its 3' end. In other words, one or more moieties may be chemically (e.g., covalently) linked to the 5' and/or 3' end of the oligonucleotide molecule. Such modifications include, for example, chemical linkage of protein or sugar moieties to the 5' and/or 3' end of the oligonucleotide molecule. Other modifications that enhance oligonucleotide affinity for target nucleic acids and/or increase oligonucleotide stability are known in the art (see, e.g., U.S. Patent Application Publication US 2019/0323013) and may be employed in the context of the present disclosure.

The disclosure also provides a method of inhibiting translation of a protein-coding nucleic acid sequence present on a circular RNA molecule, which method comprises contacting the circular RNA molecule with the above-described oligonucleotide molecule, whereby the oligonucleotide molecule hybridizes to the RNA secondary structure and/or the nucleic acid sequence complementary to 18S rRNA present on the IRES of the circular RNA molecule and inhibits translation of the circular RNA molecule.

In some embodiments, the oligonucleotide can hybridize to either the RNA secondary structure element or the nucleic acid sequence that is complementary to 18S rRNA present on the IRES. In other embodiments, the oligonucleotide can hybridize to both the RNA secondary structure element and the nucleic acid sequence that is complementary to 18S rRNA. For example, a first oligonucleotide may hybridize to the RNA secondary structure element and a second oligonucleotide may hybridize to the nucleic acid sequence that is complementary to 18S rRNA. Alternatively, a single oligonucleotide may hybridize to both the RNA secondary structure element and the nucleic acid sequence that is complementary to 18S rRNA present on the IRES. Appropriate hybridization stringency conditions are described herein.

Also provided is a composition comprising (i) a DNA sequence disclosed herein and a (ii) non-coding circular RNA, or a DNA sequence encoding the same. The DNA sequence may encode a circRNA. In some embodiments, the non-coding circular RNA may comprise one or more of a binding site for an RNA binding protein, an aptamer, or a miRNA sponge. In some embodiments, the non-coding circular RNA may have one or more functions, such as sponging miRNAs, regulating mRNA splicing machinery, sequestering RNA-binding proteins (RBPs), regulating RBP interaction, or activating immune responses.

Also provided is a method of delivering a non-coding circular RNA to a cell, the method comprising contacting the cell with a composition comprising (i) a DNA sequence disclosed herein and a (ii) non-coding circular RNA, or a DNA sequence encoding the same, thereby delivering the non-coding circular RNA to the cell.

The following examples further illustrate the invention but, of course, should not be construed as in any way limiting its scope.

EXAMPLES

The following examples describe the development of a high-throughput screen to systematically identify and quantify RNA sequences that can direct circRNA translation. Over 17,000 circRNA internal ribosome entry sites (IRES) were identified and validated, and it was shown that 18S rRNA complementarity and a structured RNA element on the IRES are important for facilitating circRNA cap-independent translation. With genomic and peptidomic analyses of the IRES, nearly 1,000 putative endogenous protein-coding circRNAs were identified, along with hundreds of translational units encoded by these circRNAs. circFGFR1p, a protein encoded by circFGFR1, was also characterized. This protein functions as a negative regulator of FGFR1 to suppress cell growth under stress conditions.

Example 1

This example describes the systematic identification of RNA sequences that facilitate cap-independent circRNA translation. Canonical translation via a cap-independent mechanism may be reduced in numerous human diseases. Accordingly, the use of circRNAs to express proteins may be particularly helpful for treating such diseases.

To systematically identify the RNA sequence that can facilitate cap-independent translation on circRNAs, an oligo-split-eGFP-circRNA reporter construct was developed that allows for screening and quantifying the cap-independent translation activity of synthetic oligonucleotide inserts ("oligos" hereafter) on circRNA in a high-throughput manner (FIG. 1A). Specifically, the construct contains a bicistronic mRuby reporter followed by a permuted split-eGFP reporter flanked by human ZKSCAN1 introns, where during transcription, the pre-mRNA of the construct will undergo spliceosome-mediated back-splicing and reconstitute full-length eGFP on the circRNA. Because full-length eGFP is only reconstituted upon back-splicing, the eGFP fluorescence signal can only come from the circRNA through cap-independent translation. A synthetic oligonucleotide library was then cloned into the construct to drive the expression of eGFP reporter (FIG. 1A). The library contained 55,000 oligos of sequences from the reported IRESs in the IRESite database (including human and non-human IRES; see Mokrejš et al., Nucleic acids research 38, D131-D136 (2009)), the native 5' untranslated region (5' UTR) of viral and human genes, and the native and synthetic sequences from viral and human transcripts (FIG. 1A). Library design is detailed in Weingarten-Gabbay et al., Science 351, aad4939 (2016). For the viral and human transcripts, genes were selected that have been reported to remain associated with polysomes when the cap-dependent translation was suppressed and the genes with alternative isoforms that differ in their translation start site (FIG. 1A).

Figure 8C:
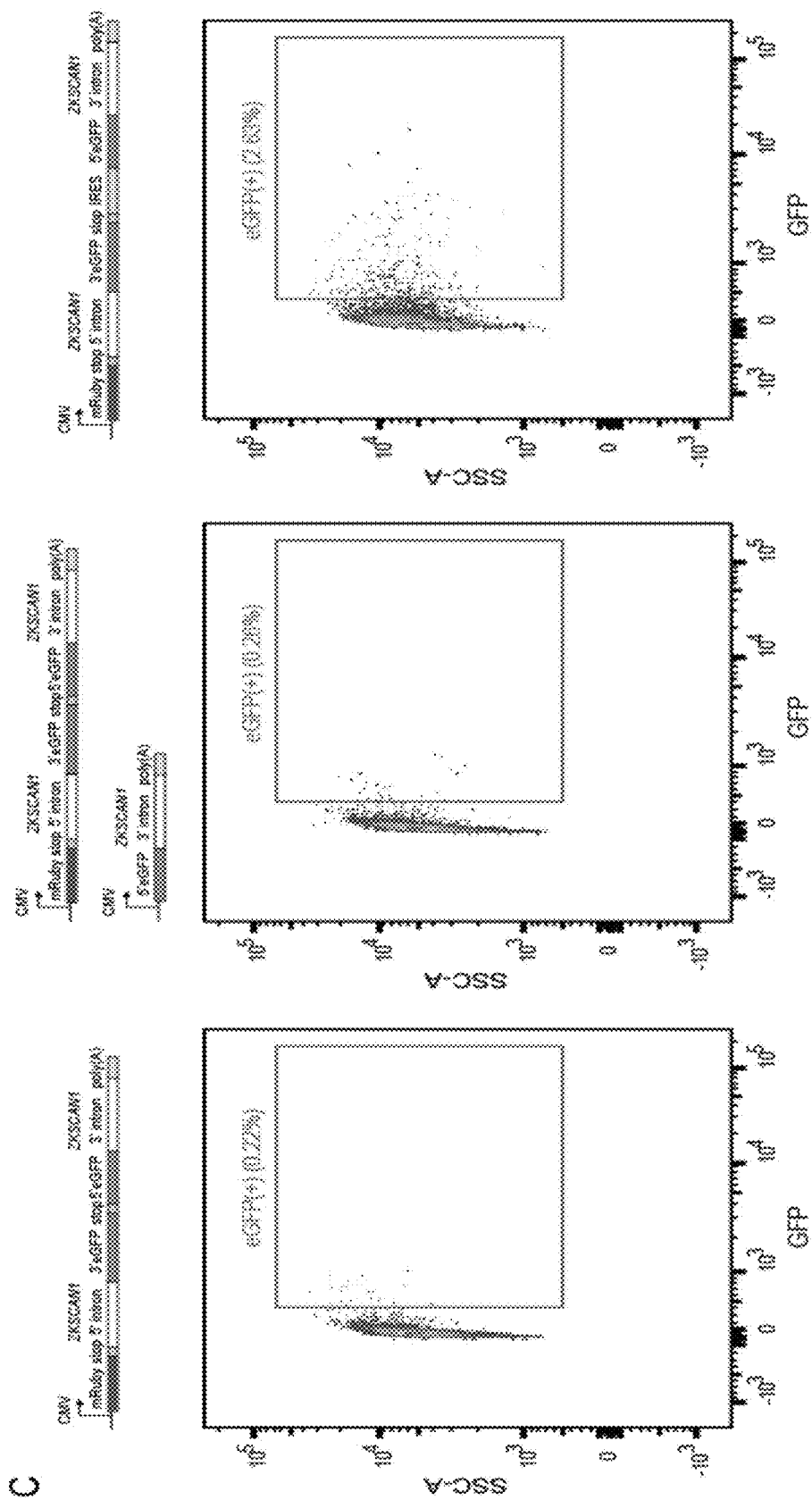

Two well-known concerns for bicistronic IRES screens are cryptic promoters or splice sites that activate transcription or readthrough of the downstream open reading frame (ORF), respectively. The design used herein obviates both concerns because ectopic transcription of only the 5' fragment of the split-eGFP cannot produce fluorescence signal. Northern blots, quantitative reverse transcription polymerase chain reaction (qRT-PCR), RNase R treatment, and reporter gene experiments confirmed that the eGFP signal detected did not come from trans-splicing or the nicking of the eGFP circRNA (FIG. 8A-8C). The reporter produces a ~3000 nucleotide (nt) primary linear transcript and a ~900 nt eGFP circRNA; RNase R exonuclease treatment can efficiently remove the linear transcript but not the circRNA (FIG. 8A). The mRuby gene allowed for normalization for transduction efficiency by translation of a regular linear mRNA. Following transfection into human embryonic kidney (HEK) 293T cells, the transfected cells were sorted by the ratio of eGFP to mRuby fluorescence into seven bins, and deconvoluted the frequencies of oligo sequences in each pool by deep sequencing (FIG. 1A). With this system, it is possible quantify the cap-independent translation activity on circRNA for each oligo in the library in a high-throughput manner.

Figure 1B:
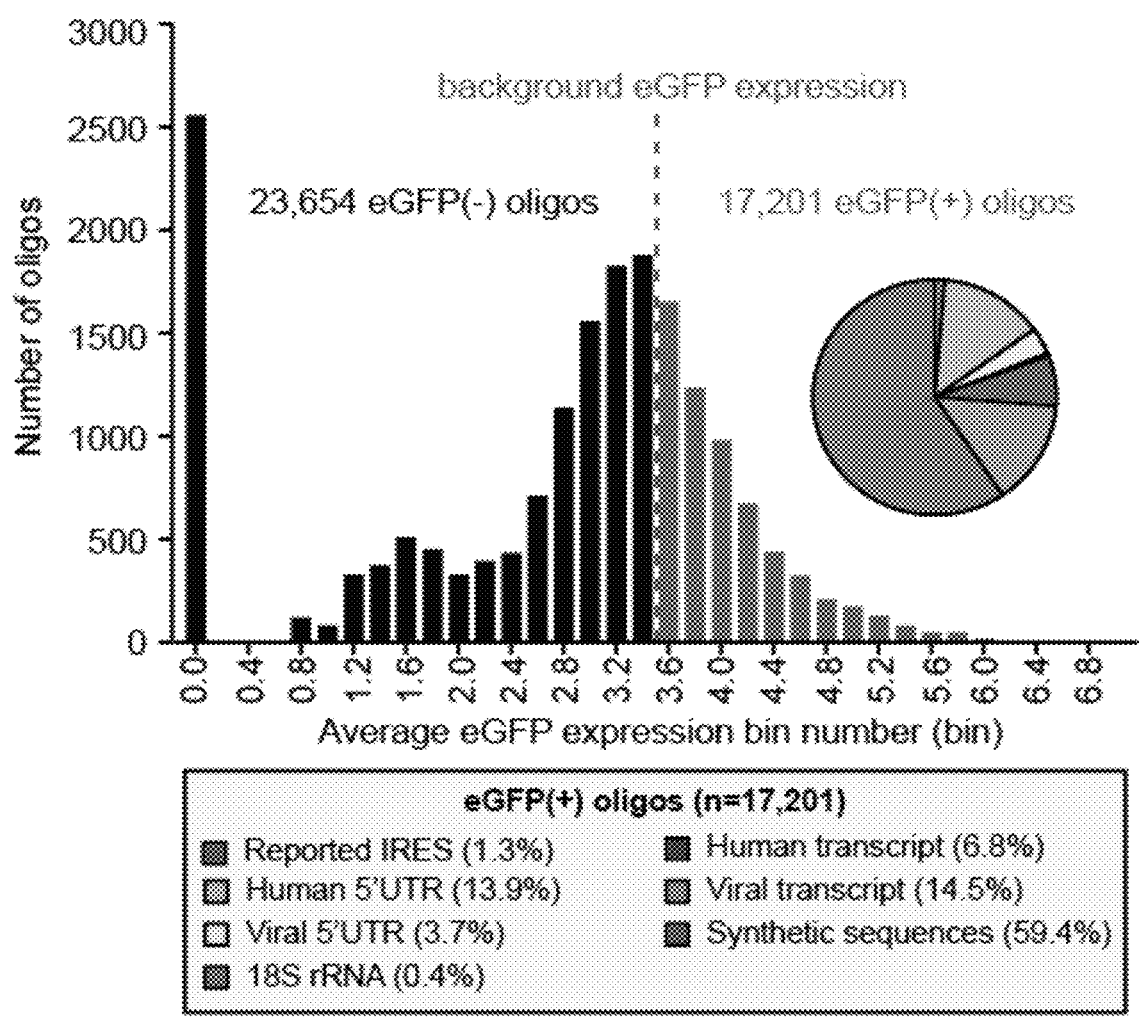
Figure 1C:
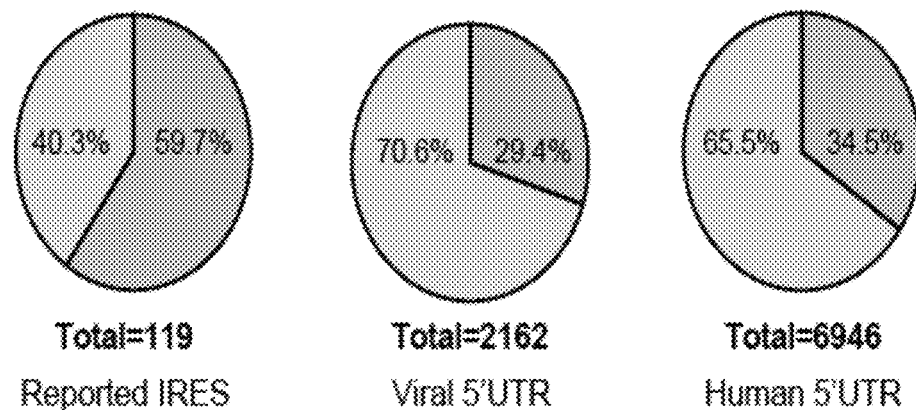
Figure 9A:
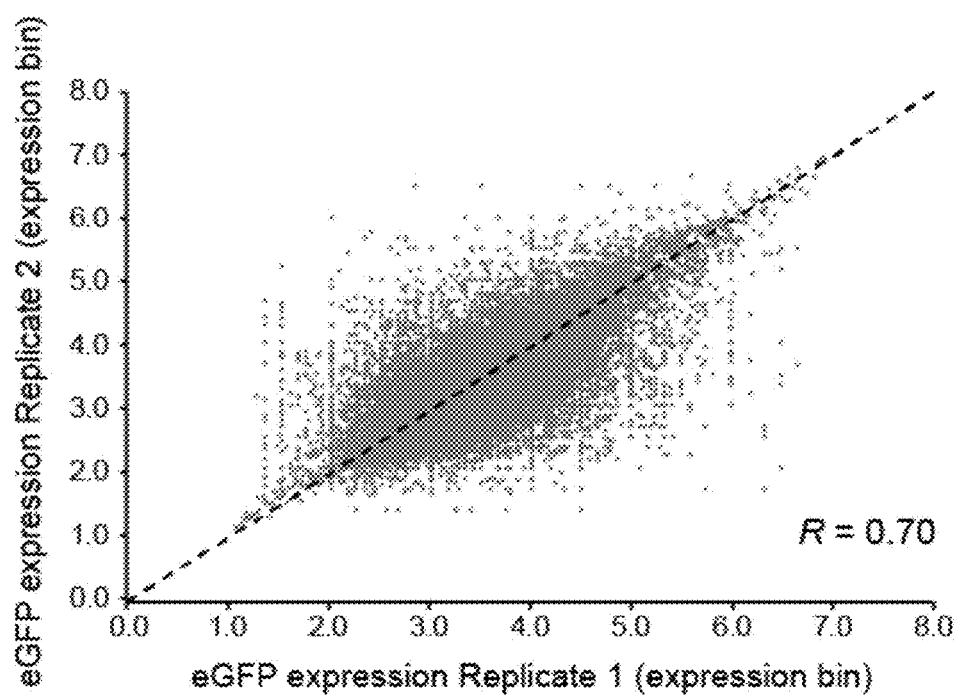
FIG. 9A-9F show high-throughput identification of IRES sequences that can facilitate cap-independent translation activity on circRNAs.
Figure 9B:
Figure 9C:
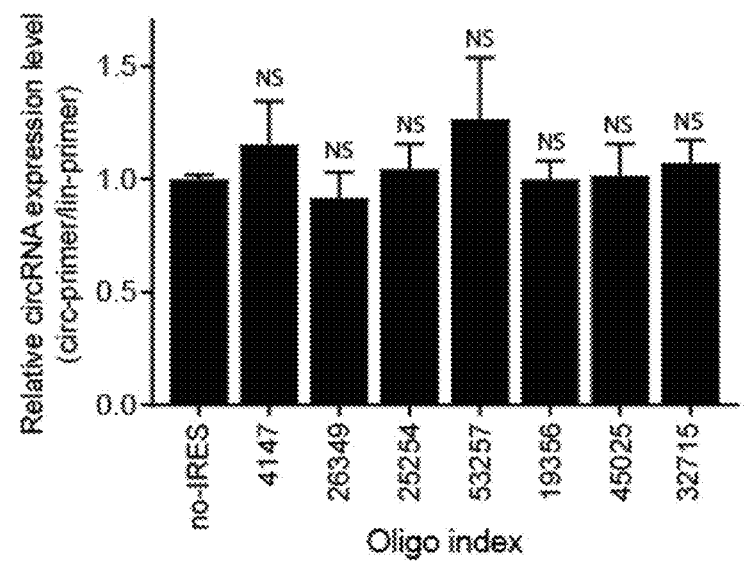
Figure 9D:
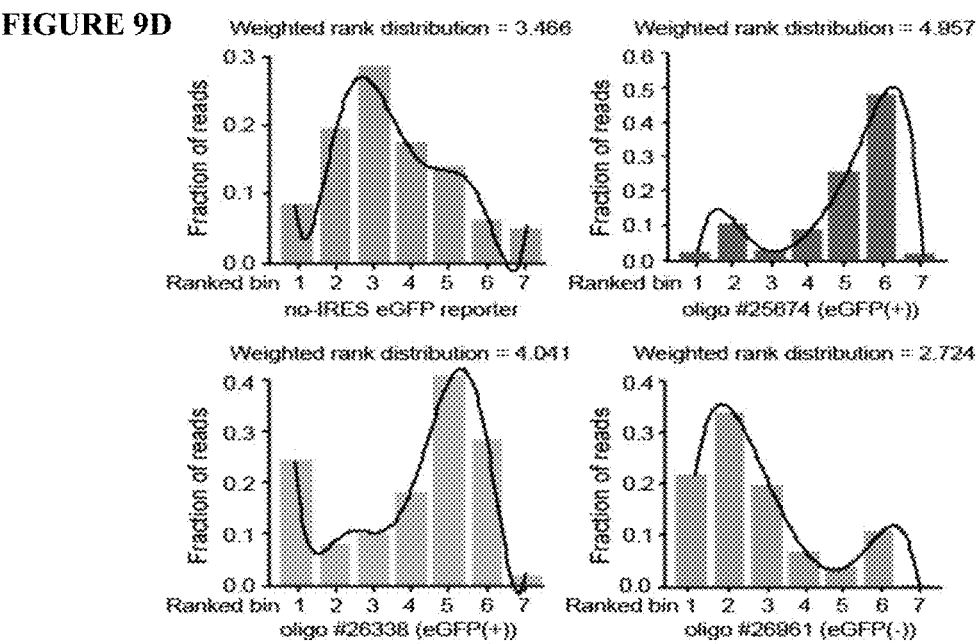
Figure 9E:
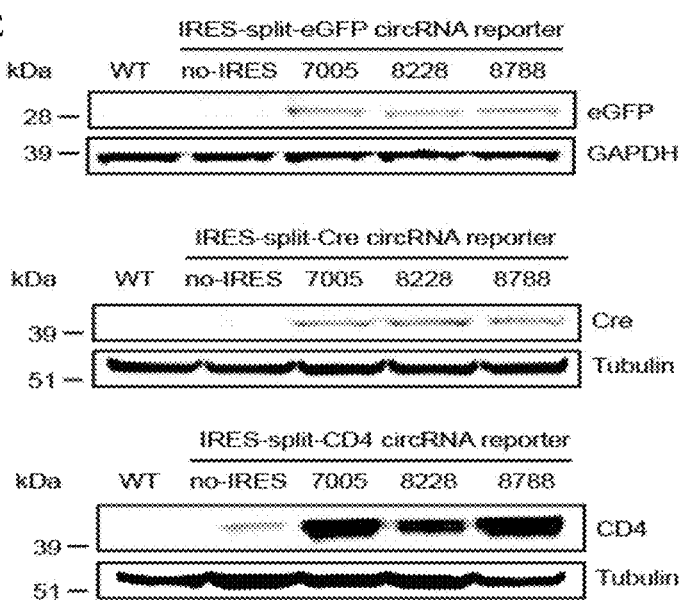
Figure 9F:
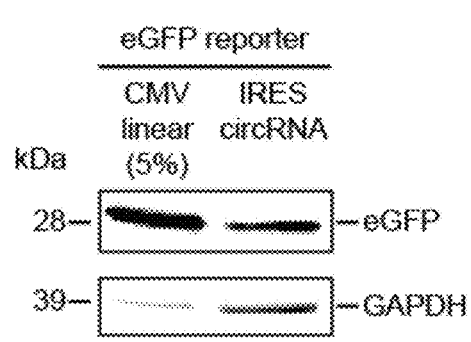
Figure 10A:
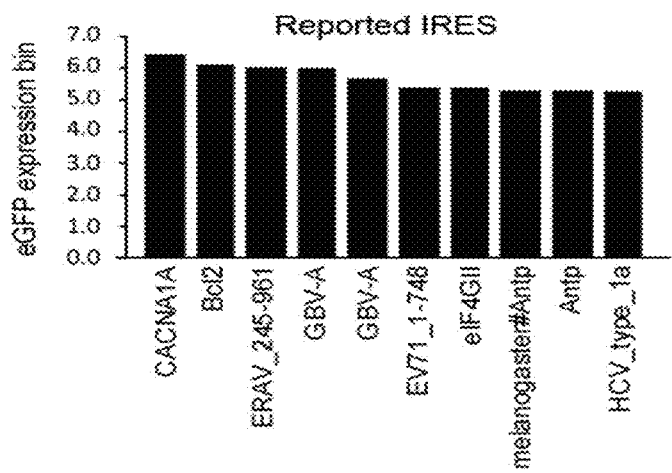
FIG. 10A-10C show the high-throughput IRES screening assay can capture IRES from viral and human 5' UTRs. These figures show examples of IRESs captured in the screening assay with top 10 eGFP expression among the reported IRESs (i.e., linear IRESs) (FIG. 10A), viral 5' UTRs (FIG. 10B), and human 5' UTRs (FIG. 10C).
Figure 10B:
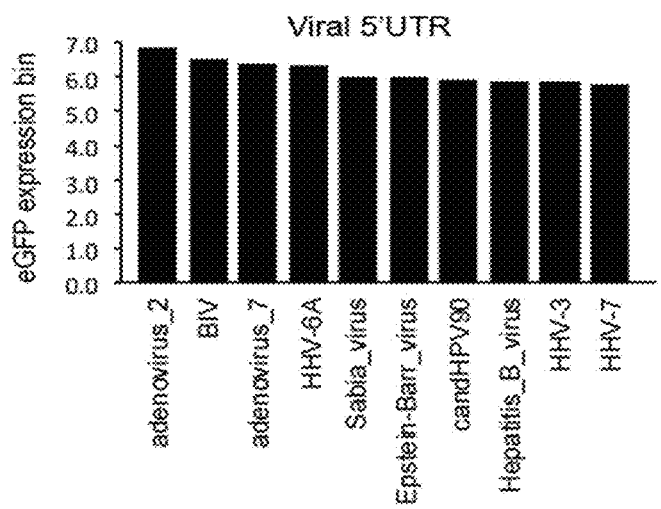
Figure 10C:
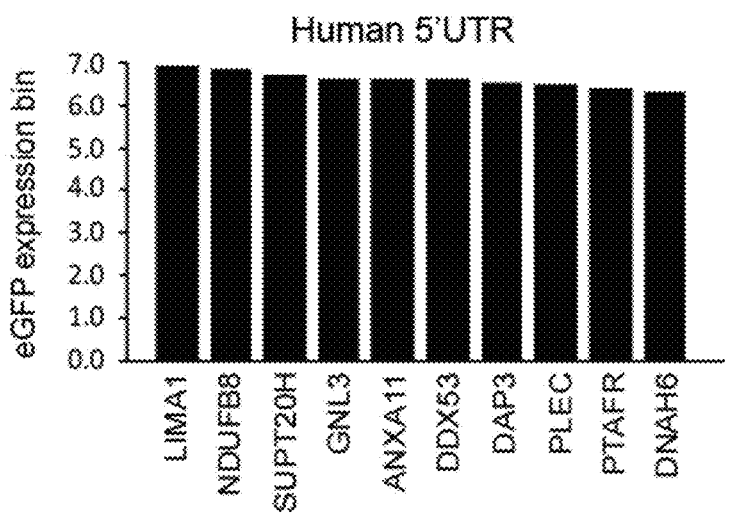

40,855 out of 55,000 oligos were captured from the library (~74.3%). To quantify the eGFP expression level of each oligo, the mean weighted rank distribution of the reads across the bins was calculated. The weight of each bin is the fraction of the number of reads in this bin of its total reads in all seven bins. The rank is the bin number from the bin with the lowest eGFP intensity (bin #1) to the bin with the highest eGFP intensity (bin #7). (FIG. 1B). It was found that the quantification of translation activity was highly reproducible between two independent biological replicates (Pearson's correlation coefficient R=0.70) (FIG. 9A). It was further confirmed that the results were not confounded by the change of circRNA back-splicing efficiency due to different oligo inserts (FIGS. 9B and 9C). This screening assay revealed three groups of oligos according to their eGFP expression level—a group (~2,500) of oligos which showed no eGFP expression (eGFP expression (bin)=0.0), and two groups of oligos showing a bimodal distribution of eGFP expression (eGFP expression (bin)=0.8-2.2 and 2.4-7.0, respectively). To determine the oligos with cap-independent translation activity (eGFP(+) oligos), the weighted rank distribution of the eGFP intensity of the cells transfected with no-IRES-inserted reporter plasmid (empty eGFP circRNA) was calculated as the background eGFP expression. The oligos were defined as eGFP(+) oligos were the oligos with eGFP expression higher than the background eGFP expression (eGFP expression (bin)=3.466387) (FIG. 1B). The background eGFP expression was calculated based on the distribution of the reads across the bins rather than a simple cut off value, which is a more conservative approach to avoid possible false positive events because the empty circRNA eGFP reporter could have weak translation activity (FIG. 9D). With this approach, 17,201 eGFP(+) oligos were identified from the screening assay (FIG. 1B, SEQ ID NO: 1-17201). Further, it was verified that the screening result was not eGFP reporter specific because the eGFP(+) oligos identified were able to initiate circRNA translation of reporters with different coding sequences (CDSs) (FIG. 9E). Although circRNA translation is reproducibly detected, substantially weaker cap-independent translation activity was observed for the circRNA driven by the eGFP(+) oligos compared to the linear RNA translation driven by the cap-dependent translation (FIG. 9F).

Figure 1D:
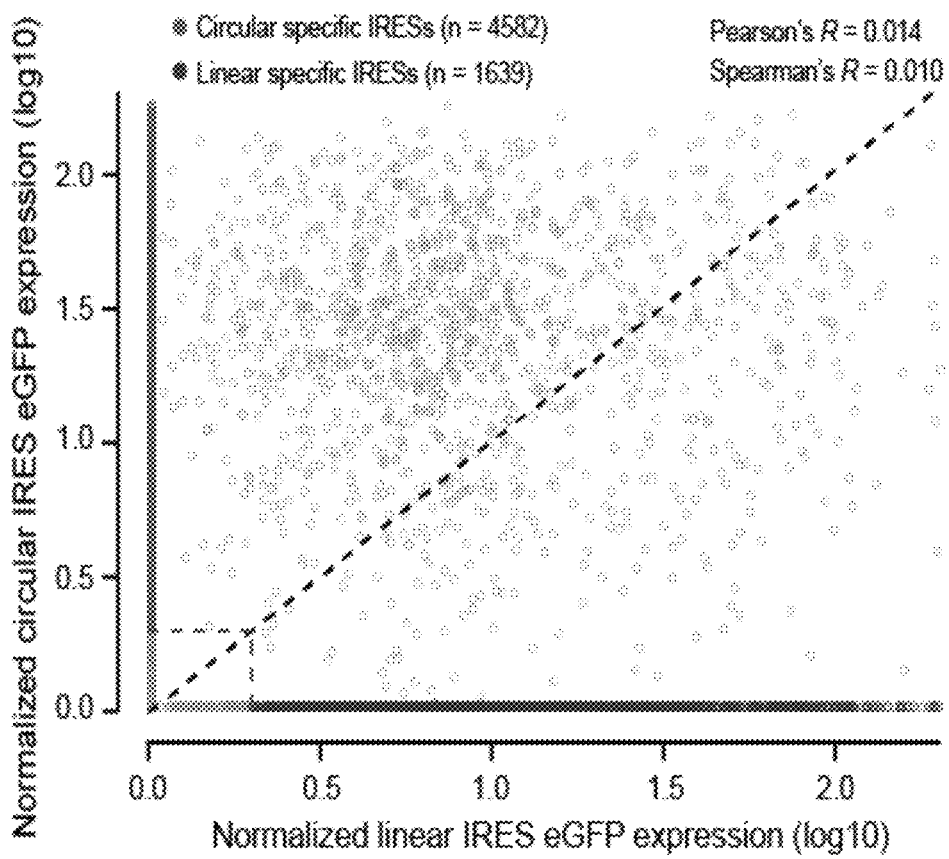

Because a previous study has utilized the same synthetic oligo library on a linear bicistronic eGFP reporter screening assay to identify oligos with cap-independent translation activity on linear RNA over no-IRES-inserted reporter plasmid as threshold (Weingarten-Gabbay et al., 2016), it was possible to compare the cap-independent translation activity of each oligo sequence on linear RNA and circular RNA respectively. For each oligo, the normalized eGFP expression was calculated, from the circRNA vs. from the linear RNA template. It was discovered that among the oligos captured in both circRNA and linear RNA reporter screens (n=13,645), a large number of the oligos showed cap-independent translation activity in both linear and circular RNA screening system (n=7,424) (FIG. 1D, FIG. 11A). However, there was little correlation between the overall IRES activity of circular vs. linear RNA (Pearson's R=0.014; Spearman's R=0.010) (FIG. 1D). Interestingly, some oligos were also captured that show IRES activity specifically in either linear or circular screening system (linear IRES and circular IRES, respectively) (FIG. 1D). To define linear and circular IRES, a more conservative approach was taken, where linear IRES represents the oligo showing cap-independent translation activity in the linear RNA screening system only; and circular IRES represents the oligo showing cap-independent translation activity in the circular RNA screening system only. With this approach, 4,582 circular IRESs and 1,639 linear IRESs were identified (FIG. 1D, FIG. 11A).

Furthermore, when the distribution of the human and viral IRES was examined among circular IRES, linear IRES, and the IRES showing translation activity in both linear and circular RNA, respectively, no significant difference was found among the IRES (FIG. 11B-11D). The result suggests that the recruitment or the activity of circRNA-specific IRES trans-acting factors (ITAFs) on the circular RES may depend on circRNA-specific biogenesis, such as circRNA back-splicing or circRNA nuclear export to distinguish circRNAs from linear RNAs. Together, these results demonstrate that the high-throughput screening assay utilizing the circRNA reporter construct is able to systematically identify the RNA sequences harboring IRES activity that can facilitate cap-independent translation on circRNA.

Example 2

This example demonstrates that synthetic circRNAs harboring eGFP+ oligo sequences are actively translated.

Figure 2A:
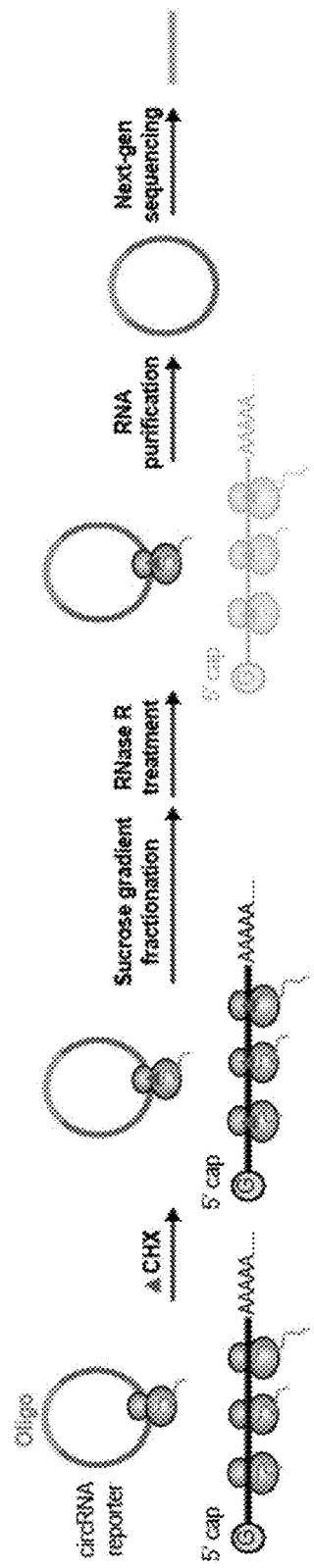
Figure 2D:
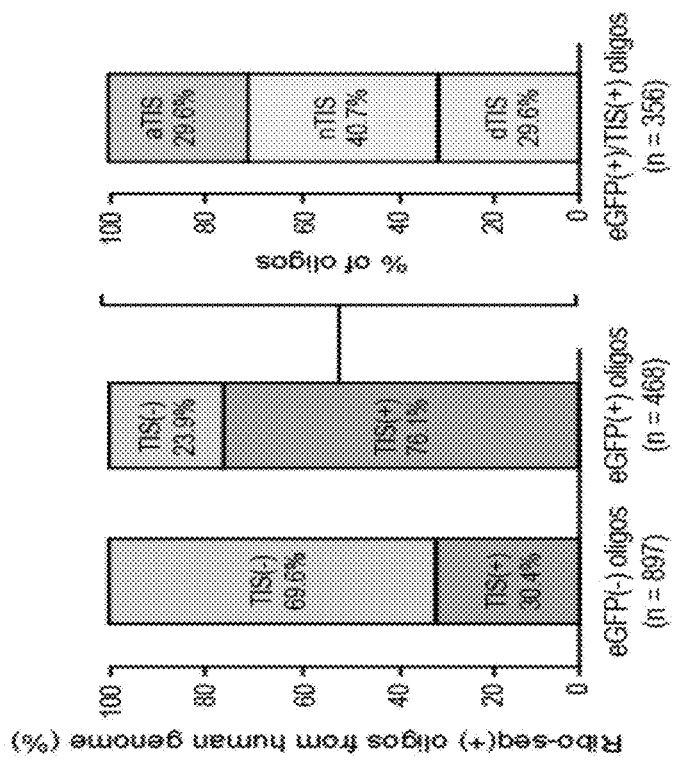
Figure 2E:
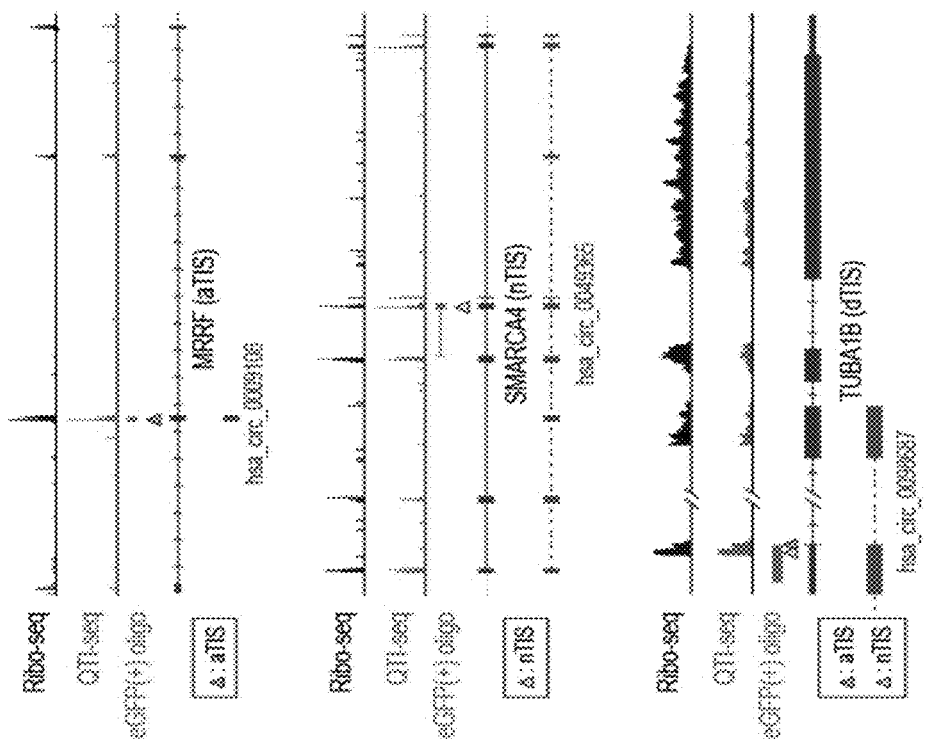
Figure 12A:
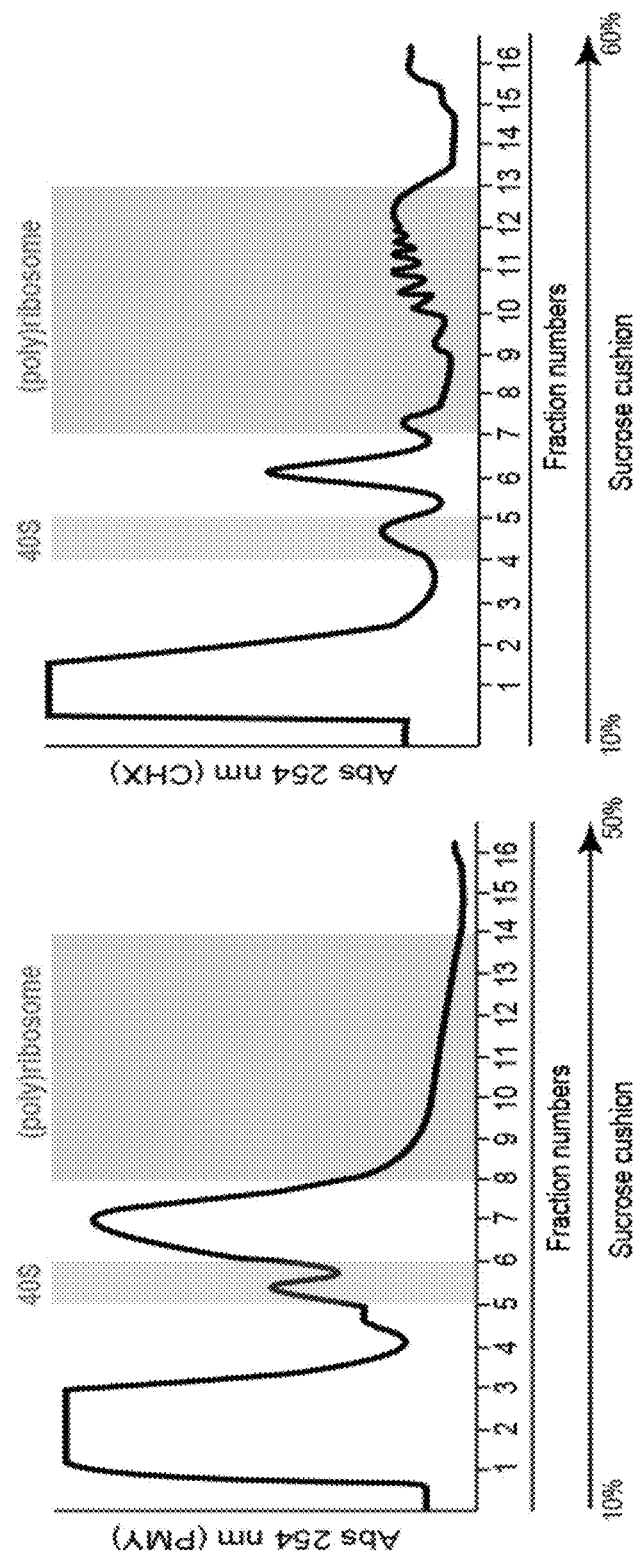
FIG. 12A-12E show that the circRNAs containing the eGFP(+) oligo sequence are more actively translated.
Figure 12C:
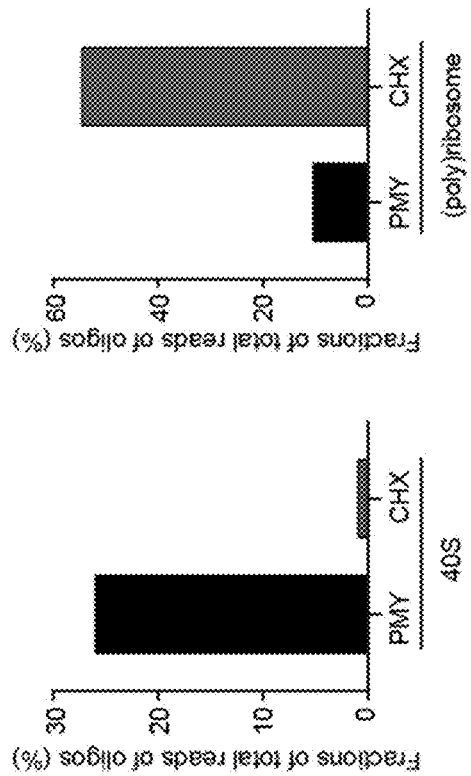
Figure 12E:
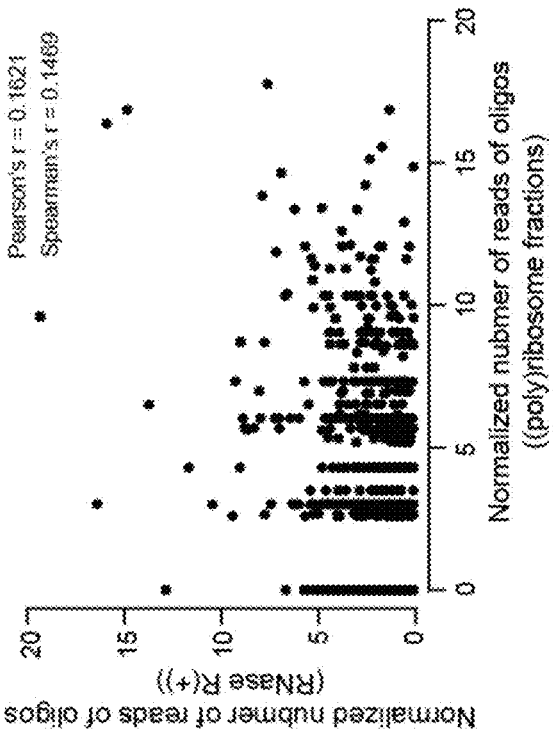
Figure 12B:
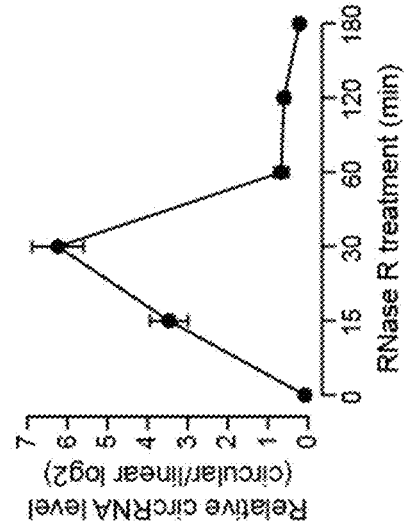
Figure 12D:
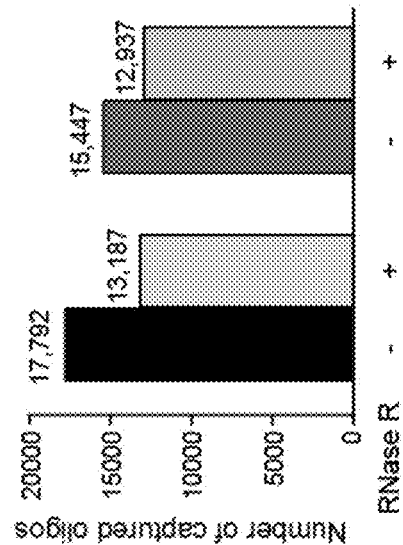

To validate the screening results of Example 1, polysome profiling was used to examine whether circRNAs containing the identified eGFP(+) oligo sequence are actively translated and engaged on the ribosome. First, HEK-293T cells were transfected with the oligo-split-eGFP-circRNA reporter construct containing the synthetic oligo library, treated the transfected cells with cycloheximide (CHX), and isolated (poly)ribosome-associated RNAs with sucrose gradient fractionation (FIG. 2A, 2B, FIG. 12A). Further, the fractions with RNase R were treated to obtain high enrichment of (poly)ribosome-associated circRNAs and high-throughput sequencing was performed to identify the IRES sequences harbored by the circRNA in each fraction. The RNase R treatment was performed in conditions that allows RNase R to digest potential G-quadruplex containing linear RNA efficiently, and the RNase R digestion duration was optimized to obtain >100 fold circRNA enrichment over linear RNA (FIG. 12B). In comparison to the CHX treatment, treating transfected cells with puromycin (PMY) caused translated circRNAs shifting from the poly(ribosome)-associated fractions to the 40S fraction (FIG. 12C), suggesting that CHX treatment is able to capture translated circRNAs. To avoid the result being confounded by the weakly translated circRNAs (data not shown), the ratio of (poly)ribosome-enriched oligos among the eGFP(+) oligos with eGFP expression above the 80th percentile was calculated and compared with the eGFP(−) oligos with eGFP expression below the 20th percentile. The result demonstrated that the eGFP(+) oligos are more enriched in the (poly)ribosome fractions (57.2%) than the eGFP(−) oligos (17.9%) (FIG. 2C). It was confirmed that the higher enrichment of (poly)ribosome-associated eGFP(+) oligos was not caused by the capturing efficiency or the expression level of the oligos (FIGS. 12D and 12E). The result suggests that the circRNAs containing the eGFP(+) oligo sequences are more actively translated. However, since polysome profiling has a lower sensitivity for capturing weakly translated circRNAs (data not shown), quantitative translation initiation sequencing (QTI-seq) data was utilized for additional validation. Next, published data from the QTI-seq was examined, which is a modified ribosome-profiling (Ribo-seq) technique that maps the translation initiation sites (TIS) genome-wide (Gao et al., Nat Methods 12, 147-153, 2015). First, it was examined if the eGFP(+) oligo sequences overlap with those identified TIS on the human transcripts. The results demonstrated that among the oligos derived from the human genome with Ribo-seq coverage, the majority of the eGFP(+) oligos (~76%) overlaps with the identified TIS on human transcripts identified by QTI-seq (TIS(+) oligos), while only 30% of the eGFP(−) oligos are TIS(+) (FIGS. 2D and 2E, FIG. 13A), suggesting that the eGFP(+) oligos are more likely to initiate translation at those TIS than the eGFP(−) oligos. Interestingly, by examining the eGFP(+)/TIS(+) oligos on the human genome, three types of eGFP(+)/TIS(+) oligos were identified: (1) oligos containing the translated initiation site that have been annotated on linear transcripts (annotated TIS; aTIS), (2) oligos containing the translated initiation site that were not annotated on linear transcripts (non-annotated TIS; nTIS) which can be located at the 5' UTR, CDS or 3' UTR region of the transcripts, and (3) oligos containing both aTIS and nTIS signal (dual TIS; dTIS) (FIGS. 2D and 2E). These different types of TIS(+) oligos may suggest that the oligos utilized different mechanisms for initiating translation. While aTIS oligos (~30%) may utilize the same annotated translation initiation site as the linear transcript for cap-independent translation, nTIS (~41%) in contrast represent novel translation initiation sites that are different from the linear transcript for cap-independent translation, which has been observed in initiating the synthesis of alternative translation products. For dTIS oligos, they may utilize some uncharacterized regulatory mechanisms to coordinate the dual activity between aTIS and nTIS which require further investigation. Importantly, while the oligo library was enriched of the oligos located at the upstream of the annotated start codon, no bias was observed towards the ratio of aTIS oligos, suggesting that the result was not confounded by the design of the oligo library. Interestingly, it was found that eGFP(+)/TIS(+) oligos are located within the genomic regions that encode annotated circRNAs (FIG. 2D), which suggests that these circRNA may utilize the TIS on the oligo for initiating endogenous circRNA translation. Nevertheless, when the position of translation initiation sites was mapped on each oligo, no translation initiation hot spots were observed on the oligo (FIG. 13B), suggesting that the translation initiation is not influenced by the position on the oligo. Together, the results above provide strong evidence that the screening assay described herein is able to identify the oligo sequences that are capable of facilitating cap-independent translation activity on circRNAs.

Example 3

This example describes the identification of 18S rRNA complementary sequences that facilitate circRNA translation.

Figures 3I, 3J:
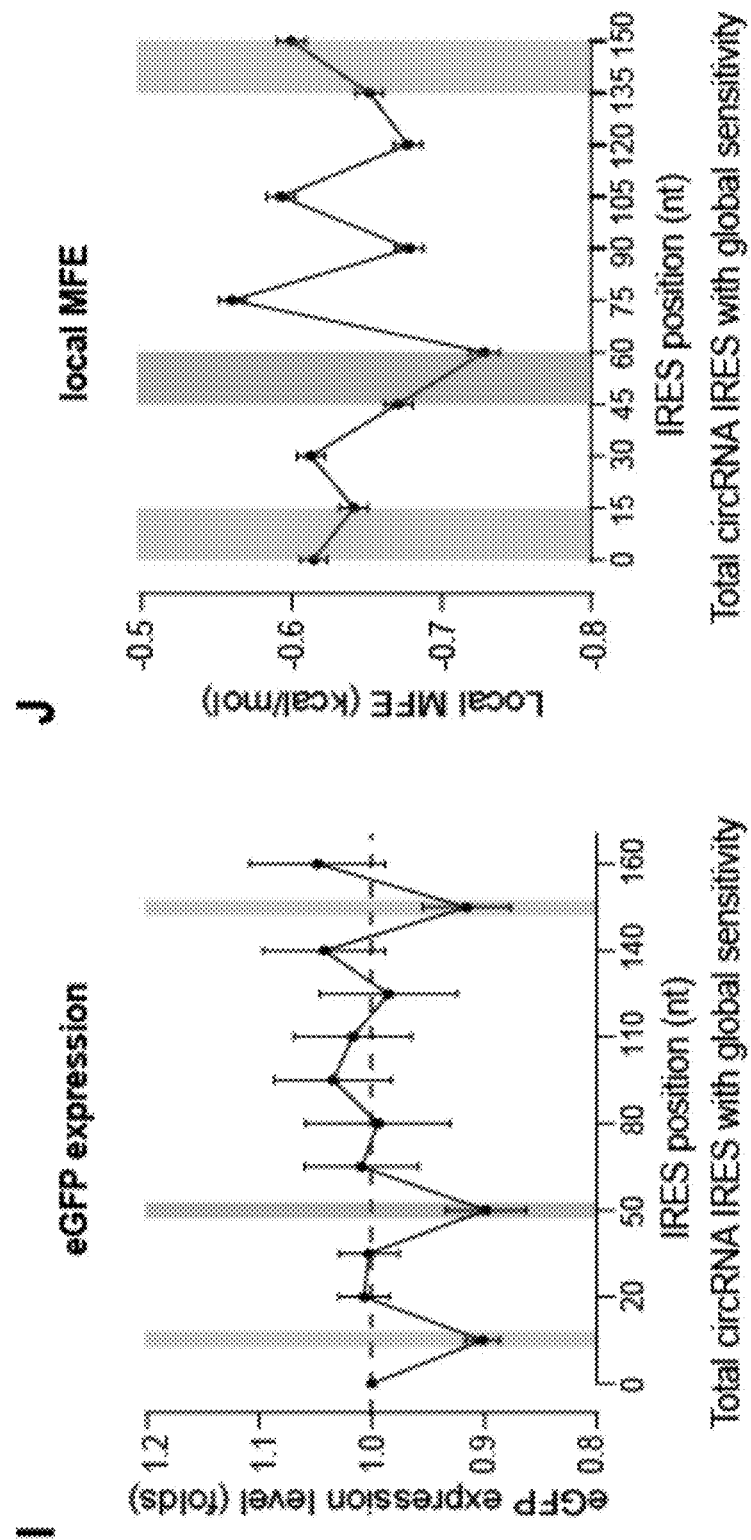

Watson-Crick base-pairing between IRES and 18S ribosomal RNA (18S rRNA) has been demonstrated to facilitate cap-independent translation of linear mRNAs. Thus, it was evaluated whether the screen may identify the regions on human 18S rRNA that can interact with circRNA IRES and facilitate cap-independent translation. The synthetic oligo library was designed to contain 171 oligos with sequences complementary to human 18S rRNA, with a 10-nt sliding window between each consecutive oligo that reconstitutes the entire 1869-nt full-length 18S rRNA sequence (FIG. 3A, SEQ ID NO: 28977-28983). For each position on the 18S rRNA, the average eGFP expression of all the oligos containing the corresponding complementary sequence was calculated. With this sliding window method, the circRNA IRES activity was determined for each 10-nt window across the human 18S rRNA sequence (FIG. 3A). Six "active regions" on the 18S rRNA were identified, where the complementary sequence within these active regions shows average eGFP expression higher than the background eGFP expression (FIG. 3B). Interestingly, active regions 2, 4, 5, and 6 harbor helices that have been reported to contact mRNAs in the eukaryotic ribosome initiation complex and interact with translated RNAs (Pisarev et al., EMBO J 27, 1609-1621 (2008)) (FIG. 3C). Furthermore, active region 4, and active regions 2 and 6, harbored the sequences that have been characterized to facilitate cap-independent translation of IGF1R and HCV IRES, respectively, by Watson-Crick base pairing (FIG. 3C). Active region 3 is located in one of the expansion segments on 18S rRNA (ES6S), which has been implicated in the recruitment of eukaryotic initiation factor 3 (eIF3). eIF3 directly binds to the 5' UTR N6-methyladenosine (m6A) of linear mRNA and initiates cap-independent translation, suggesting that active region 3 on 18S rRNA may be crucial for eIF3-m6A-mediated cap-independent translation. Active region 1 is located in another expansion segment on 18S rRNA (ES3S) that interacts and forms a tertiary structure with active region 3, which suggests that active region 1 may be involved in the eIF3-m6A-mediated cap-independent translation as well. These results suggest that the active regions on 18S rRNA identified indeed play roles in facilitating cap-independent translation.

Figure 13C:
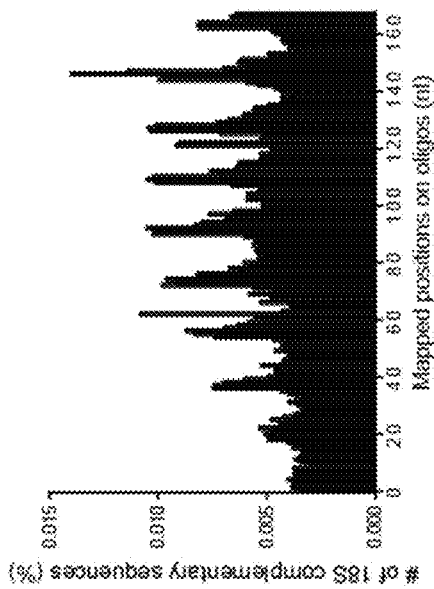
FIG. 13A-13D show that eGFP(+) oligos are more frequently overlapped with the translation initiation sites (TIS) on the human genome. Shown in FIG. 13A is quantification of the number of TIS reads in eGFP(+) or eGFP(−) oligos on the human genome. **** represents p-value <0.001 by an unpaired two-sample t-test. Error bar: SEM. Shown in FIG. 13B are the mapped positions of TIS on each TIS(+) oligo plotted on the oligo. The TIS positions were sorted by the mapped position on the oligo.
Figure 13B:
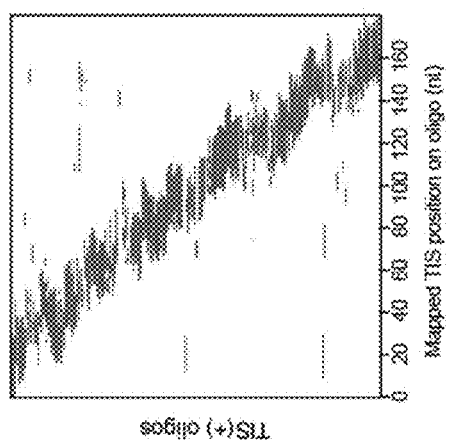
Figure 13A:
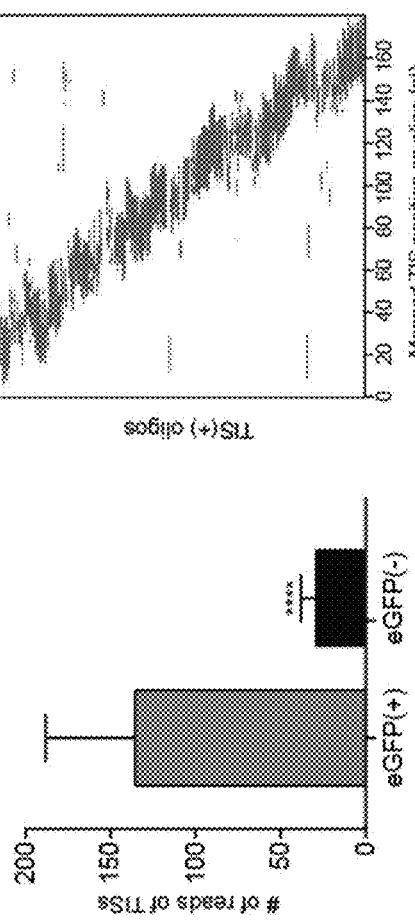
Figure 13D:
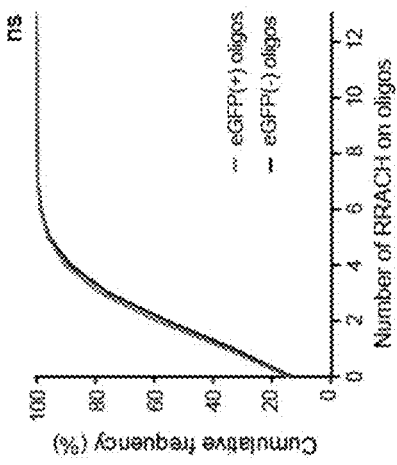

Since the 7-mers derived from active region 4 have been shown to be enriched in reported IRES for linear RNAs, all 7-mers were extracted from the sequence complementary to the active regions of 18S rRNA (active 7-mers), and the number of active 7-mers harbored by the eGFP(+) and eGFP(−) oligos, respectively, were compared. It was found that eGFP(+) oligos have higher enrichment of active 7-mers than eGFP(−) oligos (FIG. 3D). In contrast, when the matched-number of random 7-mers which do not overlap with the active 7-mers between eGFP(+) and eGFP(−) oligos was compared, no significant difference was found (FIG. 3D), suggesting that the higher enrichment of active 7-mers in eGFP(+) oligos observed here is specific to the 18S rRNA complementary sequence. Nevertheless, no hot spot positions of the active 7-mers located on the circRNA IRES were observed (FIG. 13C). To further validate the results, the 18S rRNA complementarity of the IRES was perturbed by either substituting the 18S rRNA complementary sequence with a random 7-mer or adding the flanking 18S rRNA complementary sequence to the IRES and measured their circRNA translation activity (FIG. 3E). Diminished IRES activity was observed with lower 18S rRNA complementarity on the IRES, and conversely stronger IRES activity was programmed with higher 18S rRNA complementarity added to the IRES (FIG. 3E). These results suggest that the circRNA IRES containing RNA sequence complementary to the active regions on 18S rRNA is one of the regulatory elements that can facilitate cap-independent translation on circRNA.

Example 4

This example describes the identification of essential elements on circRNA IRES using systematic scanning mutagenesis.

Scanning mutagenesis was employed to define the essential elements on circRNA IRES. Included in this analysis were oligos designed for scanning mutagenesis of 99 reported IRESs and 734 native 5' UTRs in the synthetic oligo library. The oligos were designed as non-overlapping sliding windows of 14-nt random substitution mutation tiling across the entire IRES or 5' UTR (FIG. 3F). With the screening results, it was possible to determine the effect of the substitution mutations on each 14-nt window on IRES activity across each oligo sequence (FIG. 3F). The essential elements (FIG. 3G; highlighted in blue) were determined as the region from the start position of the mutation (FIG. 3G; black dots) where there was a sharp decrease of the IRES activity to the next start position of the mutation where the IRES activity was resumed or above the mean eGFP expression level. By comparing the quantification result with a well-characterized IRES, hepatitis C virus (HCV) IRES, it was observed that the known functional domains on the HCV IRES (FIG. 3G; redlines) co-localized with the mutation positions that have dramatically reduction in IRES activity. The specific reduction in IRES activity at those mutation positions suggested that the mutations disrupted essential elements of the IRES, abolishing its cap-independent translation activity. The results demonstrated that the assay can indeed capture all of the reported essential elements on the HCV IRES, as well as one possible novel essential element that has not been characterized yet (FIG. 3G).

The same scanning mutagenesis assay was also utilized to further identify the essential elements on the identified circRNA IRES by scanning mutagenesis. The synthetic oligo library contains oligos carrying sliding windows of 14-nt random substitution mutation tiling across the circRNA IRES. With the scanning mutagenesis, two classes of circRNA IRES were captured—circRNA IRES with local sensitivity, which shows reduction in circRNA IRES activity only when a specific position in mutated (FIG. 3H; top), and circRNA IRES with global sensitivity, which mutation in most positions can cause reduction in IRES activity (FIG. 3H; bottom). The local and global sensitive IRES were defined as whether the IRES activity was affected by a single mutation or multiple mutations, respectively. The global sensitive IRESs have more structured sequences (i.e., significantly lower minimum free energy (MFE) value) compared to local sensitive IRESs; which suggests that the overall secondary structure of global sensitive IRESs are crucial for their IRES activity, because the more structured sequences are more likely to be affected by the mutation regardless of the position of the mutation. On the other hand, local sensitive IRESs have less structured sequences and are more resistant to the mutation; which suggests that the IRES activity of local sensitive IRESs may be regulated by a short sequence as the essential element.

By overlaying the eGFP expression level of all the captured circRNA IRESs with global sensitivity, three regions (5-15 nt, 40-60 nt, and 135-165 nt) were identified on the IRES, where when the mutation hit these regions, the IRES activity decreased significantly (FIG. 3I), suggesting that these regions may harbor the key elements for facilitating cap-independent translation of the circRNA IRES. To further characterize if the element harbored by the regions is structure-dependent, the local MFE was calculated along the circRNA IRESs with global sensitivity in a 15 nt non-overlapping window. It was discovered that the local MFE of the 40-60 nt region on the circRNA IRES shows significantly lower local MFE (FIGS. 3I and 3J; shaded in red), suggesting that this region may harbor the local structural element that can drive circRNA translation. In contrast, the local MFE of 5-15 nt and 135-165 nt regions do not differ from other regions on the IRES (FIGS. 3I and 3J; shaded in blue), which suggests that the regulatory elements located at these two regions are not involved in local secondary structures.

Taken together, this data indicates that, with scanning mutagenesis, the assay is able to determine circRNA IRES with local or global sensitivity, and systematically identify essential circRNA IRES elements that are required for IRES activity in a high-throughput manner.

Example 5

This example demonstrates that a stem-loop structure at distinct positions on circRNA IRESs facilitates cap-independent translation.

Figure 14A:
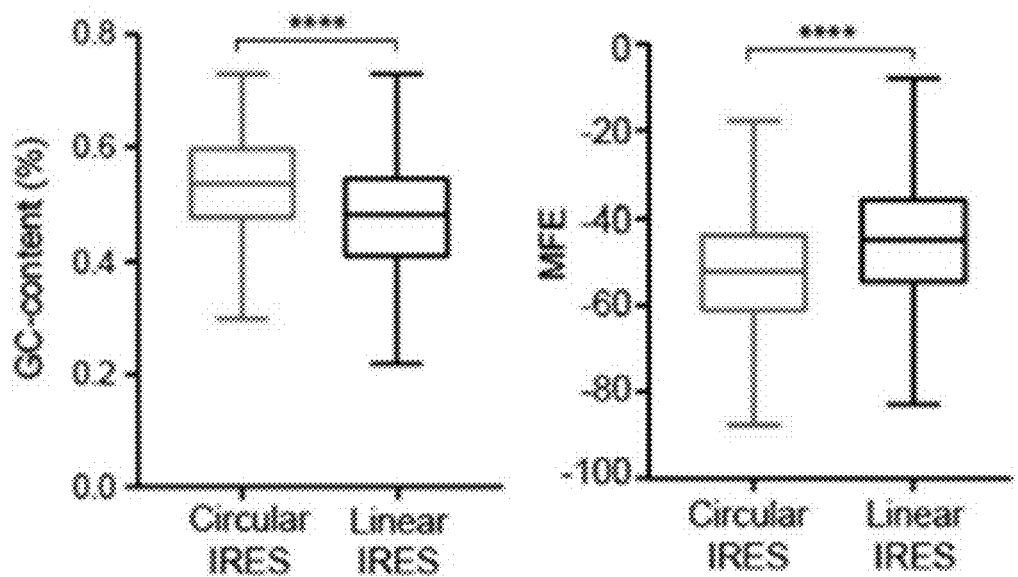
FIG. 14A-14G show a feature comparison between linear and circular IRES sequences. Shown in FIG. 14A is quantification of the GC-content (left) and MFE (right) of circular IRESs and linear IRESs, plotted as Tukey box-plot (outliers not shown). **** represents p-value <0.001 by an unpaired two-sample t-test.
Figure 14B:
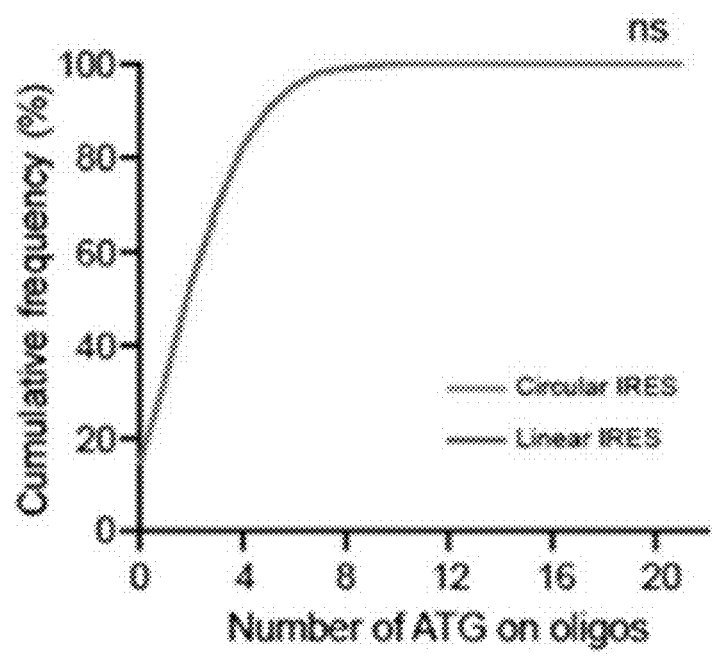
Figure 14C:
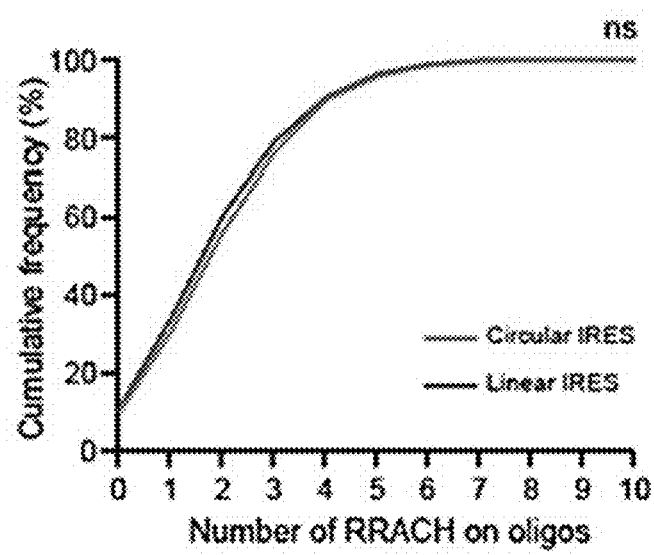
Figure 14D:
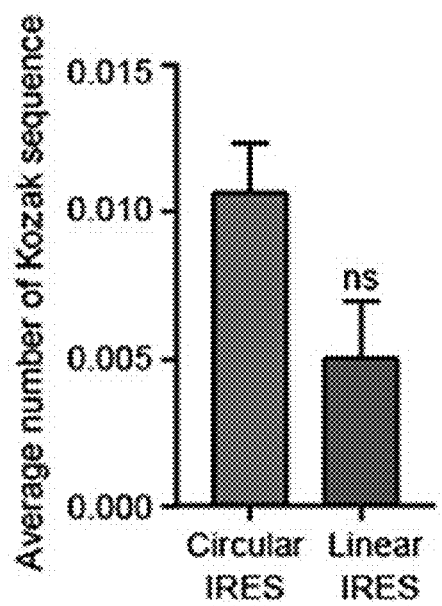

While many native and synthetic IRES have been reported to be able to facilitate cap-independent translation on circRNA, most of the IRES were characterized in a linear RNA reporter system, and no differential IRES activity of IRES on linear vs. circular RNA has been reported yet. By comparing the screening results from the circRNA reporter system described herein with the previous screening study done on a linear RNA reporter system using the same synthetic oligo library, two distinct groups of oligos were identified that harbor IRES activity on either linear or circular RNA specifically (linear IRES and circular IRES, respectively). To characterize the features on these oligos that can distinguish linear and circular IRESs, the primary sequence of the oligos was analyzed, and it was discovered that circular IRES contain higher GC-content and lower MFE than linear IRES (FIG. 14A). On the other hand, the number of the canonical translation start-codon (AUG), the Kozak consensus sequence (ACCAUGG, SEQ ID NO: 34039), and the m6A motif (RRACH, SEQ ID NO: 33944) showed no difference between linear and circular IRESs (FIG. 14B-14D). Since RNA with low MFE often indicates that the RNA has a stable secondary structure, the low MFE of circular IRES suggests some structural elements may play a role in facilitating cap-independent translation activity on circRNA.

Figure 14E:
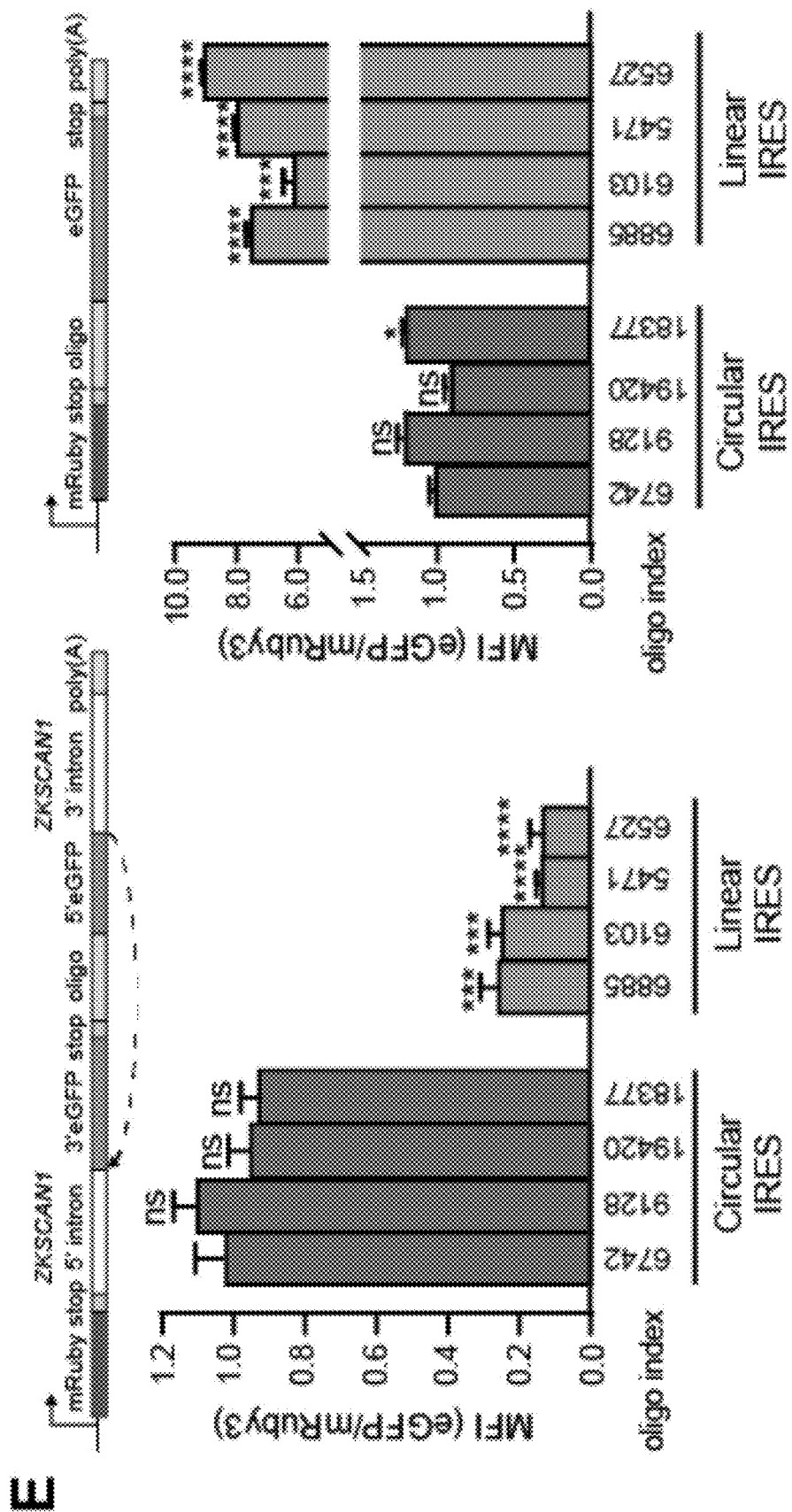
Figure 14F:
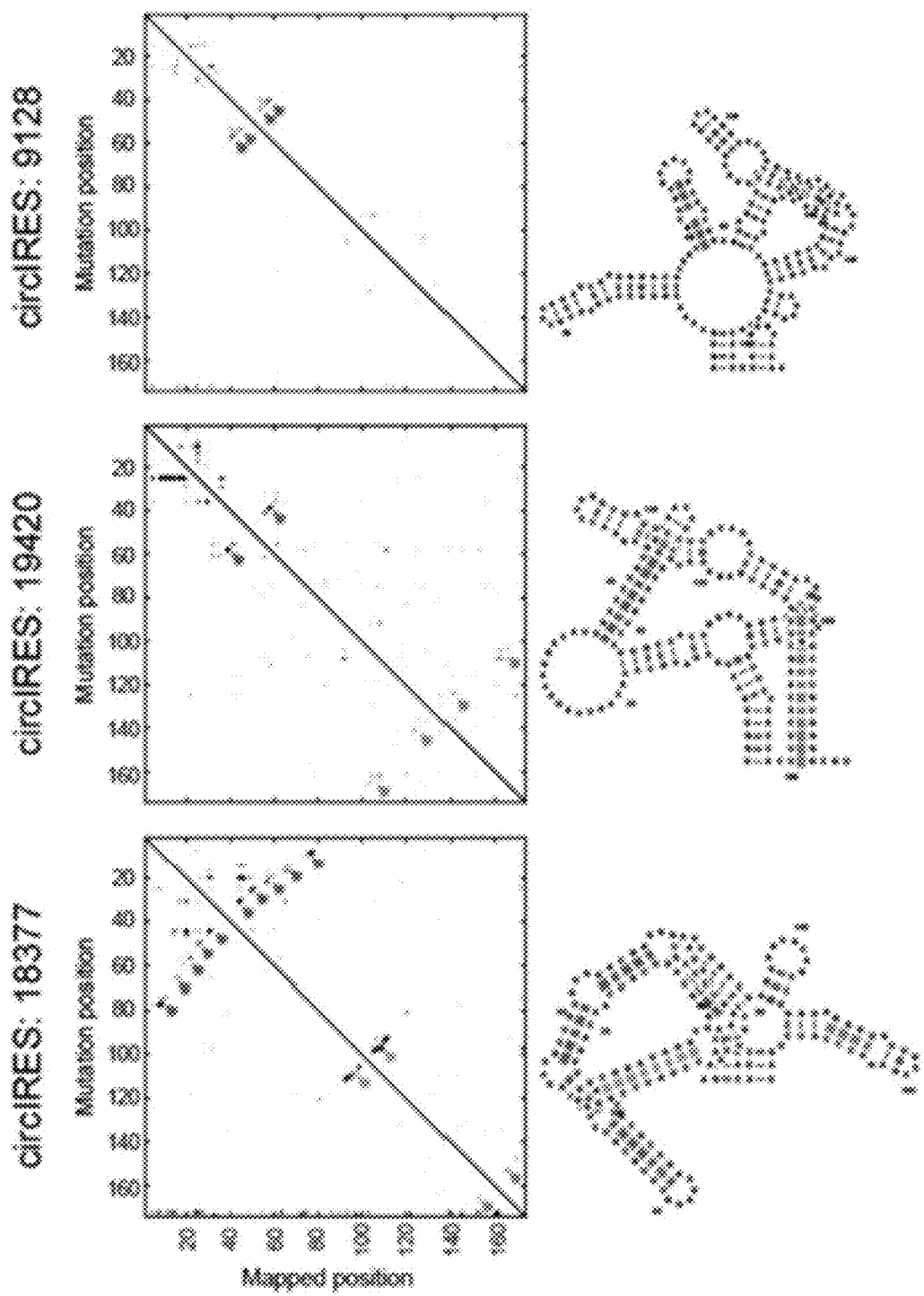
Figure 14G:
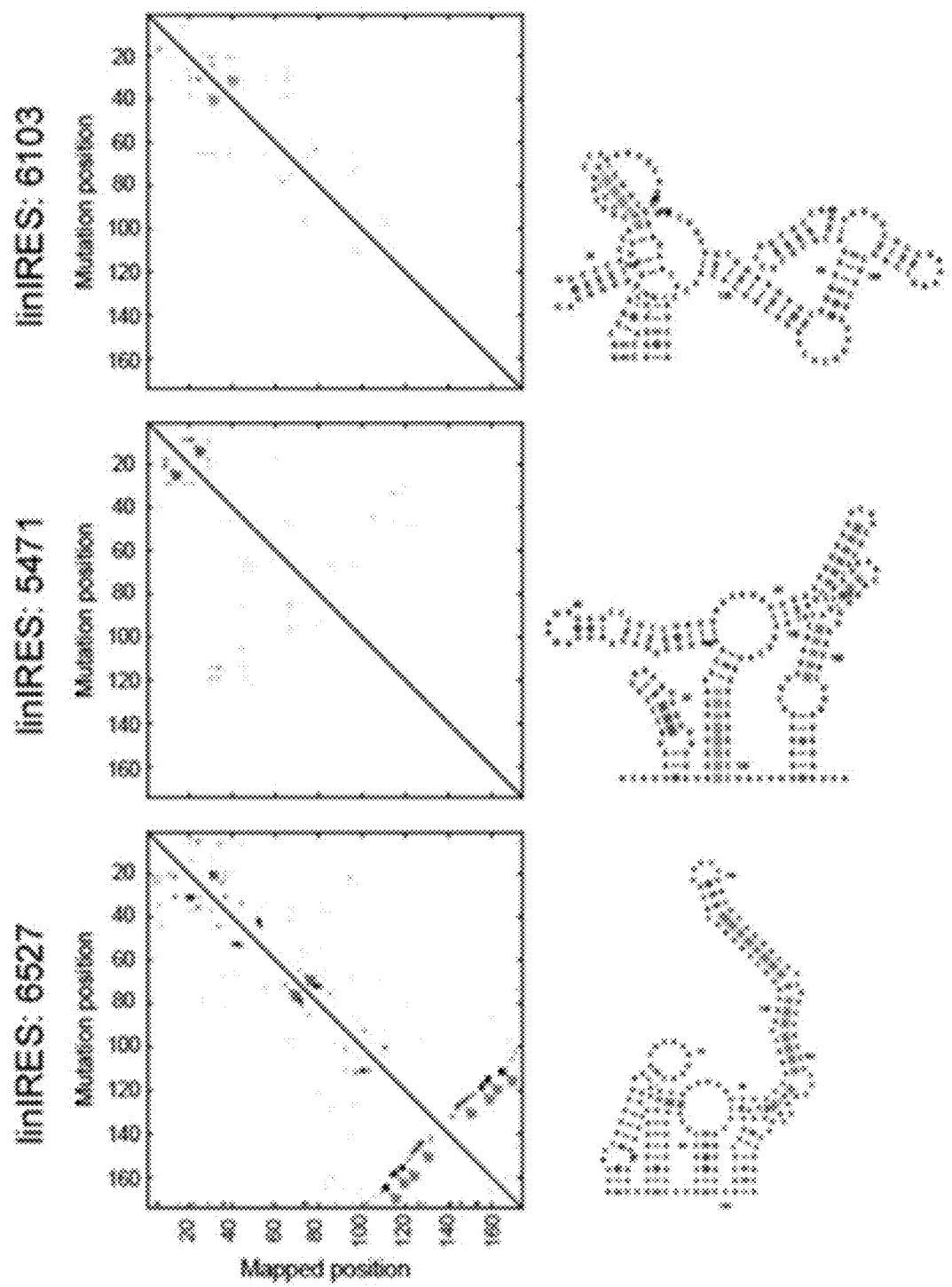

The secondary structure of linear and circular IRES was then characterized with M2-seq, an assay of systematic mutational profiling and chemical structure probing that captures RNA secondary structure with very low false-positive rate. Four circular IRES and linear IRES were selected that specifically show IRES activity on circRNA or linear RNA, respectively (FIG. 14E) and their secondary structure was determined with M2-seq. These oligos were selected because they harbor strong IRES activity in circular RNA system (circular IRES: 6742, 9128, 19420 and 18377) or linear RNA system (linear IRES: 6885, 6103, 5471 and 6527), respectively, and do not show any activity of read-through translation, ribosome re-initiation, and hidden promoter activity on the linear bicistronic construct to ensure that the eGFP signal detected here on the linear bicistronic construct came from the cap-independent translation of the oligos. The M2-seq results revealed that while linear IRES harbored structured elements, the circular IRES are in general more structured than linear IRES (FIGS. 4A and 4B, FIGS. 14F and 14G). Among all four circular IRES examined, all contained a stem-loop structured RNA element (SuRE) on the IRES at a distinct position (40-60 nt position from the +1 position (the first nucleotide) of the IRES), while all the linear IRES examined did not contain such a structure at this position (FIGS. 4A and 4B, FIGS. 14F and 14G). In line with previous systematic scanning mutation profiling, which also suggests that this distinct position on IRES contains structural element required for facilitating circRNA translation (FIGS. 3I and 3J), it was proposed that the SuRE at this distinct position on the IRES can facilitate cap-independent translation activity on circular IRES.

Figures 4E, 4F:
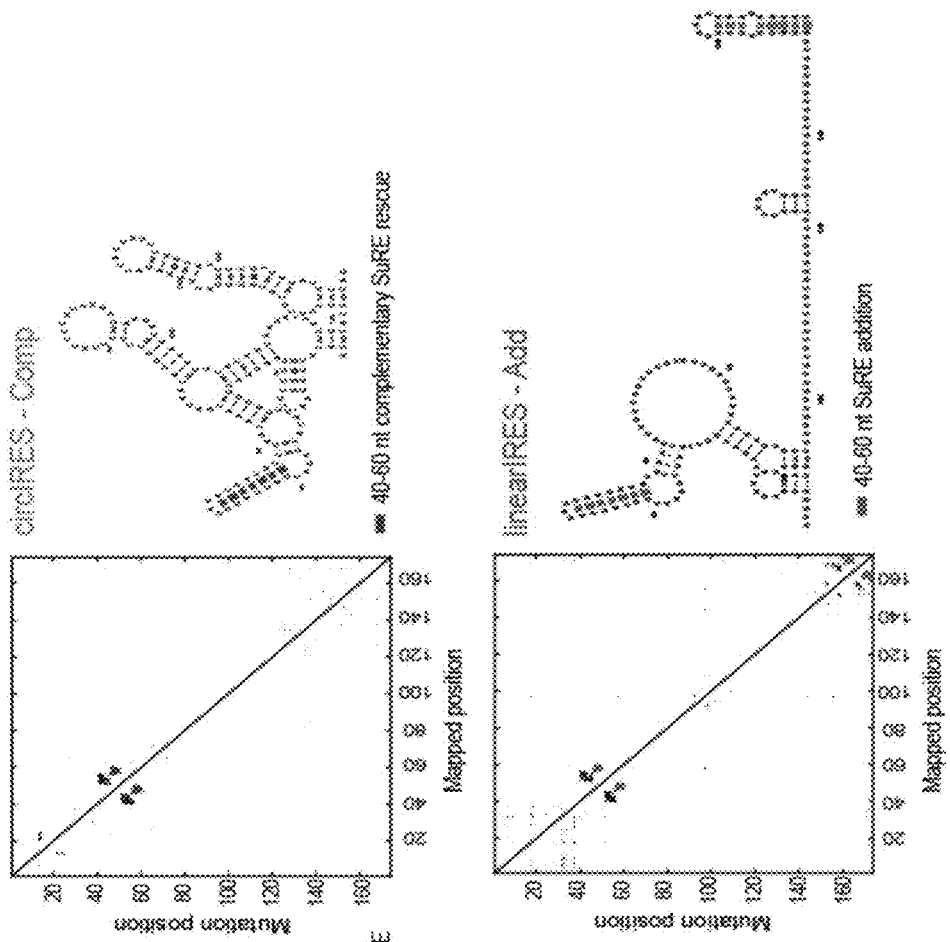
Figures 4G, 4H:
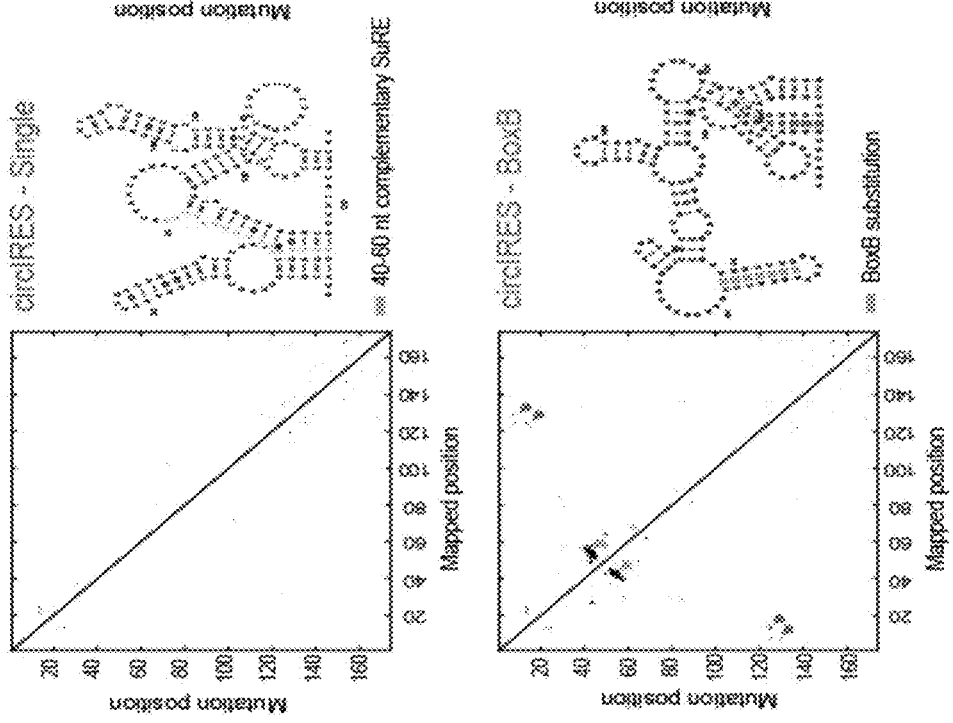
Figure 4I:
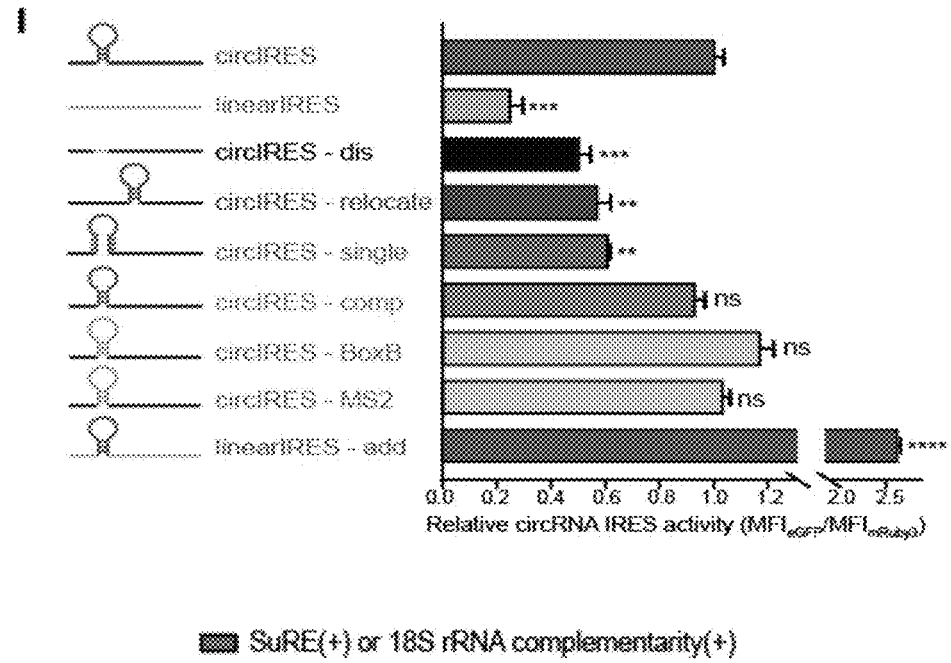

To test this hypothesis, the SuRE at 40-60 nt position on the circular IRES (oligo index: 6742) was disrupted by substituting it with the sequence extracted from the same position on the linear IRES (oligo index: 6885), forming a different secondary structure at this position (FIG. 4C). Interestingly, disrupting the SuRE at this position on the circular IRES leads to a reduction in its IRES activity (FIG. 4I). Moreover, to test if the SuRE element is position sensitive, the SuRE element was relocated from the 40-60 nt position to the 90-110 nt position by swapping the sequences of these two regions on the IRES. A decreased translation activity of the IRES was observed (FIGS. 4D and 4I). To further validate that the SuRE is structural dependent rather than sequence-dependent, compensatory mutagenesis of the SuRE element was performed. Specifically, each of the seven base pairs on the stem region of the SuRE element were mutated to disrupt its duplex structure. Lower translation activity of the IRES was observed (FIGS. 4E and 4I). Furthermore, the translation activity of the IRES can be rescued by compensatory double complementary mutations to restore each of the seven base pairs on the stem region (FIGS. 4F and 4I). Interestingly, when the SuRE was substituted with MS2 or BoxB, which have a similar RNA structure, the same IRES activity was observed as the wild-type IRES (FIGS. 4G and 4I), suggesting that the IRES activity regulated by the SuRE is indeed structure-dependent rather than sequence-dependent. Finally, the linear IRES was converted into a circular IRES by transplanting the SuRE from the circular IRES to the 40-60 nt position on the linear IRES (FIGS. 4H and 4I). The results above suggest that the 40-60 nt SuRE on the IRES can indeed facilitate circRNA translation.

Figure 4J:
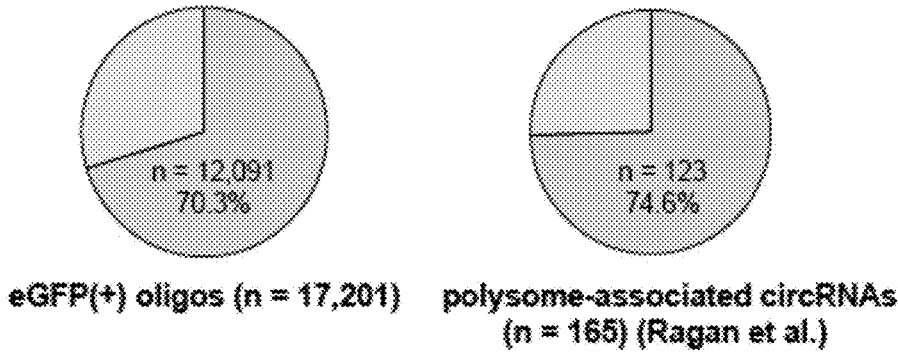
Figure 4K:
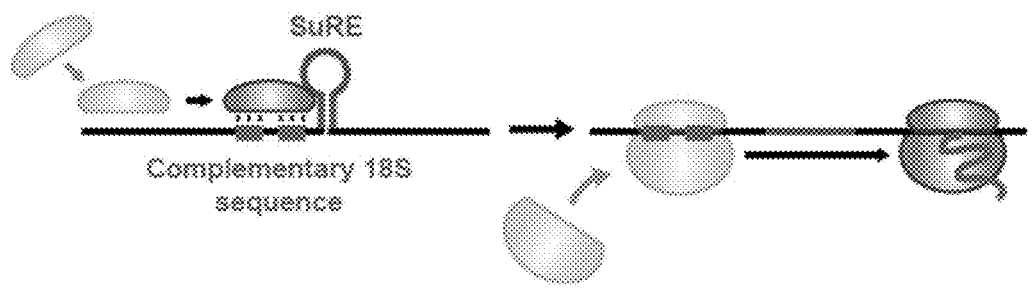

Together, the results above along with the 18S rRNA profiling suggest that two key regulatory elements on circRNA IRES, the 18S rRNA complementarity and 40-60 nt SuRE on the IRES, can facilitate cap-independent translation on circRNA. In line with this model, among the 17,201 eGFP(+) oligos captured by the screen, 12,091 of them (~70%) harbor high 18S rRNA complementarity (18S rRNA complementarity (+)) or 40-60 nt SuRE (SuRE(+)) (FIG. 4J), which suggests that these two regulatory elements can facilitate the exogenous reporter circRNA translation. To further validate if these two regulatory elements can also facilitate endogenous circRNA translation, the polysome-associated circRNAs (translating circRNAs) captured in HEK-293 cells (Ragan et al., 2019) were examined, and it was found that 123 out of 165 endogenous translate circRNAs (~75%) are 18S rRNA complementarity (+) or 40-60 nt SuRE(+) circRNAs (FIG. 4J), indicating that these two regulatory elements are common features among the endogenous translated circRNAs. These results suggest that the 18S rRNA complementarity and 40-60 nt SuRE can facilitate the translation of both exogenous reporter circRNAs and endogenous circRNAs. Nevertheless, no preferential localization of the 18S complementary sequence to the 5' or 3' of the SuRE was observed (FIG. 13C); this suggests that the SuRE on the IRES may cause a pause for RNA unwinding, increasing the chance for the 18S complementary sequence on the IRES to interact with the 18S 25 rRNA on the ribosome, and facilitate cap-independent translation on circRNAs (FIG. 4K).

Example 6

This example demonstrates that the IRES elements facilitate translation initiation of endogenous circRNAs.

Figure 5A:
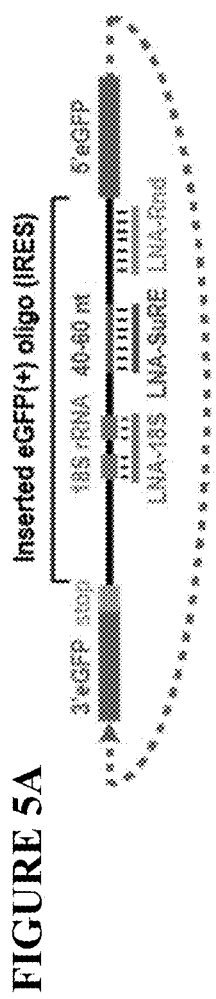
FIG. 5A-5E show that IRES elements facilitate translation initiation of endogenous circRNAs.
Figure 5B:
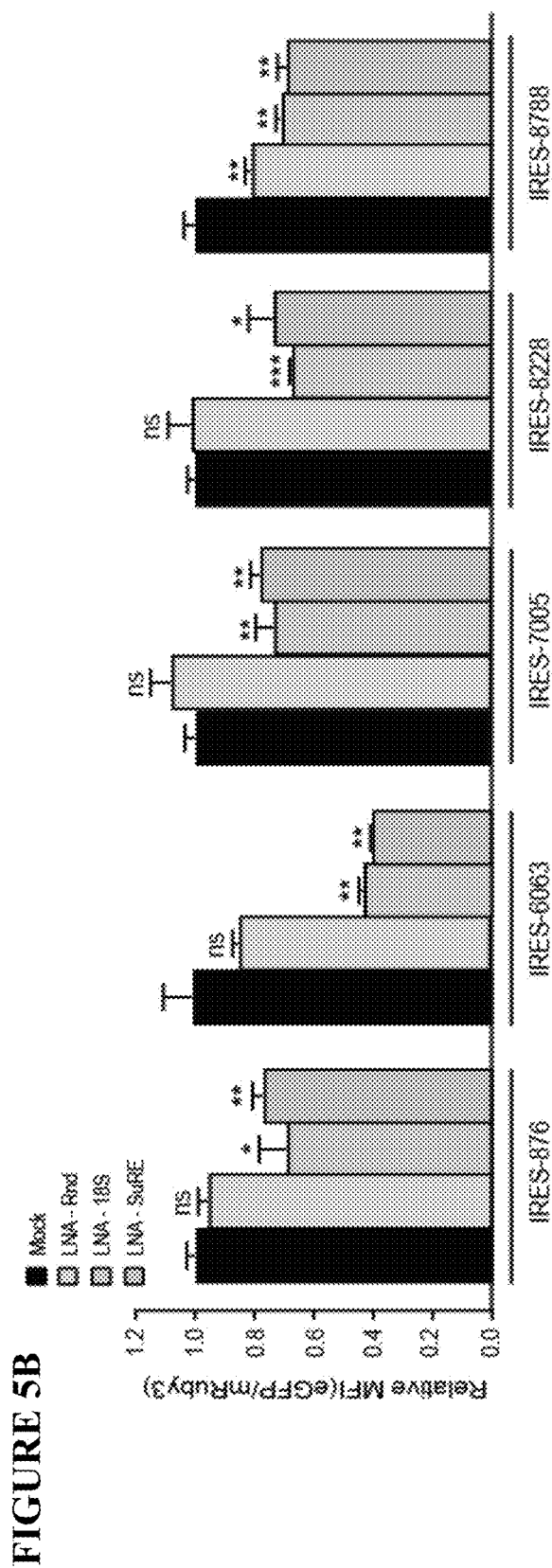
Figure 15A:
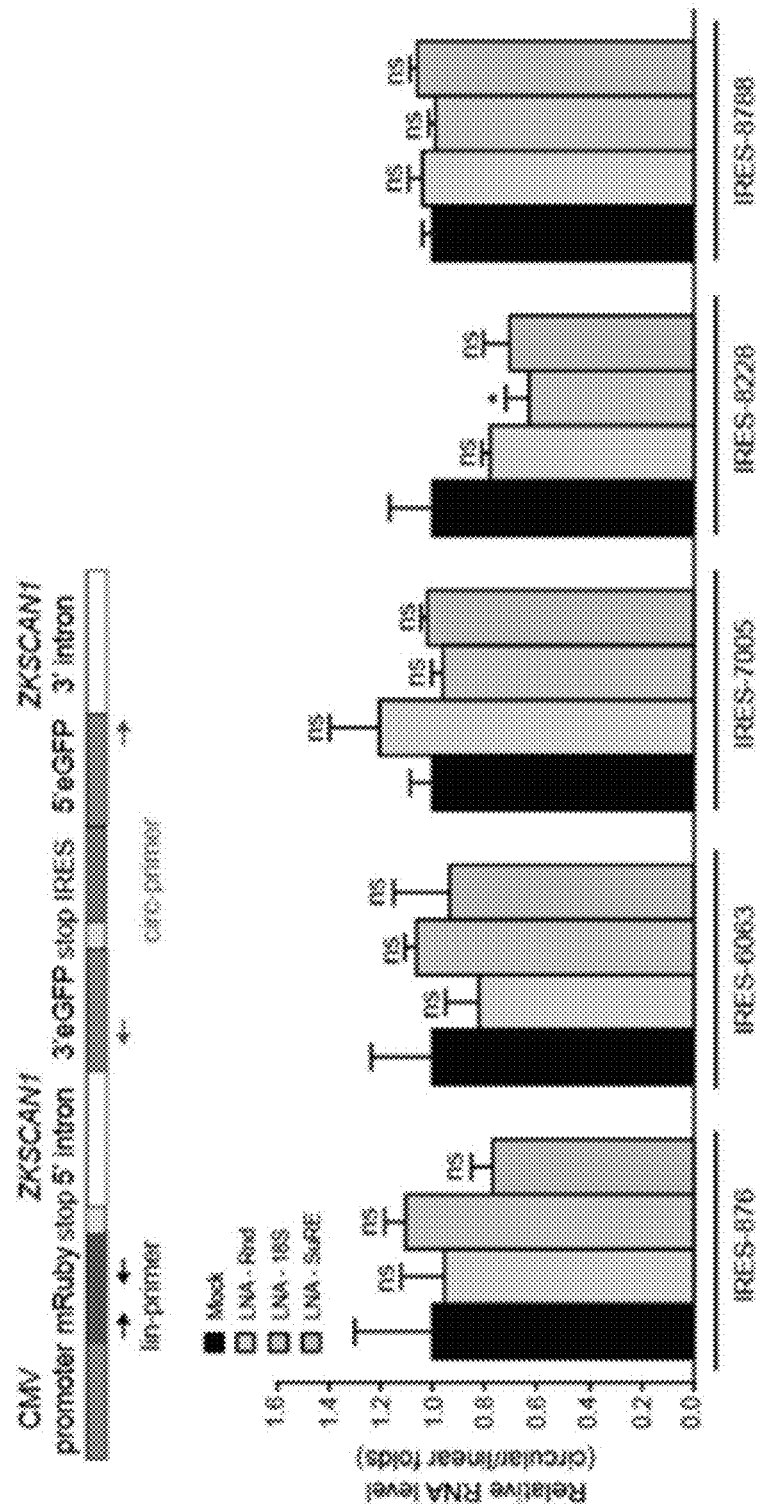
FIG. 15A-15B show that IRES elements facilitate translation initiation of endogenous circRNAs.

To examine if the key regulatory elements identified on the IRES, such as the 18S rRNA complementary sequence and the SuRE at the 40-60 nt position, can facilitate translation of human endogenous circRNAs, a locked nucleic acid (LNA) was utilized to disrupt these key elements on the IRES because LNA has been utilized to specifically disrupt the functional regions on the HCV IRES and inhibit HCV IRES activity. Anti-sense LNAs were designed targeting (i) the 18S rRNA complementary sequence on the IRES to block 18S rRNA binding to the IRES (LNA-18S), (ii) the SuRE at the 40-60 nt position to disrupt the SuRE on the IRES (LNA-SuRE), and (iii) random position downstream of the LNA-18S or LNA-SuRE on the IRES (LNA-Rnd) for identified IRESs (FIG. 5A). The LNAs were then co-transfected with the oligo-split-eGFP-circRNA reporter construct containing the corresponding IRES, respectively, and translation activity of the eGFP reporter was measured by its normalized fluorescence signal intensity. It was found that co-transfecting LNA-18S or LNA-SuRE can indeed disrupt the cap-independent translation activity of all IRESs (10 out of 10 LNAs), while most of the LNA-Rnd co-transfection did not affect the translation activity of the IRES (4 out of 5 LNAs) (FIG. 5B). It was also confirmed that the result was not confounded by the change of circRNA expression level because co-transfecting the LNAs generally did not change the circRNA expression level (FIG. 15A). The result suggests that disrupting the key elements on the IRES with LNA can affect the cap-independent translation activity of the exogenous reporter circRNA.

Figure 5C:
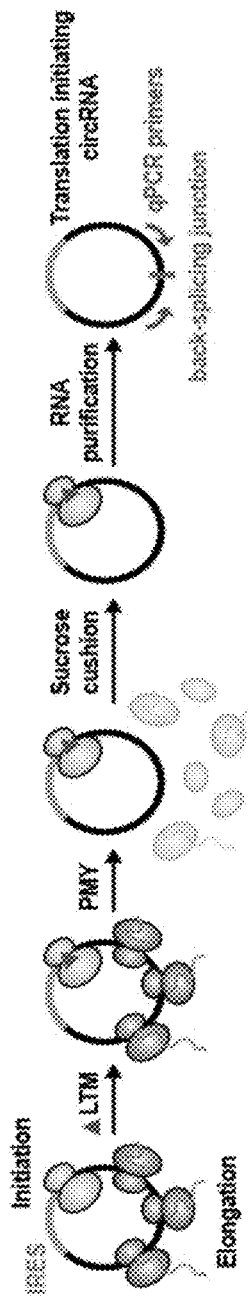
Figure 5D:
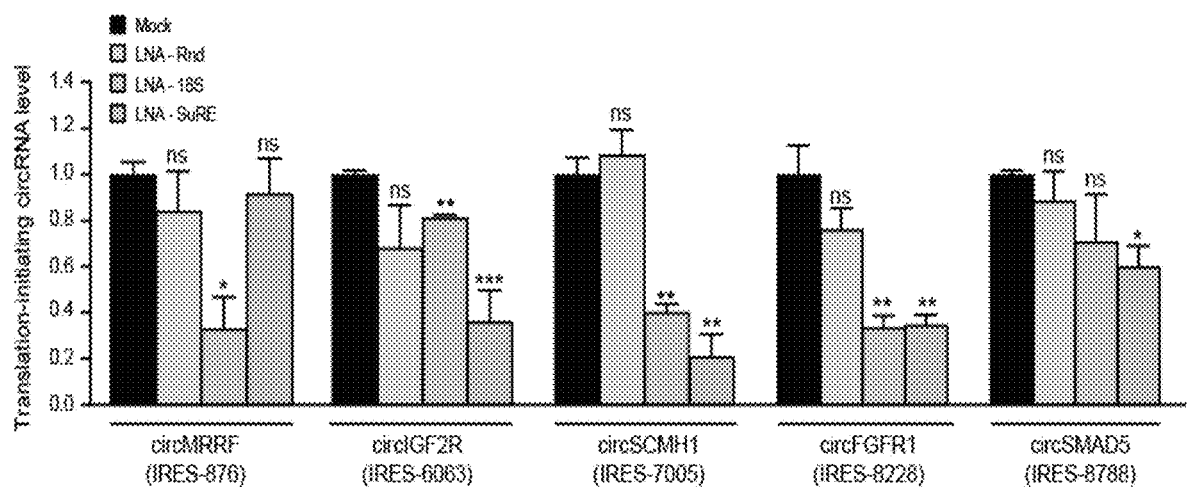
Figure 5E:
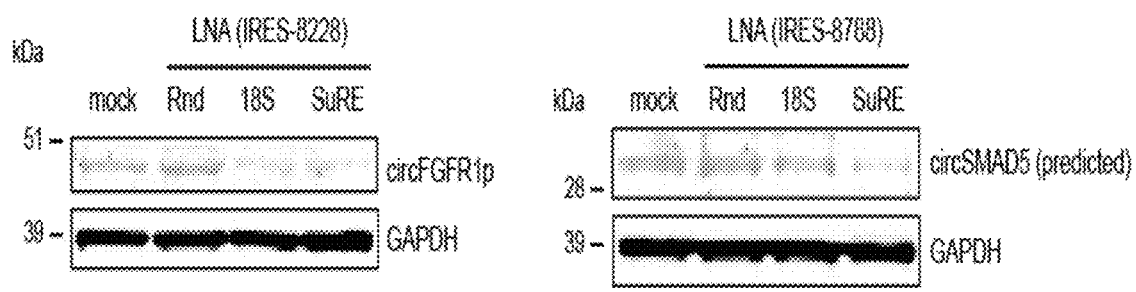
Figure 15B:
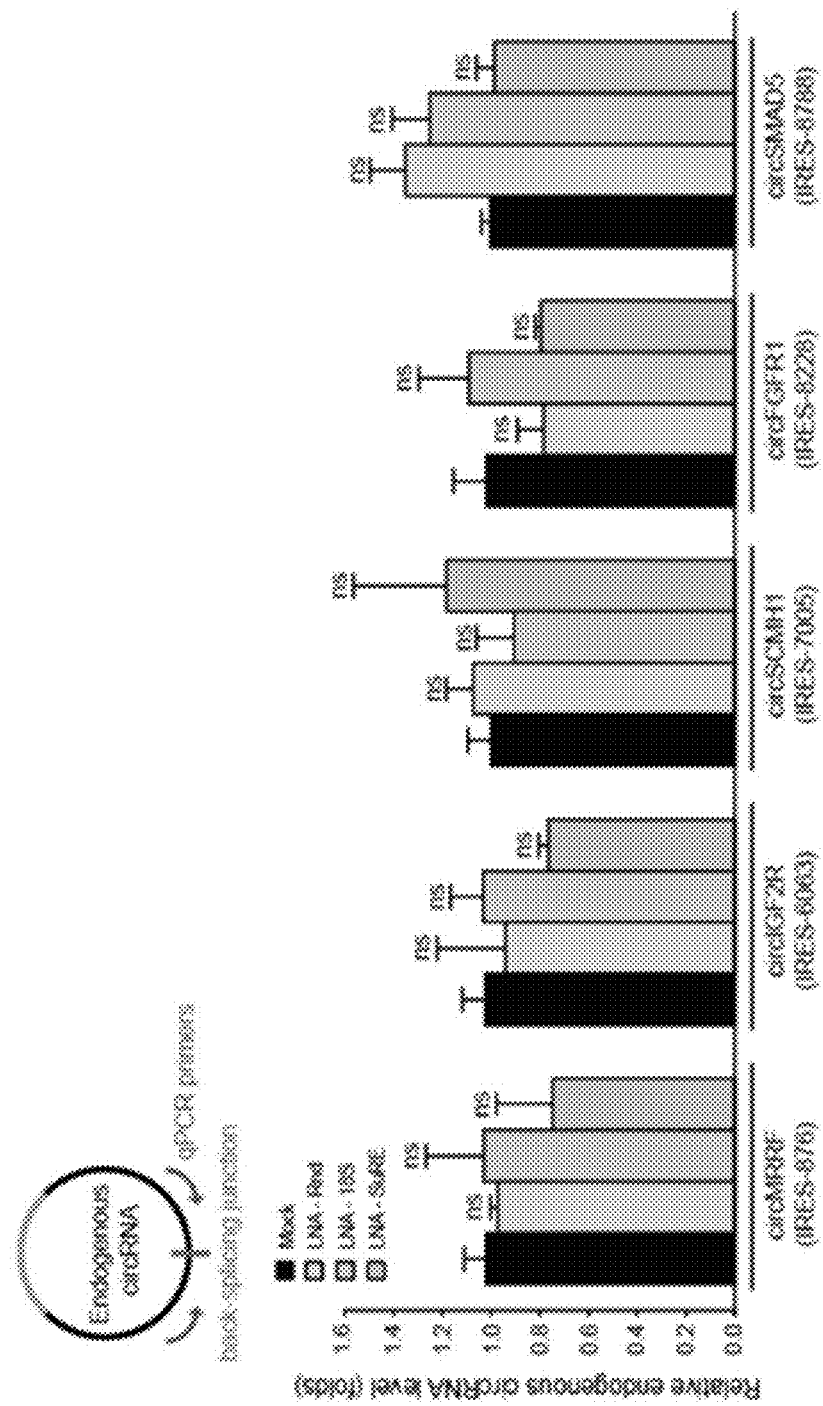

To further examine if the identified key regulatory elements on the IRES can also facilitate translation of human endogenous circRNAs, the cells were transfected with the corresponding anti-sense LNA and quantified translating circRNAs by the QTI method. Specifically, to isolate translating RNAs, LNA-transfected cells were treated with lactimidomycin (LTM) followed by puromycin (PMY) treatment, ribosome-associated RNAs were sedimented with sucrose cushion, and the translating RNAs were purified (FIG. 5C). The level of translating endogenous circRNA was then quantified, which contains the LNA-targeted IRES by qRT-PCR using the divergent primers spanning across the back-splicing junction of the circRNA. It was found that disrupting the key regulatory elements by LNA-18S or LNA-SuRE on the IRES of the endogenous circRNA can in general cause decreased translation activity of the circRNAs (8 out of 10 LNAs), while all the LNA-Rnd did not influence the translation activity of the endogenous circRNAs (5 out of 5 LNAs) (FIG. 5D). It was also confirmed that the LNA transfection did not change the expression level of the endogenous circRNAs (FIG. 15B). Since QTI method specifically captured the RNAs that are at the initiation stage of translation, it suggested that the decrease of endogenous circRNA translation observed upon LNA transfection came from the decrease in translation initiation. The results were further validated by quantifying the protein level produced from the endogenous circRNAs by Western blotting. The Western blotting result matched what was observed in the QTI-qRT-PCR result—disrupting the key regulatory elements on the IRES of the endogenous circRNA generally reduces the protein level produced from the circRNA (3 out of 4 LNAs) (FIG. 5E). The results above suggest that the key elements identified on the IRES, such as the 18S rRNA complementary sequence and the SuRE at the 40-60 nt position, are important for facilitating translation initiation of endogenous circRNAs.

Example 7

Figure 6A:
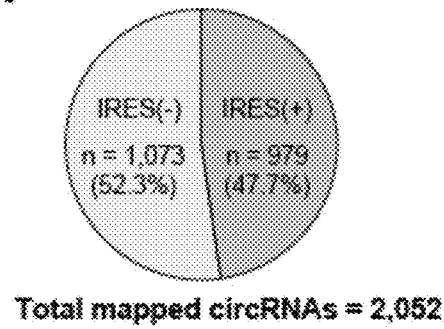
FIG. 6A-6L demonstrate the identification of putative endogenous circRNA-encoded proteins.
Figure 6B:
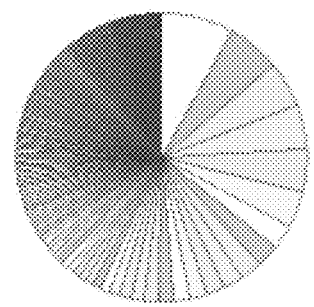
Figure 6C:
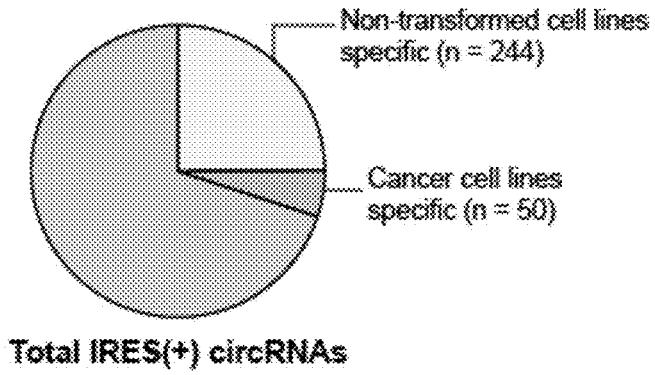
Figure 16A:
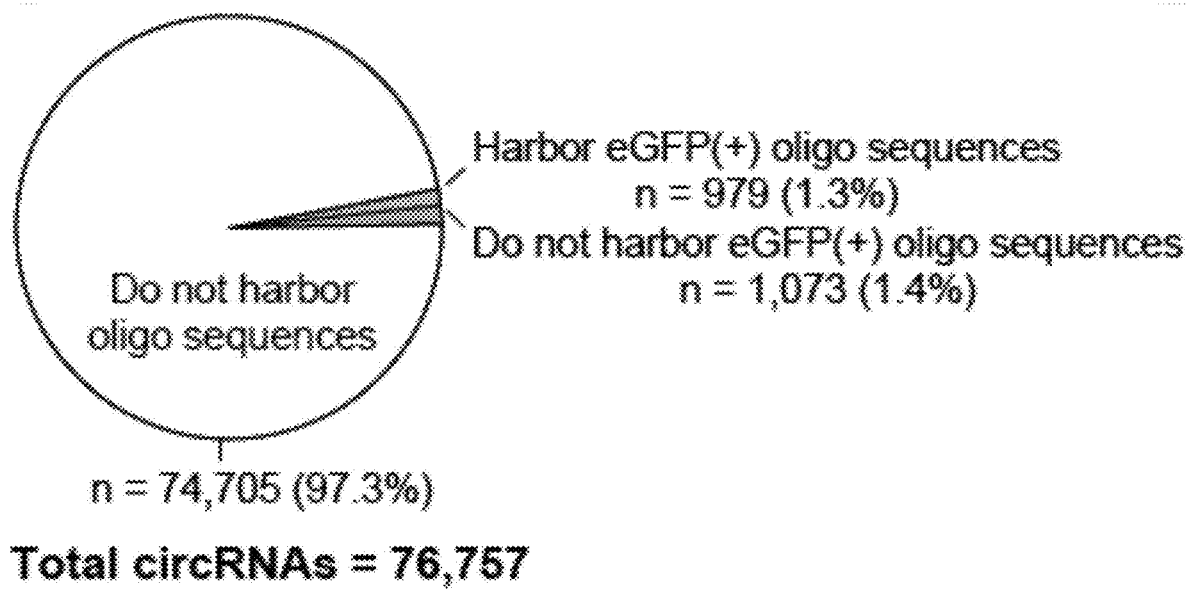

This example describes the identification of possible endogenous protein-coding circRNAs. Introducing synthetic IRES on circRNAs is sufficient to initiate cap-independent translation, suggesting that endogenous circRNAs harboring the active circular IRES may have the potential of producing proteins with cap-independent translation. Thus, to determine the potential circRNA proteome, the eGFP(+) oligo sequences captured in the screens to the human circRNA database (circBase) (Glazar et al., RNA 20, 1666-1670 (2014)) to identify the endogenous circRNAs which harbor the active IRES. Data was gated against false positive by only considering circRNAs that have been annotated by two different circRNA prediction algorithms, and only including circRNAs with high mapping score in this analysis. The result suggested a high proportion of the endogenous circRNAs are potentially protein-coding: Out of 2,052 endogenous circRNAs containing the oligo sequences from the synthetic library used for the screening assay, 979 circRNAs (~48%) contain one or more eGFP(+) oligo sequences (IRES(+) circRNAs) (FIG. 6A, FIG. 16A, Table 6). These circRNAs were generated from various parent genes which showed a fairly homogenous distribution across the genome (Gini index=0.38) (FIG. 6B). To further determine if these IRES(+) circRNAs are associated with cancer progression, the cancer-specific circRNA database (CSCD) (Xia et al., Nucleic Acids Res 46, D925-D929 (2018)) was examined, which contains the collection of potential cancer-associated circRNAs by analyzing the RNA-seq data of 228 cancer and normal cell lines. Interestingly, it was discovered that 294 of 979 IRES(+) circRNAs (~30%) are expressed specifically in either non-transformed cell lines (n=141 cell lines) or cancer cell lines (n=87 cell lines across 19 cancer types), respectively (FIG. 6C), indicating their potential association with cancer progression.

Figure 6D:
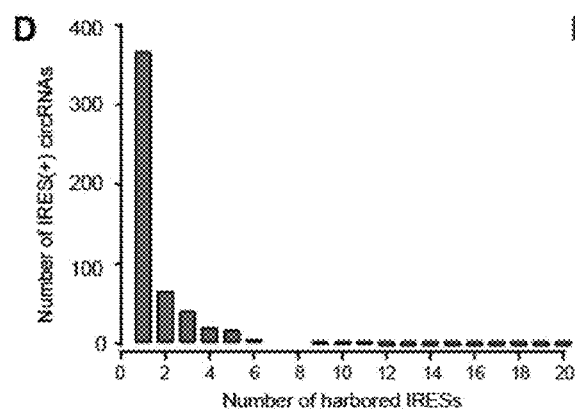
Figure 6E:
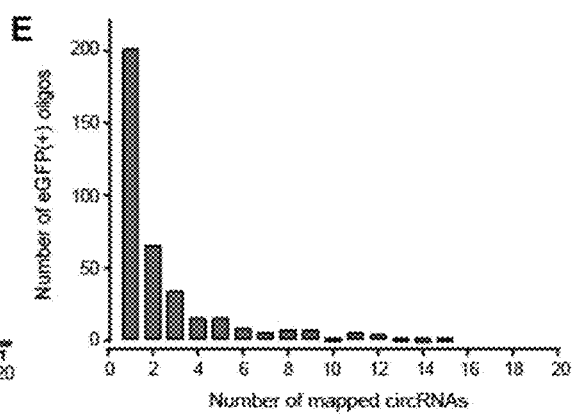
Figure 6F:
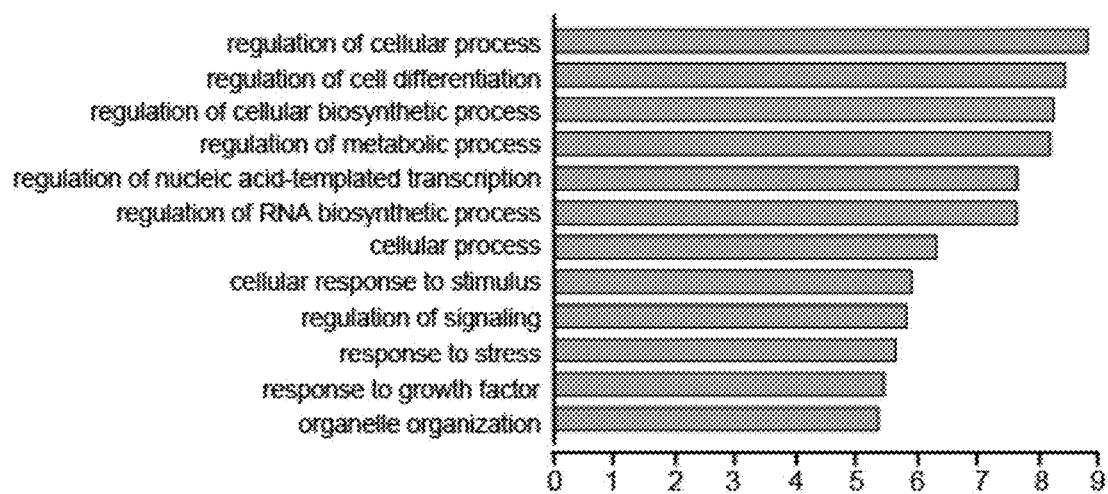
Figure 16B:
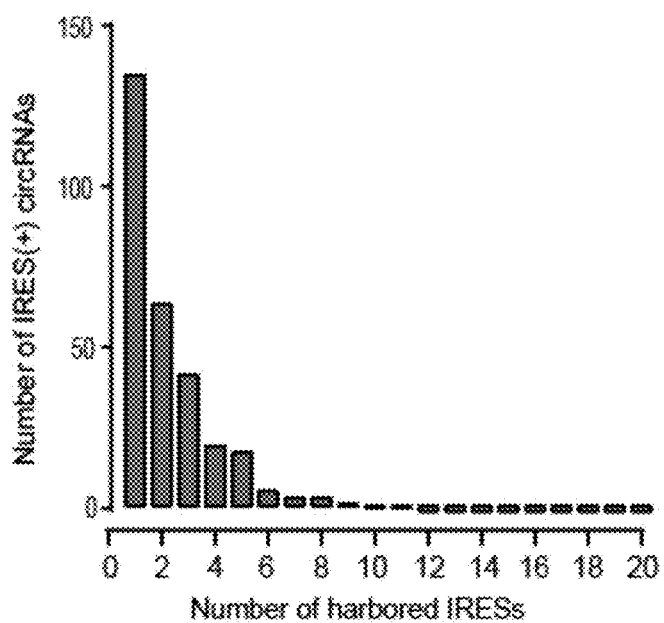
Figure 16C:
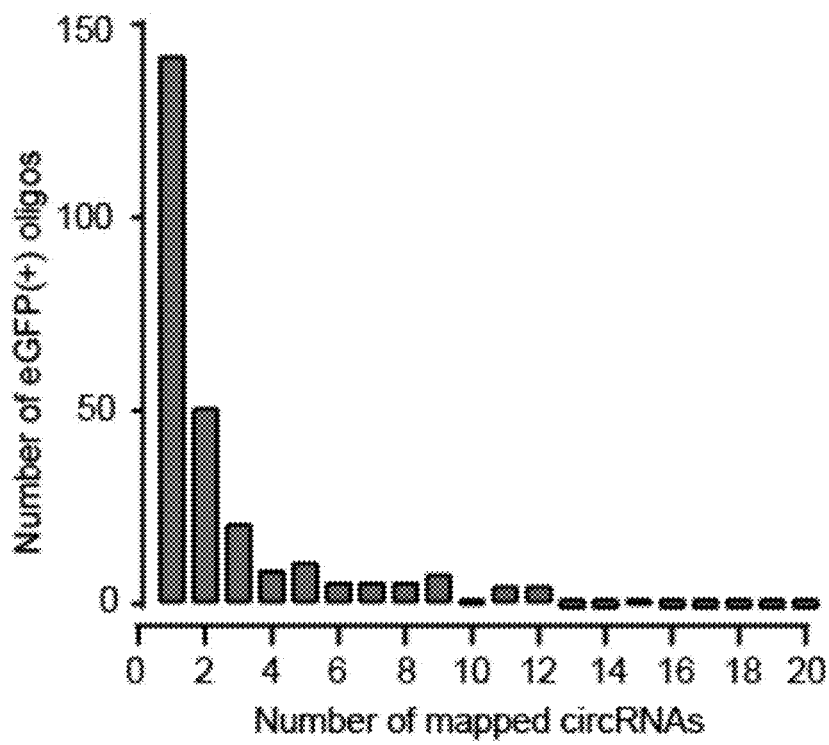
Figure 16D:
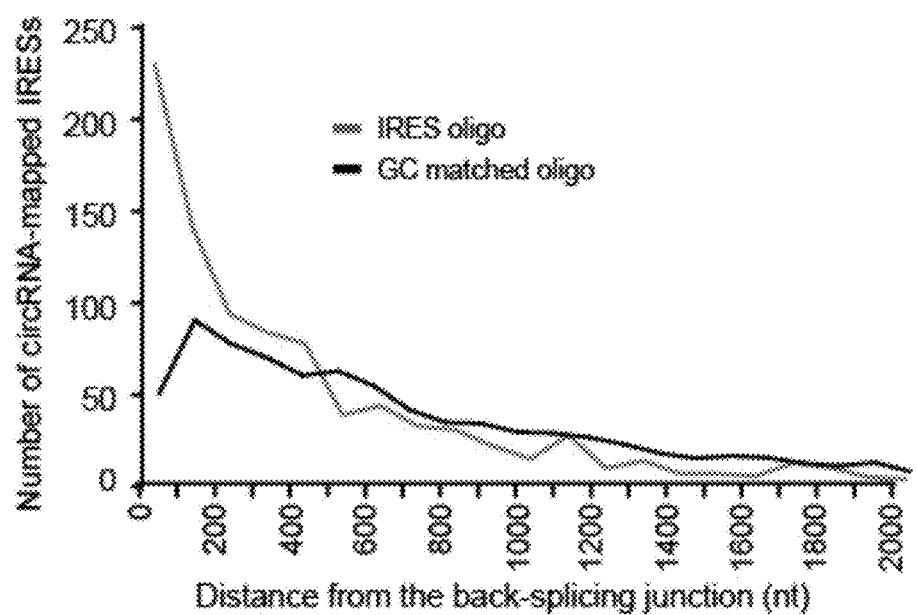

It was discovered that most IRES(+) circRNAs contain only one IRES (FIG. 6D) and most eGFP(+) oligos map to only one circRNA (FIG. 6E), suggesting a specific one-to-one relationship between these IRES(+) circRNAs and the proteins encoded by them. This result is expected in part based on the library design. In addition, for 159 transcripts for which oligos tiling across the entire transcripts were designed, a preponderance of one IRES per circRNA was observed (FIGS. 16B and 16C). Thus, circRNA IRES would have been difficult, if impossible, to discover by comparative sequence analysis across circRNAs, but can be discovered by unbiased functional screening. The result also suggests that circRNA IRES activity may require long RNA sequences which are more likely to show up once per transcript, rather than very short or repetitive sequences that would show up multiple times per transcript. Furthermore, it was discovered that the position of mapped eGFP(+) oligos on circRNAs is most frequently near the back-splicing junction of the circRNA (within 100-200 nt from the junction), while the average position of GC-matched oligos (the 174 nt oligos on the IRES-mapped circRNA with the same GC content as the mapped eGFP(+) oligo) showed a random distribution across a wide range of distance from the back-splicing junction on the circRNAs (100 to 2000 nt from the junction) (FIG. 16D). This result suggests that the cap-independent translation activity of the IRES on the circRNA is back-splicing dependent—the IRES element or its downstream open reading frame (ORF) is only assembled upon back-splicing. This requires the IRES to be located in the proximity of the junction to facilitate its cap-independent translation activity. Finally, gene ontology (GO) analysis of the parent genes of these circRNAs suggested that they are enriched in stress-response and translation regulation (FIG. 6F). Above all, these results demonstrated that with the identified eGFP(+) oligo sequences, it is possible to determine endogenous circRNAs with potential cap-independent translation activity that may encode new protein isoforms.

Example 8

This example describes the identification of potential endogenous circRNA-encoded polypeptides.

Figure 6G:
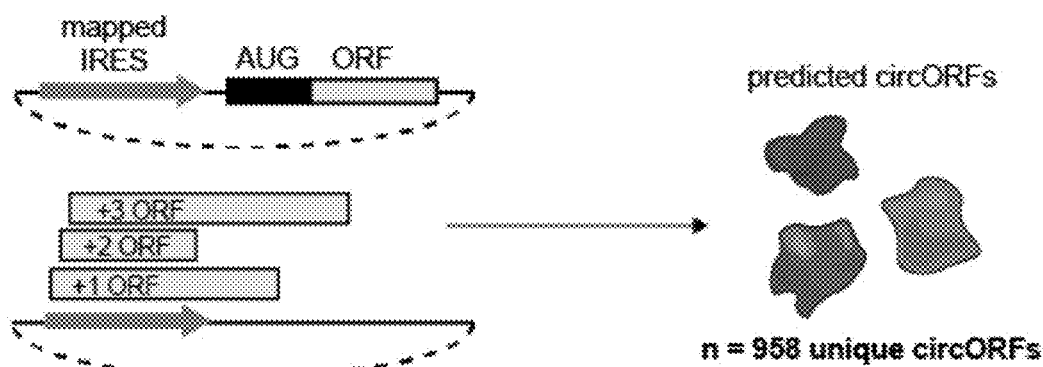

In order to determine the polypeptide sequence of proteins encoded by RNA, protein-coding sequence on the RNA were defined. This is commonly achieved by ORF analysis. However, ORF analysis on circRNAs often returns a large number of results due to the lack of information of where translation initiates on the circRNA. The data presented herein can map the position of eGFP(+) oligo sequences on the circRNA, which allows for determination of the regions on circRNAs where the translation start sites may be located. Thus, to determine the potential polypeptide sequence of the proteins encoded by the endogenous circRNAs, the eGFP(+) oligo sequences were mapped to the sequence of each individual high-confident circRNA in the circBase (pre-gated the high confident circRNAs as described above) to determine the location of the IRES on each circRNA (FIG. 6G). Predicted polypeptide sequences of the protein(s) encoded by each circRNA were then generated by performing ORF analysis from the immediate downstream translation initiation codon (AUG) of the mapped IRES location (FIG. 6G). Because many IRES have been reported to be able to initiate translation from non-canonical initiation codons, ORF analysis was also performed on the top three frames (+1 to +3) with non-canonical initiation codons from the mapped IRES position (FIG. 6G). With this method, a list of predicted polypeptide sequences encoded by human endogenous circRNAs (circORFs) was generated. To be conservative, micropeptides encoded by linear RNAs were also examined and any overlapped circORFs were excluded in the final list (n=5 overlapped circORFs). The final list contains 958 potential circORFs encoded by endogenous circRNAs (FIG. 6G, SEQ ID NO: 32954,-33911, Tables 7A and 7B).

Figure 16G:
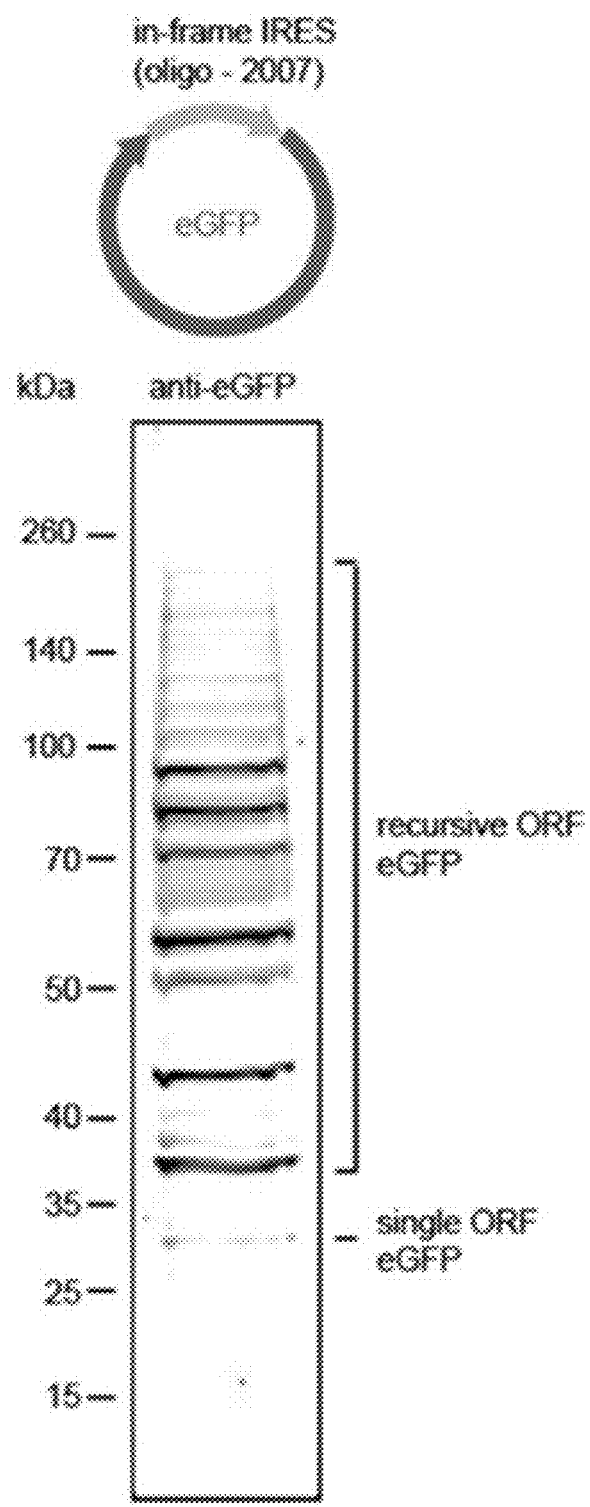

By analyzing the circORF sequences and mapped IRES position on the circRNAs, it was discovered that some circRNAs contain the IRES sequence overlapping the translated region of the ORF (n=457; ~48%) (FIG. 16E). The IRES-overlapping ORF has been observed in some endogenous circRNA-encoded proteins, which suggests some regulatory mechanisms may exist between the initiation and the elongation of circRNA translation. Interestingly, among these circRNAs with IRES-overlapping ORFs, some of them contain in-frame ORFs without stop codons (n=82; ~18%), forming recursive ORFs which may be the mechanism of amplifying the expression level of the circRNA-encoded proteins (FIG. 16F). It was further demonstrated that the in-frame IRES can indeed produce recursive ORF on the eGFP circRNA reporter (FIG. 16G).

Figure 6H:
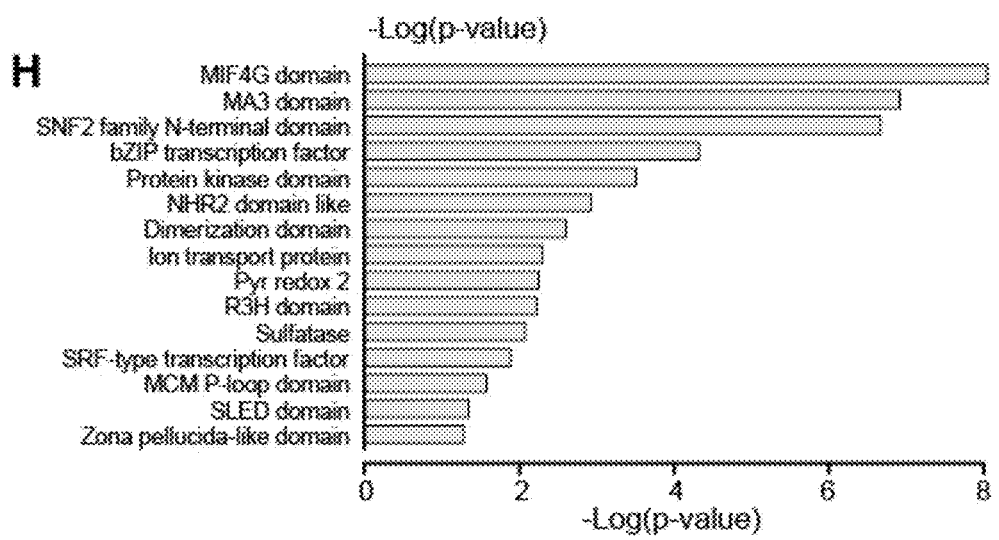
Figure 16H:
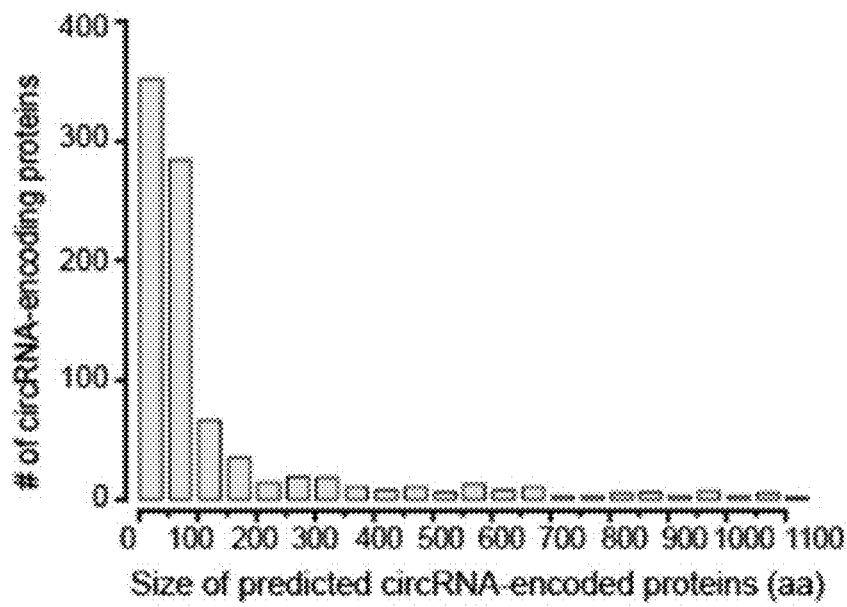

Next, it was the general functions of these potential circORFs were characterized by searching for conserved motifs on the predicted polypeptide sequences. Pfam analysis revealed that a substantial number of circORFs contain conserved motifs. The top motifs are DNA binding motifs, translation elongation factors binding motifs, protein kinase domains, and protein dimerization domains (FIG. 6H), suggesting that circORFs may play roles in regulating various biological functions including signal transduction, transcription, and translation. The size of most of these potential circORFs was small (<100 amino acids) (FIG. 16H), which suggests that the majority of them may be the truncated forms of the proteins generated from their parent linear transcripts.

Figure 16I:
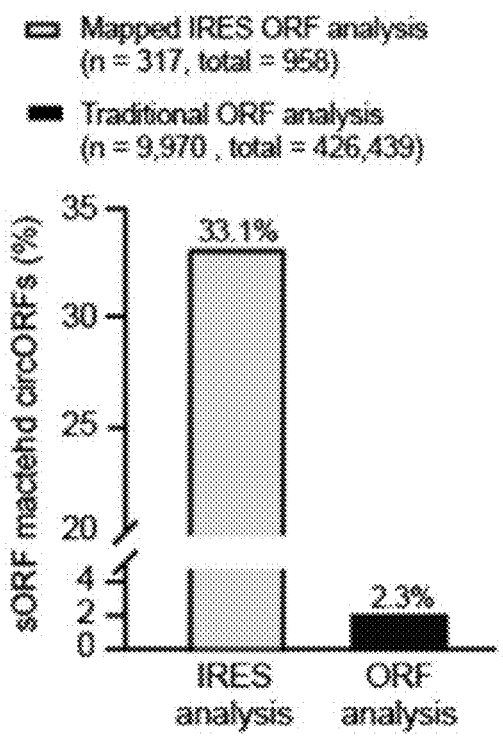

To further validate the potential circORFs, the short open reading frame (sORFs) database was examined (Olexiouk et al., Nucleic acids research 46, D497-D502 (2017)), which contains the polypeptide sequences (<100 amino acids) from the identified sORFs aggregated by multiple ribosome profiling studies, to checked if the polypeptide sequences of these sORFs can match the circORFs. The sORFs were first mapped to the current proteome database (UniProt) and those sORFs that completely matched the ORFs of the annotated linear transcripts were excluded. The remaining sORFs were then mapped to the potential circORFs. 317 predicted circORFs were identified, which can be matched by the sORFs (~33%) (FIG. 16I), suggesting that the mapped IRES ORF analysis method can identify endogenous circORF efficiently. On the other hand, traditional ORF analysis on the same circRNAs, which takes all possible translation initiation locations, gives a huge number of predicted polypeptides (n=426,439), where only a very small fraction of those polypeptides were captured by sORF studies (n=9,970; ~2%) (FIG. 16I). Thus, knowledge of the circRNA IRES led to an ~15-fold improvement in predicting circRNA derived sORFs. Together, the result suggests that in comparison to traditional ORF analysis, the mapped IRES ORF analysis is able to identify endogenous circORFs more efficiently.

Figure 6I:
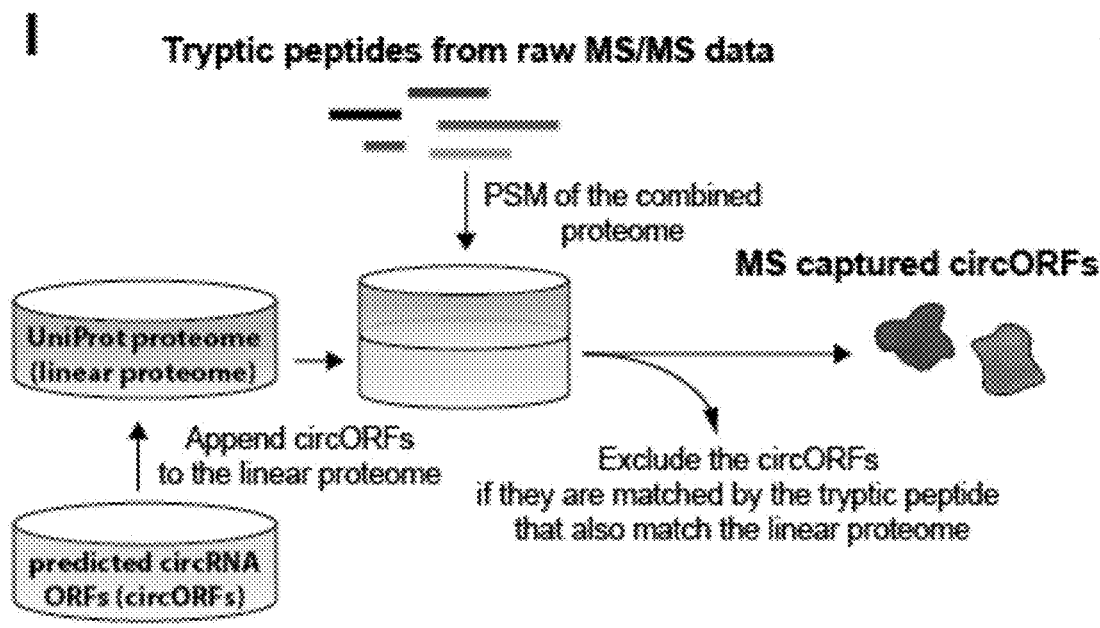
Figure 6J:
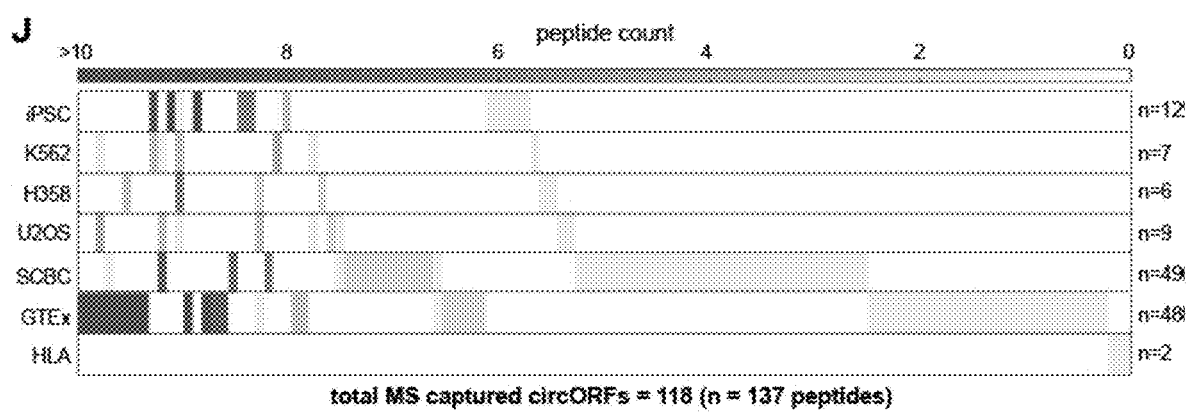
Figure 6K:
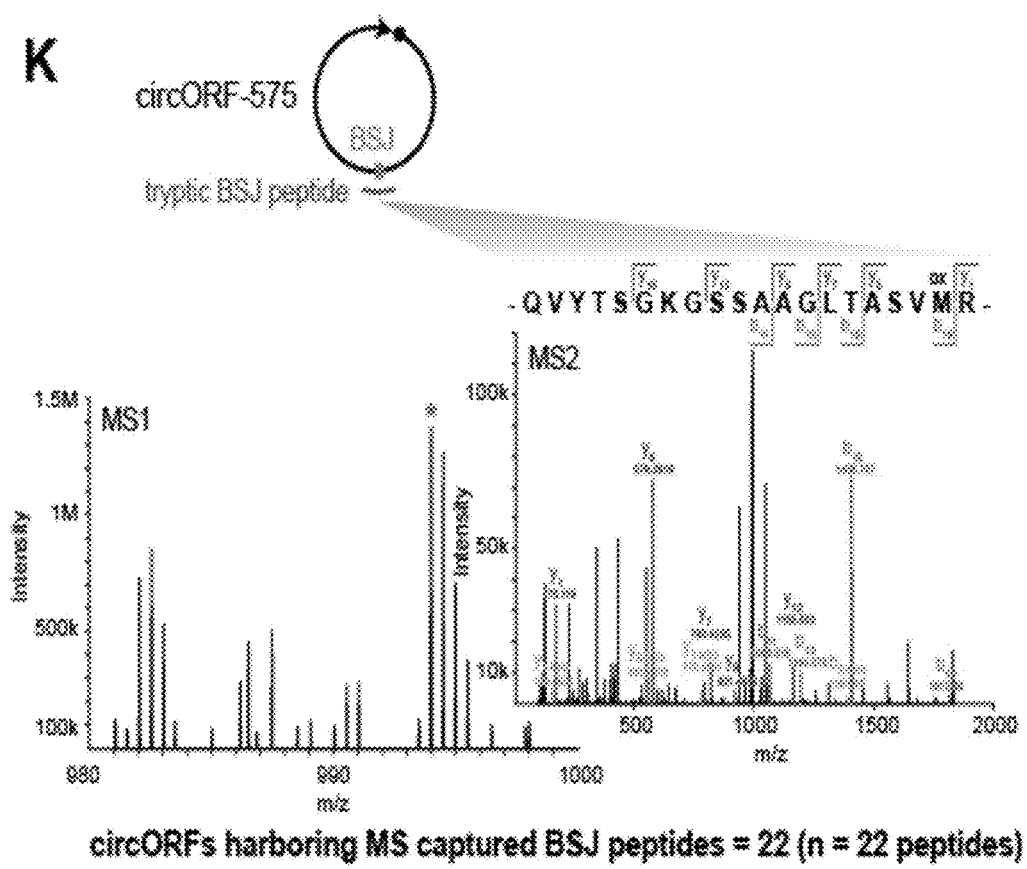
Figure 6L:
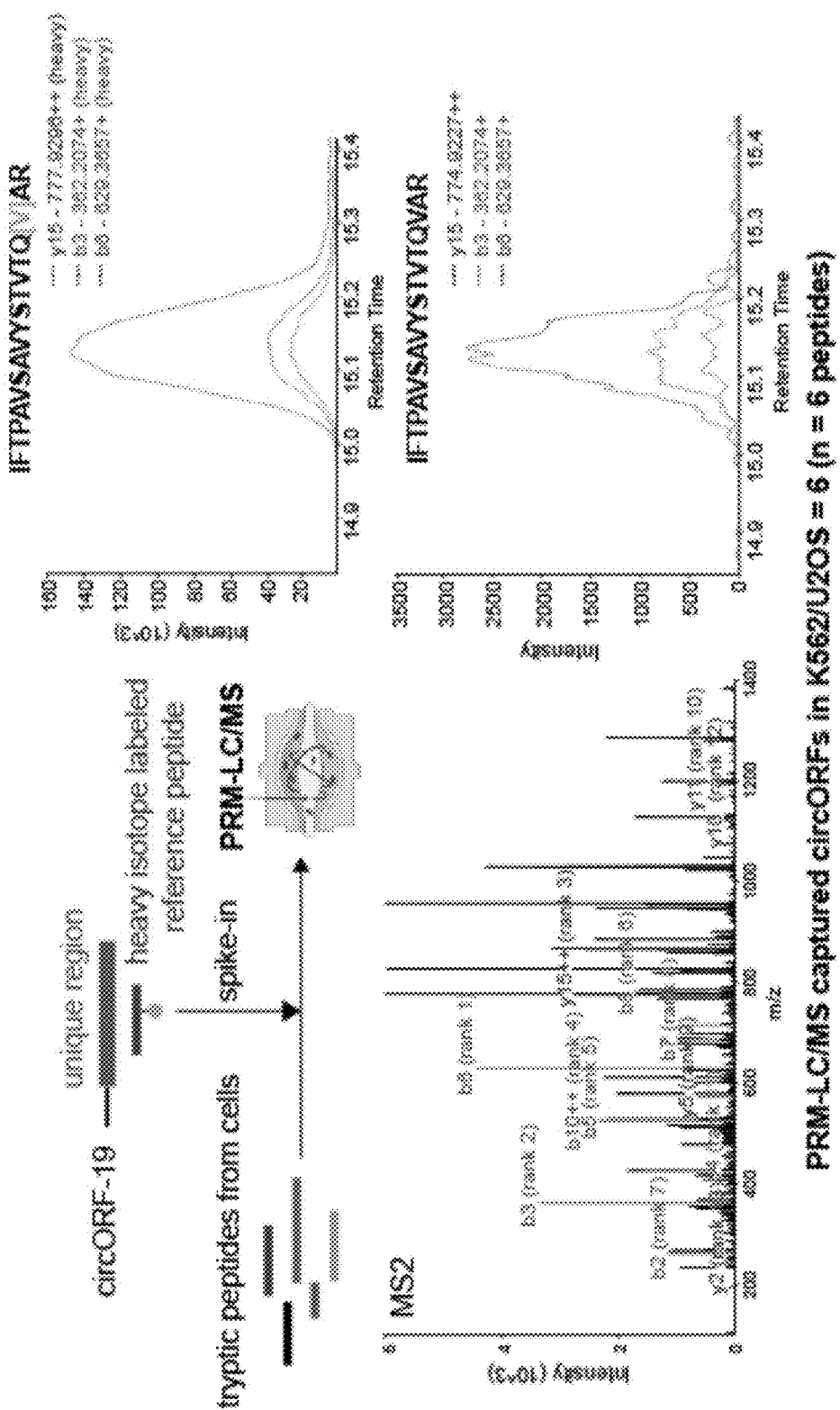
Figure 16J:
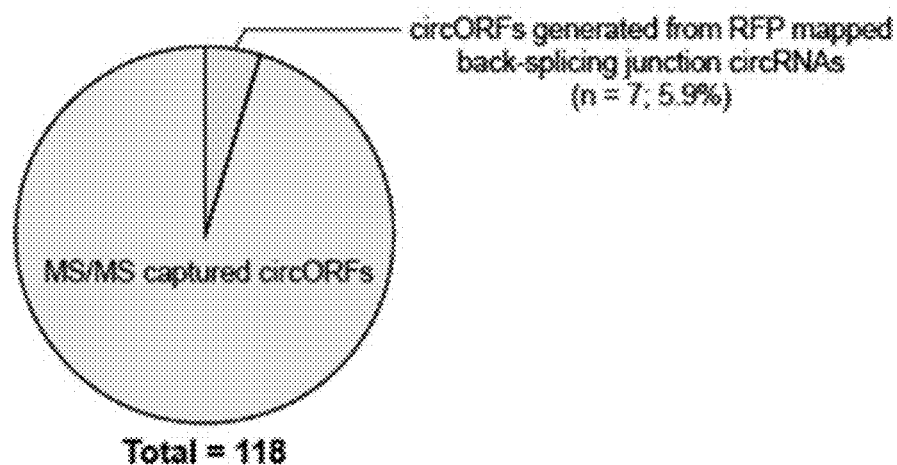

Subsequently, peptidomic analyses was performed on the tandem mass spectrometry (MS/MS) datasets to validate the endogenous expression of the circORFs. Specifically, the predicted circORF list was appended to the current proteome database (UniProt; linear proteome) and generated a combined proteome database (circORFs+linear proteome). The raw MS/MS data was then taken from a wide range of cell lines, including K562, H358, U20S, subcellular compartments SubCellBarCode (SCBC) database, and 32 normal human tissues from the GTEx collection and performed peptide-spectrum match (PSM) against the combined proteome database (FIG. 6I). To distinguish circORFs from the linear proteome, the circORFs were excluded if the circORFs are matched by the tryptic polypeptides that can also match the linear proteome (FIG. 6I). 118 circORFs harboring MS-matched unique tryptic polypeptides (FIG. 6J) were captured, in which 22 circORFs harboring MS-matched tryptic polypeptides spanning across the circRNA back-splicing junction (BSJ) (FIG. 6K). In addition to the transformed cell lines, circORFs in the peptidomics of normal human tissues were captured (Jiang et al., 2020), suggesting that these circORFs are expressed in normal human cells. Moreover, parallel reaction monitoring-MS (PRM-MS) was performed to provide high resolution validation of the circORF expression in K562 and U20S. Specifically, the heavy isotope-labeled reference polypeptides of the unique region of the circORFs identified from the K562 and U20S MS/MS peptidomics were designed and synthesized, the labeled reference polypeptides were spiked in to the tryptic polypeptide samples, and precursor and transition ions detection was performed according to the labeled reference polypeptides (FIG. 6L, SEQ ID NO: 32954-33911, and Tables 7A and 7B). The PRM-MS further validates the existence of 6 out of 8 targeted circORFs (FIG. 6L, SEQ ID NO: 32954-33911, and Tables 7A and 7B). The MS/MS and the PRM-MS peptidomics provide strong evidence demonstrating the circORFs are indeed expressed endogenously. As a complementary approach, the ribosome footprinting (RFP) data was examined in human iPSCs (Chen et al., Science (2020) 367(6482):1140-1146), and it was found that 7 MS/MS detected circORFs contain at least one RFP fragment overlapping uniquely with the circRNA back-splicing junction (FIG. 16J). Together, these results suggest that it is possible to build a putative circORF list using the circRNA IRES screening assay which can be validated by genomic and peptidomic analyses.

To further examine if the circORFs are involved in antigen presentation, the human leukocyte antigen I (HLA1)-associated peptidomics was analyzed (Bassani-Sternberg et al., 2015). Two HLA1-associated circORFs were identified (FIG. 6J). In silico HLA1 binding predictor NetMHC4.1 analysis (Reynisson et al., 2020) suggests that these two circORFs are indeed strong HLA1 binder to the HLA1 variants expressed in the cell line used in HLA1 peptidomics (HLA-A03:01 for circORF_674 in fibroblast; HLA-C07:02 for circORF_917 in JY) (Tables 7A and 7B). The result indicates a new functional role of circORFs that some of the circORFs may enter the HLA-I presentation pathway and contribute to the antigen repertoire.

Figure 16K:
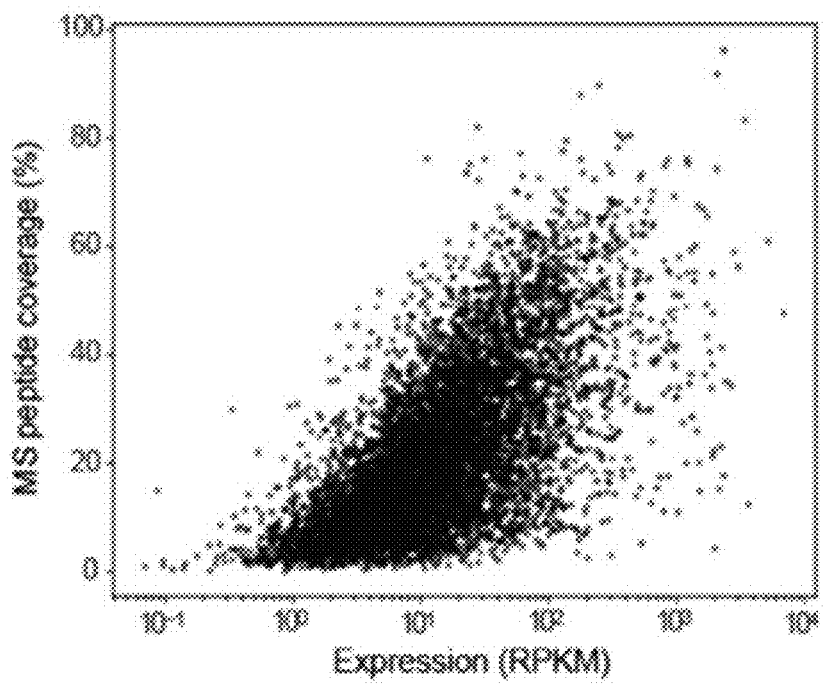
Figure 16L:
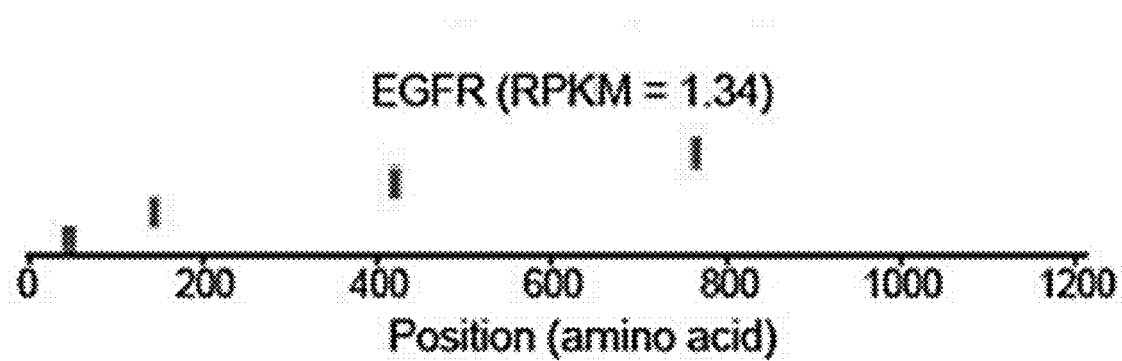

Notably, circORF detection by MS-based peptidomics is limited by (i) insufficient power to capture low abundance circORFs arising from low circRNA expression level in general, (ii) potential instability of circRNA-encoded polypeptides, (iii) the intrinsic difficulties to detect generally short circORFs, (iv) the number of cell lines/types of peptidomic datasets available, and (v) the narrow reference space of circORF unique polypeptides since all the regions that are shared by circORF and the linear proteome were excluded. Given the limitations of circORF peptidomics, identification of circORFs was interpreted as positive validation; the absence of detection in MS proteomic data does not rule out the translational potential for circRNA candidates. In line with the limitations above, when the same limitations were applied to proteins encoded by known mRNAs, matching for expression level and the cell line examined, and down-sampled reference space, it was found that current peptidomic data can only recover ~5% polypeptides of the protein encoded by the mRNA with the same RPKM as the mean circRNA RPKM (FIGS. 16K and 16L). Moreover, the expected discovery rate of circORFs is estimated to be ~4% since, since only the circORF unique regions are searched. The fact that it is possible to validate ~12.3% (118 out of 958) circORFs with peptidomics, which is much higher than the expected discovery rate for circORFs, further highlights that the approach disclosed herein can efficiently identify candidate endogenous circORFs, and supports the contention that circRNAs widely encode polypeptides similar to moderately expressed mRNAs.

Example 9

This example demonstrates that circFGFR1p suppresses cell proliferation under stress conditions through a dominant-negative regulation.

To evaluate the potential functions of the expanded circRNA proteome, an example of a potential protein-coding circRNA, hsa_circ_0084007, was chosen, and the function of its encoded protein was further examined. The circRNA is generated from the back-splicing of the exon 2 and the exon 7 of the human Fibroblast Growth Factor Receptor 1 (FGFR1) transcript; hence the names circFGFR1 and circFGFR1p were used to refer to this circRNA and its encoded protein, respectively. Down-regulation of circFGFR1 has been observed in clinical cancer patient samples, which may suggest its role in regulating important biological processes. CircFGFR1 harbors an IRES showing strong eGFP expression in the screening assay (top 2%), located in the 5' UTR region of FGFR1 followed immediately by an annotated AUG translation start codon (FIG. 7A). ORF analysis using the immediate downstream AUG revealed that the back-splicing generates a de novo stop codon within the IRES of circFGFR1, resulting in an ORF that partially overlaps with the IRES (circORF_949) (FIG. 7A). To better characterize the phenotype and the function regulated by circFGFR1, a non-transformed human cell line, BJ fibroblasts, was utilized for subsequent analysis. This cell line has a diploid genome for better phenotypic analysis and high FGFR1 expression. First, it was checked whether circFGFR1 expression can be detected in BJ cell by reverse transcriptase PCR (RT-PCR) and Sanger sequencing using the divergent primers flanking the back-splicing junction of the exon 2 and the exon 7 on circFGFR1 (FIG. 7B). The results demonstrated that circFGFR1 expression in BJ cells can successfully be detected.

Figure 17A:
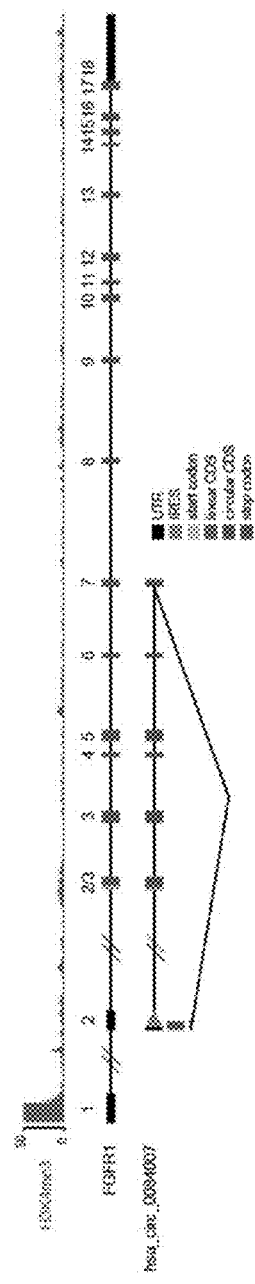
FIG. 17A-17I show that circRNA-encoded circFGFR1p suppresses cell growth under stress conditions.

Analysis of the predicted protein sequence indicated that circFGFR1p encodes a truncated form of FGFR1, which has an intact extracellular fibroblast growth factor 1 (FGF1) ligand-binding site, part of the dimerization domain (IgI, IgII, and partial N' terminus of IgIII) but lacks the intracellular FGFR1 tyrosine kinase domain (FIG. 7C). CircFGFR1p also harbor a unique region due to circFGFR1 back-splicing, where the polypeptide sequence of this region does not present in the linear proteome (UniProt) database (FIG. 7C). Western blotting using an antibody against the common region of circFGFR1p and FGFR1 (Ab-both) showed signals at the corresponding size of circFGFR1p (~38 kDa) and FGFR1 (70-90 kDa) (FIG. 7K). ENCODE data demonstrated an absence of chromatin signature of promoters (H3K4me3) near circFGFR1p IRES (FIG. 17A), suggesting the protein was not generated from the truncated linear transcript due to hidden promoters located in the exon 2 of FGFR1. In line with the observation above, the circFGFR1 IRES identified (oligo index: 8228) does not display promoter activity from the linear RNA IRES reporter screens (score=0) (Weingarten-Gabbay et al., 2016).

Figure 7D:
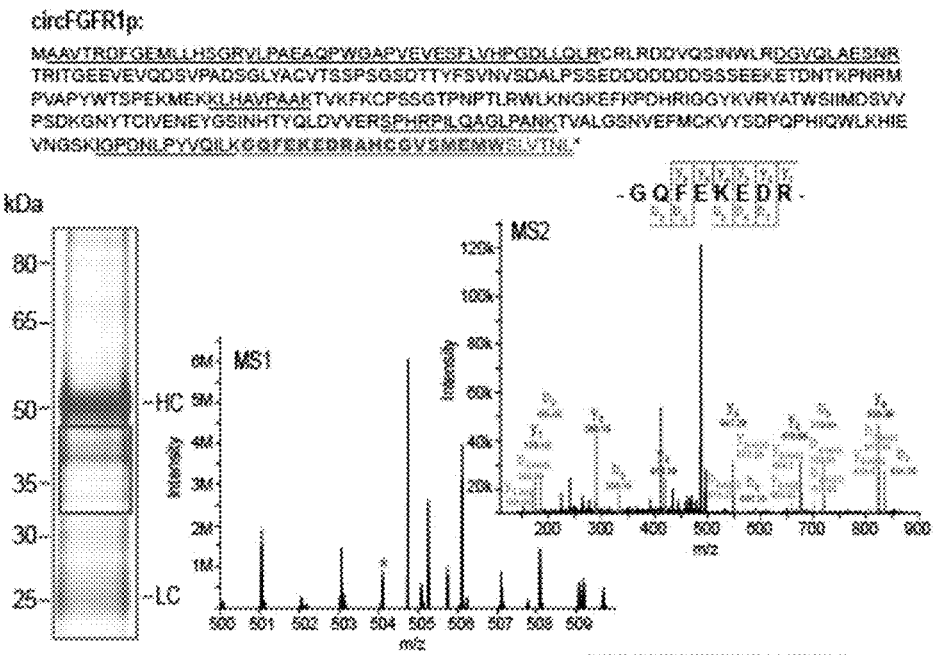
Figure 7E:
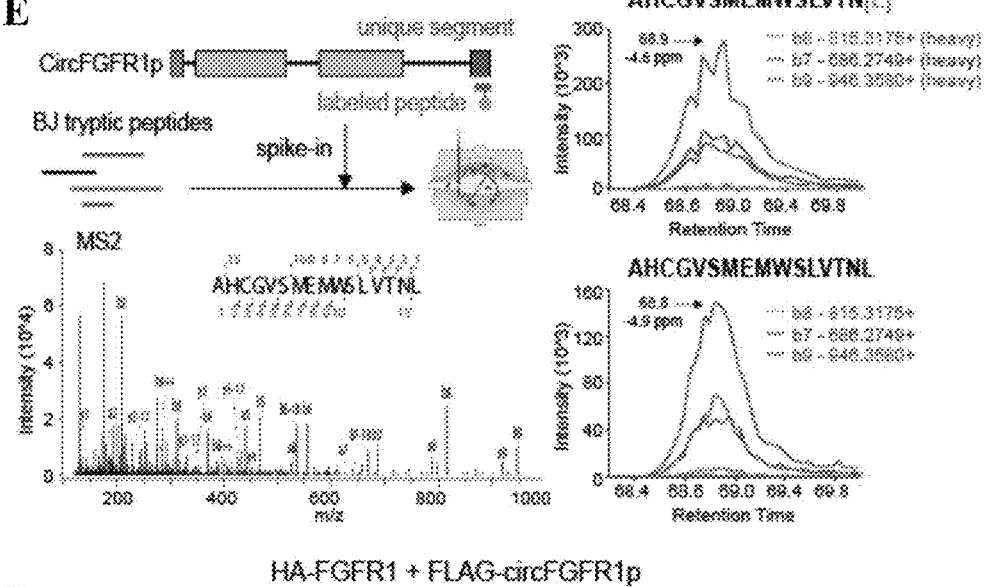

To validate endogenous circFGFR1p expression, a custom antibody against the unique region of circFGFR1p was generated. circFGFR1p was isolated by immunoprecipitation (IP) using the custom antibody, and proteins (size selected ~30-45 kDa on a polyacrylamide gel to separate circFGFR1p from FGFR1) were subjected to liquid chromatography with tandem mass spectrometry (LC-MS/MS) (FIG. 7D). While no circFGFR1p polypeptides were detected in the IgG control sample, it was possible to detect the tryptic polypeptides of the unique region of circFGFR1p as well as the tryptic polypeptides overlapped with the linear FGFR1 in the IP-LC-MS/MS sample (FIG. 7D). The result suggests that circFGFR1p is indeed expressed and can be captured by the circFGFR1p antibody. To further confirm circFGFR1p expression in high resolution, PRM-MS was performed using a synthetic heavy isotope-labeled reference polypeptide of the circFGFR1p unique region. It was possible to identify the corresponding precursor and transition ions of the labeled reference polypeptide and the sampling tryptic polypeptide from BJ cells, respectively (FIG. 7E). Collectively, the IP-MS and the PRM-MS provide the strong evidence demonstrating endogenous circFGFR1p expression.

Figure 7F:
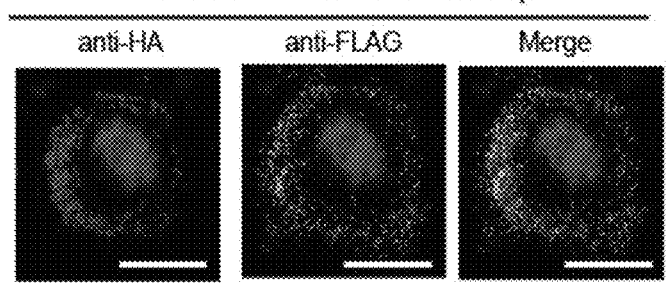
Figure 7J:
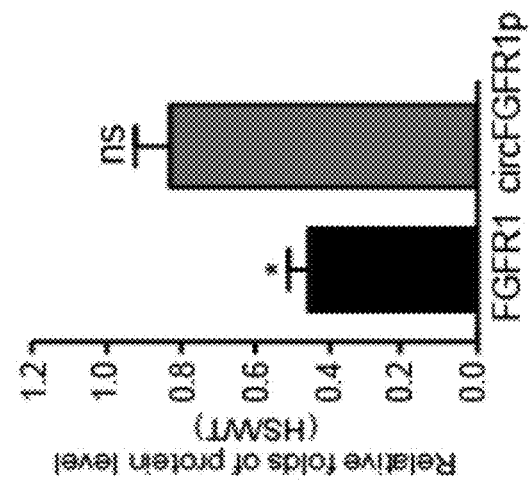
Figure 7K:
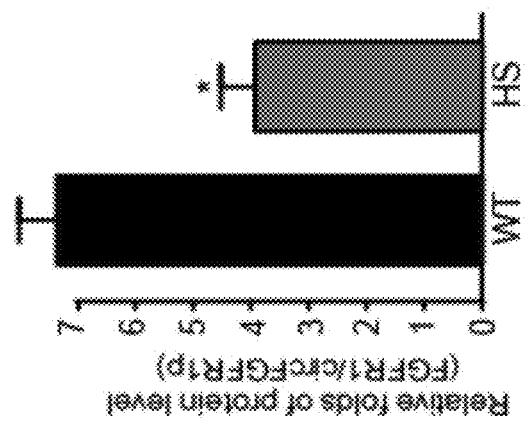
Figure 7L:
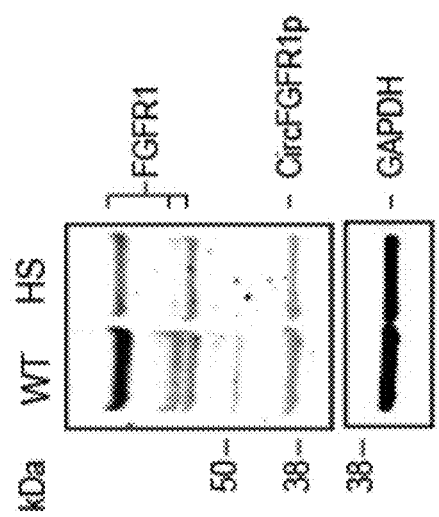
Figure 17B:
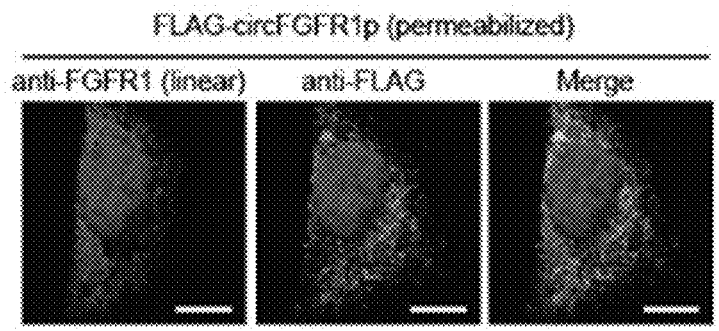
Figure 17C:
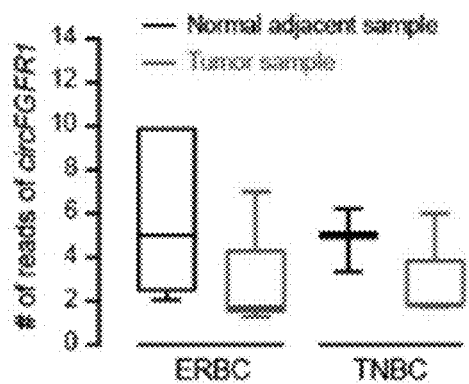
Figure 17D:
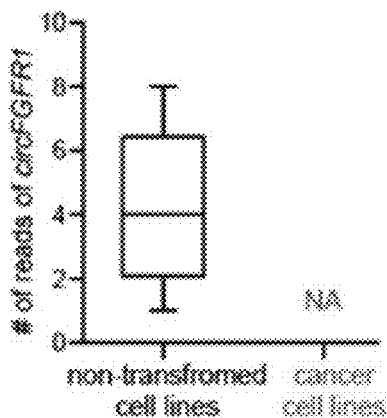

Upon binding to FGF, full-length FGFR1 dimerizes and autophosphorylates the kinase domain, which further triggers the downstream signaling pathway and facilitates cell proliferation. By co-expressing HA-tagged FGFR1 and FLAG-tagged circFGFR1p in HEK-293T cells and co-staining HA- and FLAG-tag to label FGFR1 and circFGFR1p respectively, it was confirmed that circFGFR1p is localized at the cell membrane in patchy domains and endosomes similarly to FGFR1 (FIG. 7F and FIG. 17B). CircFGFR1 contains the FGFR1 dimerization/ligand-binding domain but lacks the kinase domain, suggesting circFGFR1p may function as a dominant-negative regulator of FGFR1 that suppresses cell proliferation. Moreover, lower circFGFR1 expression level was found in the tumor samples of different subtypes of breast cancer in comparison to the normal adjacent samples from studies analyzing the RNA-sequencing data from The Cancer Genome Atlas (TCGA) (FIG. 17C). In addition, circFGFR1 expression was detected specifically in the non-transformed cell lines (n=5 unique non-transformed cell types out of 141 non-transformed cell line samples), but not in the cancer cell lines (n=87 cancer cell lines out of 87 cancer cell line samples) on the CSCD database (Xia et al., 2018) (FIG. 17D). These studies suggest that reduced circFGFR1 expression level may be associated with cancer progression by upregulating cell proliferation. Thus, circFGFR1p appears to function as a negative regulator of FGFR1 through a dominant-negative mechanism that suppresses cell proliferation.

To test this hypothesis, circFGFR1 was first knocked down specifically with siRNAs targeting the back-splicing junction of circFGFR1 (FIG. 7G). It was discovered that knockdown of circFGFR1 can indeed facilitate cell proliferation upon FGF addition (FIG. 7H), suggesting that circFGFR1 negatively regulates FGFR1 function of facilitating cell proliferation. To confirm that the cell proliferation phenotype that was observed resulted from the downregulation of circFGFR1p protein rather than circFGFR1 RNA, the cell proliferation phenotype was further examined upon downregulating circFGFR1p protein specifically by disrupting the cap-independent translation of circFGFR1p IRES. Since the translation initiation is typically the rate limiting step of translation, the anti-sense LNA targeting the 18S rRNA complementary sequence on the circFGFR1 IRES (LNA-18S of IRES-8228) was utilized, which was found to effectively blocks circFGFR1p translation initiation (FIGS. 5B and 5D), to knock down circFGFR1p specifically without altering the level of circFGFR1 or FGFR1 RNA (FIG. 7G). LNA-mediated inhibition of circFGFR1 IRES caused a lower expression level of circFGFR1p and a higher level of phosphorylated FGFR1 (FIG. 7G), suggesting that knocking down circFGFR1p, but not circFGFR1 RNA, can indeed lead to an increase in FGFR1 phosphorylation, leading to a higher level of active FGFR1 (phosphorylated FGFR1). It is also in line with the observation that knocking down circFGFR1p leads to a higher cell proliferation rate (FIG. 7H). Interestingly, the depletion of circFGFR1p also leads to a higher level of total FGFR1 protein (FIG. 7G). The result suggests that circFGFR1p functions not solely as a dominant-negative of FGFR1 signal transduction, but circFGF1p also somehow inhibits full-length FGFR1 accumulation, perhaps by increasing FGFR1 turnover or degradation. A similar FGFR1 degradation phenotype has also been observed when dominant-negative variants of FGFR1 are expressed in vivo. Conversely, it was checked if circFGFR1 overexpression in cells can suppress cell proliferation by encoding circFGFR1p with a FLAG epitope tag. Then, it was cloned it into a linear mRNA expression plasmid driven by CMV promoter to effectively overexpress circFGFR1p, and the circFGFR1p expression plasmid was transfected into BJ cells (FIG. 7I). The results demonstrated that circFGFR1p overexpression (circFGFR1pOE) can indeed suppress cell proliferation (FIG. 7I). In addition, when FGFR1 and circFGFR1p were co-overexpressed in cells (FGFR1OE+circFGFR1pOE), the phenotype of cell proliferation suspension was partially rescued (FIG. 7I), which further suggests the antagonistic function of circFGFR1p for FGFR1. These results suggest that circRNA-encoded circFGFR1p can suppress cell growth by interacting with FGFR1 through a dominant-negative mechanism.

Figure 17E:
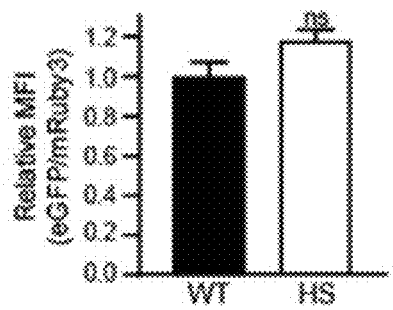
Figure 17F:
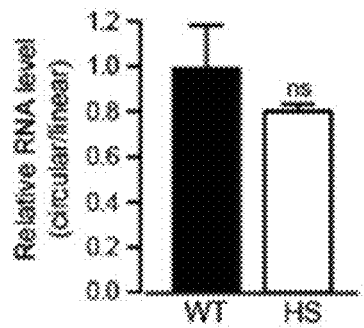
Figure 17G:
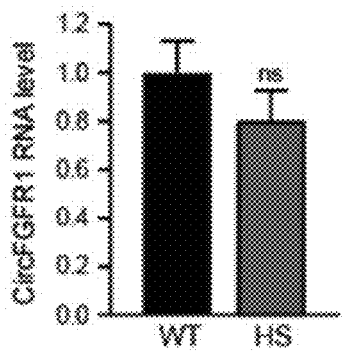
Figure 17H:
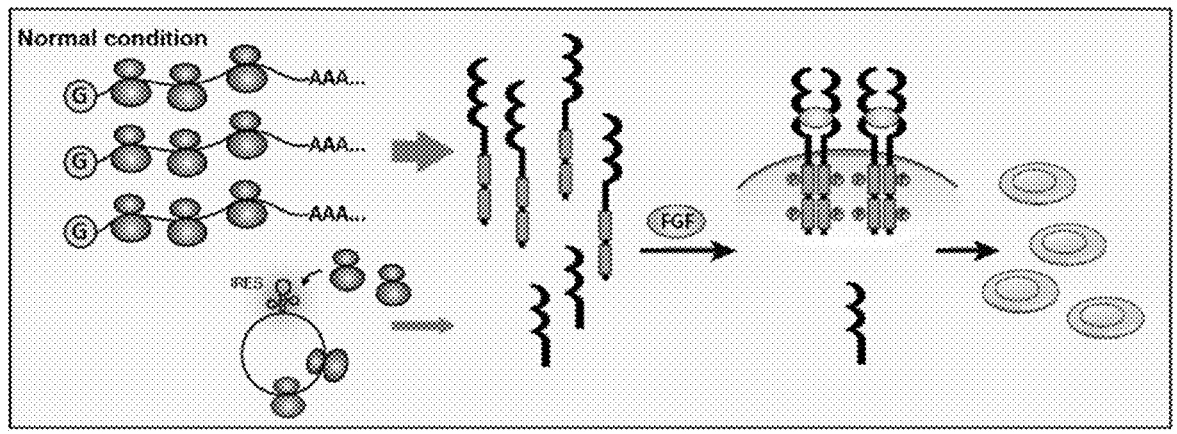
Figure 17I:
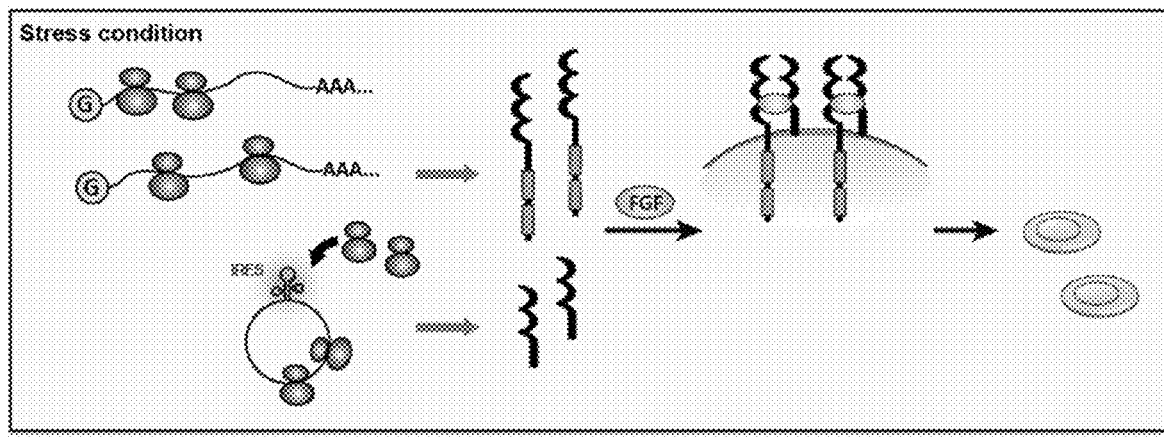
Figure 18A:
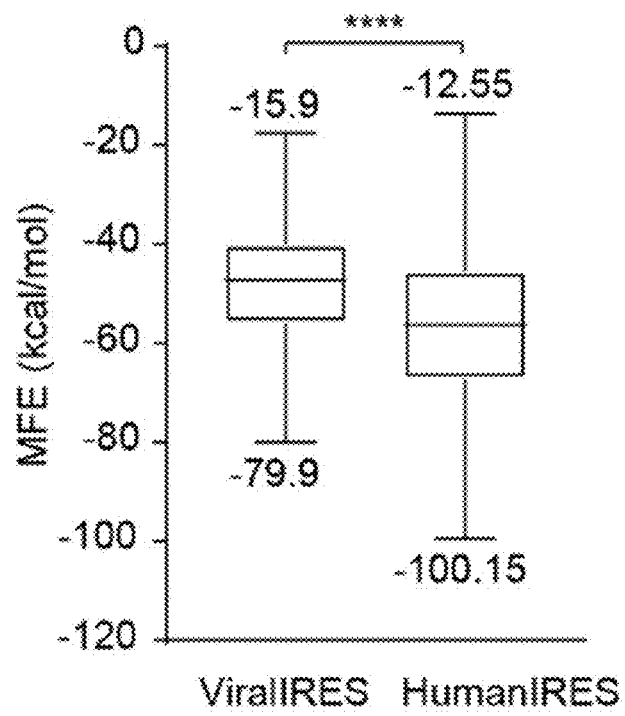
FIG. 18A-18B shows mean free energies (MFE) of various IRES identified and/or tested in the screen described herein.
Figure 18B:
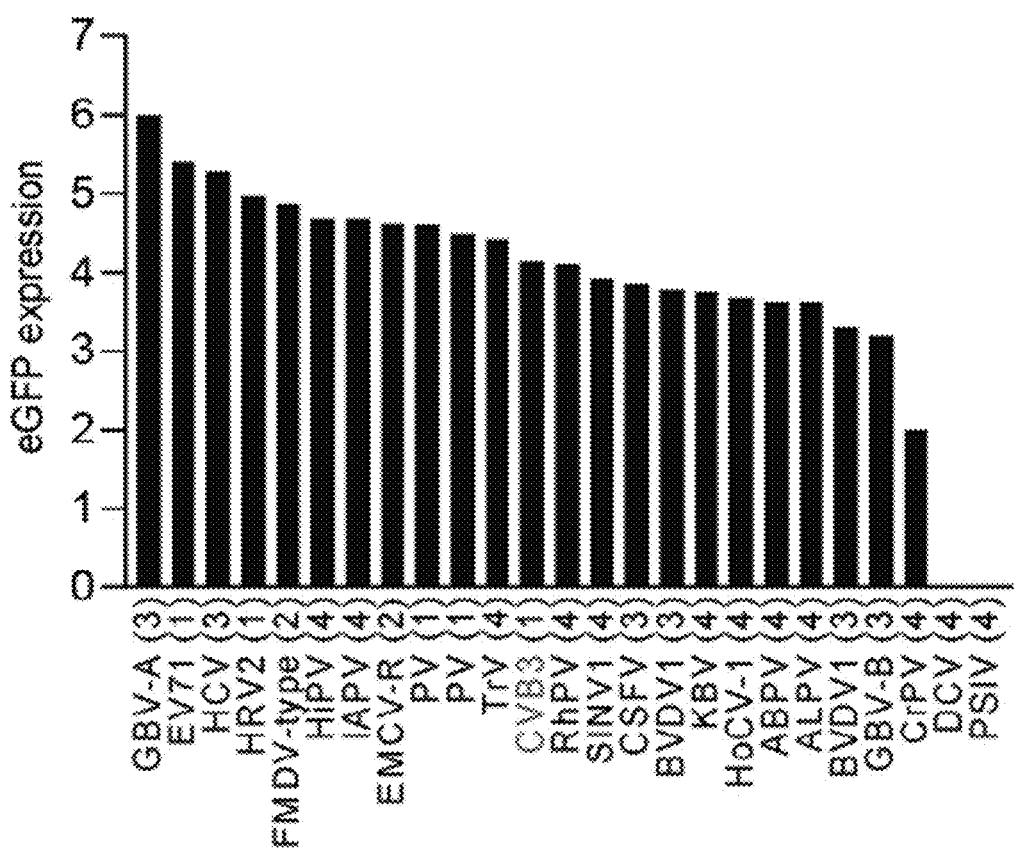

In comparison to FGFR1, the expression level of circFGFR1p is relatively low (FIGS. 7J and 7K), which indicates that circFGFR1p may not be a strong regulator under normal conditions. Nevertheless, many IRESs have been reported to have steady cap-independent translation activity under stress conditions, including the IRES of some endogenous protein-coding circRNAs, such as circZNF-609. Thus, the cap-independent translation activity of circFGFR1 IRES under stress conditions, such as under heat-shock, was further examined. First, cells were transfected with oligo-split-eGFP-circRNA reporter construct driven by circFGFR1 IRES and quantified the circFGFR1 IRES activity with or without the heat-shock. The results demonstrated that the cap-independent translation activity of 15 FGFR1 IRES remains steady during the heat-shock (FIG. 17E). Then, the FGFR1 and circFGFR1p protein levels were examined under the heat-shock condition. It was observed that FGFR1 protein level was downregulated after the heat-shock (FIGS. 7J and 7L), which is likely due to the global reduction in cap-dependent translation caused by the changes in the phosphorylation states of many eukaryotic initiation factors and the sequestration of eIF4G by Hsc70 during the heat-shock. On the other hand, the circFGFR1p level, which is regulated by cap-independent translation, remained steady after the heat-shock (FIG. 7J, 7L and FIGS. 17F and 17G). The result suggests that during heat shock although the global FGFR1 cap-dependent translation reduction is not directly caused by the circFGFR1p level, the reduced FGFR1 level and stable circFGFR1p level enhances the circFGFR1p dominant negative effect and further lower the cell growth rate. Moreover, FGFR1 has been shown to form homomultimers when induced by cell adhesion molecules. The nature of FGFR1 oligomerization may further enhance the dominant-negative effect of circFGFR1p because one circFGFR1p can join and "poison" the signaling ability or lead to degradation of more FGFR1 molecules. These phenomena may explain how lowly expressed circFGFR1p can effectively regulate highly expressed FGFR1 and suppress cell proliferation under heat shock or other forms of cell stress conditions (FIGS. 17H and 17I).

Interestingly, while the circFGFR1 IRES (oligo index: 8228) displayed strong cap-independent translation activity on the circRNA (top 2%), the same IRES showed very weak cap-independent translation activity on the linear RNA (bottom 10%) (Weingarten-Gabbay et al., 2016). This observation suggests that the cap-independent translation activity of circFGFR1 IRES is preferentially activated on circFGFR1 rather than the linear FGFR1 transcripts. This circRNA-5 biased IRES activity of circFGFR1 IRES may also explain how under the heat-shock condition circFGFR1 IRES can selectively produce the steady amount of circFGFR1p without increasing the level of FGFR1 protein isoforms produced from the cap-independent activity of circFGFR1 IRES on the linear FGFR1 transcripts, allowing circFGFR1p to regulate FGFR1 functions more effectively. In sum, the findings presented above demonstrated that with the disclosed methods, not a novel circRNA-encoded protein, circFGFR1p, was discovered that negatively regulates FGFR1 and suppresses cell proliferation through a dominant-negative mechanism under stress conditions. This study also reveals an important regulatory mechanism of circRNAs and their encoded proteins.

Various embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

INCORPORATION BY REFERENCE

All references, including publications, patent applications, and patents, cited herein are hereby incorporated by reference to the same extent as if each reference were individually and specifically indicated to be incorporated by reference and were set forth in its entirety herein.

NUMBERED EMBODIMENTS

Notwithstanding the appended claims, the following numbered embodiments also form part of the instant disclosure.

1. A polynucleotide sequence encoding a circular RNA molecule; wherein the circular RNA molecule comprises a protein-coding nucleic acid sequence region and an internal ribosome entry site (IRES) sequence region operably linked to the protein-coding nucleic acid sequence, wherein the IRES sequence region comprises: at least one sequence region having an RNA secondary structure element; and a sequence region that is complementary to an 18S ribosomal RNA (rRNA); wherein the IRES sequence region has a minimum free energy (MFE) of less than −18.9 kJ/mol and a melting temperature of at least 35.0° C.; and wherein the RNA secondary structure element is formed from the nucleotides at about position 40 to about position 60 of the IRES, wherein the first nucleic acid at the 5' end of the IRES is considered to be position 1.

2. The polynucleotide sequence of embodiment 1, wherein the protein coding nucleic acid sequence region is operably linked to the IRES sequence region in a non-native configuration.

3. The polynucleotide sequence of embodiment 1 or 2, wherein the polynucleotide sequence is a DNA sequence.

4. The polynucleotide sequence of any one of embodiments 1-3, wherein the sequence that is complementary to an 18S rRNA is any one SEQ ID NO: 28977-28983.

5. The polynucleotide sequence of any one of embodiments 1-4, wherein the at least one RNA secondary structure element is located 5' to the sequence region that is complementary to an 18S rRNA.

6. The polynucleotide sequence of any one of embodiments 1-4, wherein the at least one RNA secondary structure element is located 3' to the sequence region that is complementary to an 18S rRNA.

7. The polynucleotide sequence of any one of embodiments 1-6, wherein the at least one RNA secondary structure element is a stem-loop.

8. The polynucleotide sequence of any one of embodiments 1-7, wherein the at least one RNA secondary structure element comprises any one of the nucleic acid sequences listed in Table 2.

9. The polynucleotide sequence of any one of embodiments 1-8, wherein the IRES sequence region is about 100 to about 1000 nucleotides in length.

10. The polynucleotide sequence of any one of embodiments 1-8, wherein the IRES sequence region is about 200 to about 800 nucleotides in length.

11. The polynucleotide sequence of any one of embodiments 1-8, wherein the IRES sequence is between 150-200 nucleotides, between 160-180 nucleotides, or between 200-210 nucleotides in length.

12. The polynucleotide sequence of any one of embodiments 1-11, comprising at least one non-coding functional sequence.

13. The polynucleotide sequence of embodiment 12, wherein the non-coding functional sequence comprises one or more (a) microRNA binding sites or (b) RNA binding protein binding sites.

14. The polynucleotide sequence of any one of embodiments 1-11, wherein the DNA sequence comprises an aptamer.

15. A recombinant circular RNA molecule encoded by the polynucleotide sequence of any one of embodiments 1-14.

16. A DNA sequence encoding a circular RNA molecule; wherein the circular RNA molecule comprises a protein-coding nucleic acid sequence region and an internal ribosome entry site (IRES) sequence region operably linked to the protein-coding nucleic acid sequence; wherein the IRES sequence region comprises any one of the nucleic acid sequences listed in SEQ ID NO: 1-228 or SEQ ID NO: 229-17201, or a nucleic acid sequence having at least 90% or at least 95% identity or homology thereto.

17. The DNA sequence of embodiment 16, wherein the protein-coding nucleic acid sequence is operably linked to the IRES sequence region in a non-native configuration.

18. The DNA sequence of any one of embodiments 16-17, wherein the IRES sequence region has a G-C content of at least 25%.

19. The DNA sequence of any one of embodiments 16-18, wherein the IRES sequence region comprises any one of the nucleic acid sequences of SEQ ID NO: 1-228.

20. The DNA sequence of any one of embodiments 16-18, wherein the IRES sequence region comprises any one of the nucleic acid sequences of SEQ ID NO: 229-17201.

21. The DNA sequence of any one of embodiments 16-20, wherein the IRES sequence region comprises the nucleic acid sequence of any one of SEQ ID NOs: 531, 2270, 2602, 3042, 3244, and 33948.

22. The DNA sequence of any one of embodiments 16-21, wherein the IRES sequence region comprises a human IRES.

23. The DNA sequence of any one of embodiments 16-22, wherein the protein coding-nucleic acid sequence region encodes a therapeutic peptide or protein.

24. The DNA sequence of any one of embodiments 16-23, wherein the circular RNA molecule comprises between about 200 nucleotides and about 10,000 nucleotides.

25. The DNA sequence of any one of embodiments 13-24, wherein the circular RNA molecule comprises a spacer between the IRES sequence region and a start codon of the protein-coding nucleic acid sequence region.

26. The DNA sequence of embodiment 25, wherein the length of the spacer is selected to increase translation of the protein-coding nucleic acid sequence region relative to translation of a circular RNA having either no spacer or a spacer that differs from the selected spacer.

27. The DNA sequence of any one of embodiments 16-26, wherein the IRES sequence region is configured to promote rolling circle translation.

28. The DNA sequence of any one of embodiments 16-26, wherein the protein-coding nucleic acid sequence region lacks a stop codon.

29. The DNA sequence of any one of embodiments 16-26, wherein (i) the IRES sequence region is configured to promote rolling circle translation, and (ii) the protein-coding nucleic acid sequence region lacks a stop codon.

30. A recombinant circular RNA molecule encoded by the DNA sequence of any one of embodiments 16-29.

31. A viral vector comprising the polynucleotide of any one of embodiments 1-14 or the DNA sequence of any one of embodiments 16-29.

32. The viral vector of embodiment 31, which is selected from the group consisting of an adeno-associated virus (AAV) vector, an adenovirus vector, a retrovirus vector, a lentivirus vector, a vaccinia and a herpesvirus vector.

33. The viral vector of embodiment 31 or 32, wherein the viral vector is an AAV.

34. The viral vector of embodiment 33, wherein the AAV serotype is selected from the group consisting of AAV1, AAV2, AAV3, AAV4, AAV5, AAV6, AAV8, AAV9, AAVrh10 or any variant thereof having substantially the same tropism.

35. A viral-like particle comprising the polynucleotide of any one of embodiments 1-14 or the DNA sequence of any one of embodiments 16-29.

36. A nonviral-like particle comprising the polynucleotide of any one of embodiments 1-14 or the DNA sequence of any one of embodiments 16-29.

37. A closed-ended DNA sequence comprising the polynucleotide of any one of embodiments 1-14 or the DNA sequence of any one of embodiments 16-29.

38. A plasmid comprising the polynucleotide of any one of embodiments 1-14 or the DNA sequence of any one of embodiments 16-29.

39. A mini-intronic plasmid vector comprising the polynucleotide of any one of embodiments 1-14 or the DNA sequence of any one of embodiments 16-29.

40. A composition comprising the polynucleotide of any one of embodiments 1-14, the DNA sequence of any one of embodiments 16-29, or a recombinant circular RNA molecule of embodiment 15 or 30.

41. The composition of embodiment 40, wherein the lipid nanoparticle is decorated.

42. A host cell comprising the polynucleotide of any one of embodiments 1-14, the DNA sequence of any one of embodiments 16-29, or a recombinant circular RNA molecule of embodiment 15 or 30.

43. A method of producing a protein in a cell, the method comprising contacting a cell with (a) the polynucleotide of any one of embodiments 1-14, (b) the DNA sequence of any one of embodiments 16-29, (c) the circular RNA molecule of any one of embodiments 15 or 30, (d) the viral vector of any one of embodiments 31-34, (e) the viral like particle of embodiment 35, (f) the nonviral-like particle of embodiment 36, (g) the closed-end DNA sequence of embodiment 37, (h) the plasmid of embodiment 38, (i) the mini-intronic plasmid vector of embodiment 39, or (j) the composition of any one of embodiments 40-41 under conditions whereby the protein-coding nucleic acid sequence of the circular RNA is translated and the protein is produced in the cell.

44. The method of embodiment 43, wherein 5' cap-dependent translation in the cell is impaired or nonexistent.

45. The method of embodiment 43 or 44, wherein the cell is in vivo.

46. The method of embodiment 45, wherein the cell is a mammalian cell.

47. The method of embodiment 46, wherein the mammalian cell is derived from a human.

48. The method of any one of embodiments 45-46, wherein production of the protein is tissue-specific.

49. The method of embodiment 48, wherein the tissue specificity is localized to a tissues selected from the group consisting of muscle, liver, kidney, brain, lung, skin, pancreas, blood, and heart.

50. The method of embodiment 43 or 44, wherein the cell is in vitro.

51. The method of any one of embodiments 43-48, wherein the protein is expressed recursively in the cell.

52. The method of any one of embodiments 43-51, wherein the half-life of the circular RNA in the cell is about 1 to about 7 days.

53. The method of any one of embodiments 43-55, wherein the protein is produced in the cell for at least about 10%, at least about 20%, or at least about 30% longer than if the protein-coding nucleic acid sequence is provided to the cell in a linear format RNA or encoded for transcription as a linear RNA.

54. A protein produced by the method of any one of embodiments 43-53.

55. A recombinant circular RNA molecule comprising a protein-coding nucleic acid sequence and an internal ribosome entry site (IRES) operably linked to the protein-coding nucleic acid sequence, wherein the IRES comprises: at least one RNA secondary structure; and a sequence that is complementary to an 18S ribosomal RNA (rRNA); wherein the IRES has a minimum free energy (MFE) of less than −18.9 kJ/mol and a melting temperature of at least 35.0° C.

56. The recombinant circular RNA molecule of embodiment 55, wherein the protein-coding nucleic acid sequence is operably linked to the IRES in a non-native configuration.

57. The recombinant circular RNA molecule of embodiment 55 or 56, wherein the sequence that is complementary to an 18S rRNA is encoded by any one of SEQ ID NO: 28977-28983.

58. The recombinant circular RNA molecule of any one of embodiments 55-57, wherein the at least one RNA secondary structure is located 5' to the sequence that is complementary to an 18S rRNA.

59. The recombinant circular RNA molecule of any one of embodiments 55-57, wherein the at least one RNA secondary structure is located 3' to the sequence that is complementary to an 18S rRNA.

60. The recombinant circular RNA molecule of any one of embodiments 55-59, wherein the at least one RNA secondary structure is a stem-loop.

61. The recombinant circular RNA molecule of any one of embodiments 55-59, wherein the at least one RNA secondary structure comprises a sequence encoded by any one of the DNA sequences listed in Table 2.

62. The recombinant circular RNA of any one of embodiments 55-61, wherein the IRES is about 100 to about 1000 nucleotides in length.

63. The recombinant circular RNA of any one of embodiments 55-61, wherein the IRES is about 200 to about 200 nucleotides in length.

64. The recombinant circular RNA of any one of embodiments 55-61, wherein the IRES sequence is between 150-200 nucleotides, between 160-180 nucleotides, or between 200-210 nucleotides in length.

65. The recombinant circular RNA of any one of embodiments 62-64, wherein the RNA secondary structure is formed from the nucleotides at about position 40 to about position 60 of the IRES, relative to the 5' end thereof.

66. The recombinant circular RNA of any one of embodiments 55-65, comprising at least one non-coding functional sequence.

67. The recombinant circular RNA of embodiment 66, wherein the non-coding functional sequence comprises one or more (a) microRNA binding sites or (b) RNA binding protein binding sites.

68. The recombinant circular RNA of any one of embodiments 55-65, wherein the circular RNA comprises an aptamer.

69. A recombinant circular RNA molecule comprising a protein-coding nucleic acid sequence and an internal ribosome entry site (IRES) operably linked to the protein-coding nucleic acid sequence; wherein the IRES is encoded by any one of the DNA sequences listed in SEQ ID NO: 1-228 or SEQ ID NO: 229-17201, or a DNA sequence having at least 90% or at least 95% identity or homology thereto.

70. The recombinant circular RNA molecule of embodiment 69, wherein the protein-coding nucleic acid sequence is operably linked to the IRES in a non-native configuration.

71. The recombinant circular RNA of any one of embodiments 55-70, wherein the recombinant circular RNA comprises a back-splice junction, and wherein the IRES is located within about 100 to about 200 nucleotides of the back-splice junction.

72. The recombinant circular RNA molecule of any one of embodiments 55-71, wherein the IRES has a G-C content of at least 25%.

73. The recombinant circular RNA molecule of any one of embodiments 55-72, wherein the IRES is encoded by any of the DNA sequences of SEQ ID NO: 1-228.

74. The recombinant circular RNA molecule of any one of embodiments 55-72, wherein the IRES is encoded by any one of the DNA sequences of SEQ ID NO: 229-17201.

75. The recombinant circular RNA molecule of embodiment 74, wherein the IRES is encoded by any one of the DNA sequences shown in SEQ ID NO: 531, 2270, 2602, 3042, 3244, 33948.

76. The recombinant circular RNA molecule of any one of embodiments 55-75, wherein the IRES is a human IRES.

77. The recombinant circular RNA molecule of any one of embodiments 55-76, wherein the protein coding-nucleic acid sequence encodes a therapeutic peptide or protein.

78. The recombinant circular RNA molecule of any one of embodiments 55-77, wherein the circular RNA comprises between about 200 nucleotides and about 10,000 nucleotides.

79. The recombinant circular RNA molecule of any one of embodiments 55-78, wherein the circular RNA molecule comprises a spacer between the IRES sequence region and a start codon of the protein-coding nucleic acid sequence region.

80. The recombinant circular RNA molecule of embodiment 79, wherein the length of the spacer is selected to increase translation of the protein-coding nucleic acid sequence region relative to translation of a circular RNA having either no spacer or a spacer that differs from the selected spacer.

81. The recombinant circular RNA molecule of any one of embodiments 55-78, wherein the IRES sequence region is configured to promote rolling circle translation.

82. The recombinant circular RNA molecule of any one of embodiments 55-78, wherein the protein-coding nucleic acid sequence region lacks a stop codon.

83. The recombinant circular RNA molecule of any one of embodiments 55-78, wherein (i) the IRES sequence region is configured to promote rolling circle translation, and (ii) the protein-coding nucleic acid sequence region lacks a stop codon.

84. A composition comprising the recombinant circular RNA molecule of any one of embodiments 55-83.

85. A host cell comprising the recombinant circular RNA molecule of any one of embodiments 55-83 or the composition of embodiment 84.

86. A method of producing a protein in a cell, the method comprising contacting a cell with the recombinant circular RNA molecule of any one of embodiments 55-83, or the composition of embodiment 84 under conditions whereby the protein-coding nucleic acid sequence is translated and the protein is produced in the cell.

87. The method of embodiment 86, wherein 5' cap-dependent translation in the cell is impaired or nonexistent.

88. The method of embodiment 86 or 87, wherein the cell is in vivo.

89. The method of embodiment 86 or 87, wherein the cell is a mammalian cell.

90. The method of embodiment 89, wherein the mammalian cell is derived from a human.

91. The method of any one of embodiments 55-90, wherein production of the protein is tissue-specific.

92. The method of embodiment 91, wherein the tissue specificity is localized to a tissues selected from the group consisting of muscle, liver, kidney, brain, lung, skin, pancreas, blood, and heart.

93 The method of embodiment 86 or 87, wherein the cell is in vitro.

94. The method of any one of embodiments 86-93, wherein the protein is expressed recursively in the cell.

95. The method of any one of embodiments 86-94, wherein the half-life of the circular RNA in the cell is about 1 to about 7 days.

96. The method of any one of embodiments 86-94, wherein the protein is produced in the cell for at least about 10%, at least about 20%, or at least about 30% longer than if the protein-coding nucleic acid sequence is provided to the cell in a linear format RNA or encoded for transcription as a linear RNA.

97. A protein produced by the method of any one of embodiments 86-96.

98. An oligonucleotide molecule comprising a nucleic acid sequence that hybridizes to an internal ribosome entry site (IRES) present on a circular RNA molecule and inhibits translation of the circular RNA molecule.

99. The oligonucleotide molecule of embodiment 98, wherein the circular RNA is a recombinant circular RNA.

100. The oligonucleotide molecule of embodiment 98, wherein the recombinant circular RNA is the recombinant circular RNA of any one of embodiments 55-83.

101. The oligonucleotide molecule of embodiment 98, wherein the circular RNA is a naturally occurring circular RNA.

102. The oligonucleotide molecule of any one of embodiments 98-101, wherein the oligonucleotide is an antisense oligonucleotide.

103. The oligonucleotide of embodiment 102, wherein the antisense oligonucleotide is a locked nucleic acid oligonucleotide (LNA).

104. The oligonucleotide of any one of embodiments 98-103, wherein the oligonucleotides is chemically modified at its 5' and/or its 3' end.

105. A method of inhibiting translation of a protein-coding nucleic acid sequence present on a circular RNA molecule, which method comprises contacting the circular RNA molecule with an oligonucleotide molecule of any one of embodiments 98-104, whereby the oligonucleotide molecule hybridizes to the RNA secondary structure and/or the nucleic acid sequence complementary to 18S rRNA present on the IRES of the circular RNA molecule and inhibits translation of the circular RNA molecule.

106. The method of embodiment 105, wherein the oligonucleotide hybridizes to the RNA secondary structure or the nucleic acid sequence that is complementary to 18S rRNA.

107. The method of embodiment 105, wherein the oligonucleotide hybridizes to the RNA secondary structure and the nucleic acid sequence that is complementary to 18S rRNA.

108. The method of embodiment 105, wherein a first oligonucleotide hybridizes to the RNA secondary structure and a second oligonucleotide hybridizes to the nucleic acid sequence that is complementary to 18S rRNA.

Lengthy table referenced here

US11560567-20230124-T00001

Please refer to the end of the specification for access instructions.

Lengthy table referenced here

US11560567-20230124-T00002

Please refer to the end of the specification for access instructions.

Lengthy table referenced here

US11560567-20230124-T00003

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11560567B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11560567B2). An electronic copy of the "Sequence Listing" will also be available from the USPTO upon request and payment of the fee set forth in 37 CFR 1.19(b)(3).

What is claimed is:

1. A recombinant circular RNA molecule comprising a protein-coding nucleic acid sequence and an internal ribosome entry site (IRES) sequence region operably linked to the protein-coding nucleic acid sequence, wherein the IRES sequence region comprises:
   (i) at least one RNA secondary structure element;
   (ii) a sequence that is complementary to an 18S ribosomal RNA (rRNA); and
   wherein the IRES sequence region has a minimum free energy (MFE) of less than −18.9 kJ/mol and a melting temperature of at least 35.0° C.

2. The recombinant circular RNA molecule of claim 1, wherein the protein-coding nucleic acid sequence is operably linked to the IRES sequence region in a non-native configuration.

3. The recombinant circular RNA molecule of claim 1, wherein the RNA secondary structure element is formed from the nucleotides at about position 40 to about position 60 of the IRES, wherein the first nucleic acid at the 5' end of the IRES sequence region is considered to be position 1.

4. The recombinant circular RNA molecule of claim 1, wherein the at least one RNA secondary structure element is a stem-loop.

5. The recombinant circular RNA molecule of claim 1, wherein the at least one RNA secondary structure element is located 5' to the sequence that is complementary to an 18s RNA.

6. The recombinant circular RNA molecule of claim 1, wherein the at least one RNA secondary structure element is located 3' to the sequence that is complementary to an 18s RNA.

7. The recombinant circular RNA molecule of claim 1, wherein the at least one RNA secondary structure element is formed from the nucleotides at about position 40 to about position 60 of the IRES, relative to the 5' end thereof.

8. The recombinant circular RNA molecule of claim 1, wherein the IRES sequence region has a G-C content of at least 25%.

9. The recombinant circular RNA molecule of claim 1, wherein the IRES sequence region is between 200-800 nucleotides in length, between 150-200 nucleotides, between 160-180 nucleotides, or between 200-210 nucleotides in length.

10. The recombinant circular RNA molecule of claim 1, wherein the IRES sequence region is derived from a human IRES.

11. The recombinant circular RNA molecule of claim 1, further comprising a spacer between the IRES sequence region and a start codon of the protein-coding nucleic acid sequence region.

12. The recombinant circular RNA molecule of claim 11, wherein the length of the spacer is selected to increase translation of the protein-coding nucleic acid sequence region of the recombinant circular RNA molecule relative to translation of a recombinant circular RNA molecule having either no spacer or a spacer that differs from the selected spacer.

13. The recombinant circular RNA molecule of claim 1, wherein the protein-coding nucleic acid sequence region lacks a stop codon.

14. A method of producing a protein in a cell, the method comprising contacting a cell with the recombinant circular RNA molecule of claim 1 under conditions whereby the protein-coding nucleic acid sequence region is translated and the protein is produced in the cell.

15. The method of claim 14, wherein the cell is in vivo.

16. The method of claim 15, wherein the cell is a mammalian cell.

17. The method of claim 16, wherein the mammalian cell is derived from a human.

18. The method claim 17, wherein production of the protein is tissue-specific.

19. The method claim 14, wherein the half-life of the recombinant circular RNA in the cell is about 1 to about 7 days.

20. The method of claim 14, wherein the protein is produced in the cell for at least about 10%, at least about 20%, or at least about 30% longer than if the protein-coding nucleic acid sequence region is provided to the cell in a linear format RNA or encoded for transcription as a linear RNA.

* * * * *